United States Patent
Uda et al.

(10) Patent No.: US 9,365,637 B2
(45) Date of Patent: Jun. 14, 2016

(54) ANTIVIRAL AGENT, ABZYME, PRIMER SET, METHOD FOR PRODUCING POLYNUCLEOTIDE, AND METHOD FOR PRODUCING POLYPEPTIDE

(75) Inventors: Taizo Uda, Oita (JP); Emi Hifumi, Oita (JP); Akira Nishizono, Oita (JP); Mitsue Arakawa, Yufu (JP)

(73) Assignee: JAPAN SCIENCE AND TECHNOLOGY AGENCY, Kawaguchi-shi, Saitama (JP)

( * ) Notice: Subject to any disclaimer, the term of this patent is extended or adjusted under 35 U.S.C. 154(b) by 164 days.

(21) Appl. No.: 13/579,529

(22) PCT Filed: Feb. 21, 2011

(86) PCT No.: PCT/JP2011/053752
§ 371 (c)(1),
(2), (4) Date: Aug. 16, 2012

(87) PCT Pub. No.: WO2011/102517
PCT Pub. Date: Aug. 25, 2011

(65) Prior Publication Data
US 2012/0322135 A1    Dec. 20, 2012

(30) Foreign Application Priority Data

Feb. 19, 2010 (JP) .................................. 2010-034998
Feb. 19, 2010 (JP) .................................. 2010-035021
Apr. 13, 2010 (JP) .................................. 2010-092461

(51) Int. Cl.
*A61K 39/00* (2006.01)
*A61K 39/395* (2006.01)
(Continued)

(52) U.S. Cl.
CPC .............. *C07K 16/10* (2013.01); *C12N 9/0002* (2013.01); *A61K 2039/505* (2013.01); *C07K 2317/21* (2013.01); *C07K 2317/30* (2013.01); *C07K 2317/515* (2013.01); *C07K 2317/56* (2013.01); *C07K 2317/76* (2013.01)

(58) Field of Classification Search
None
See application file for complete search history.

(56) References Cited

U.S. PATENT DOCUMENTS 6,723,833 B1 *  4/2004  Lowman et al. .......... 530/388.73
7,455,833 B2 * 11/2008  Thorpe et al. .............. 424/130.1
(Continued)

FOREIGN PATENT DOCUMENTS

JP   2002-543830 A   12/2002
JP   2004-97211 A    4/2004
(Continued)

OTHER PUBLICATIONS

Result 1 from WO 2004033658 A2 for SCORE search results 20130517_160905_us-13-579-529.30.rag.*
(Continued)

*Primary Examiner* — Benjamin P Blumel
*Assistant Examiner* — M. Franco Salvoza
(74) *Attorney, Agent, or Firm* — Casimir Jones, SC

(57) ABSTRACT

The present invention provides: a novel antiviral agent containing a human antibody κ light chain, a novel human abzyme containing a human antibody κ light chain; a polynucleotide, a vector, and a transformant, encoding a human antibody κ light chain of the above; a primer set for effectively obtaining a human antibody κ light chain having a function as an antiviral agent or abzyme; and a method for producing a polynucleotide and a method for producing a polypeptide, each of which method utilizes the primer set.

9 Claims, 38 Drawing Sheets

(51) Int. Cl.
*A61K 39/42* (2006.01)
*A61K 39/12* (2006.01)
*C07K 16/10* (2006.01)
*C12N 9/00* (2006.01)

(56) References Cited

U.S. PATENT DOCUMENTS

| | | |
|---|---|---|
| 2002/0102613 A1 | 8/2002 | Hoogenboom |
| 2004/0161741 A1 | 8/2004 | Rabani et al. |
| 2005/0009077 A1 | 1/2005 | Rabbani et al. |
| 2005/0137388 A1 | 6/2005 | Rabbani et al. |
| 2005/0170370 A1 | 8/2005 | Rabbani et al. |
| 2005/0202455 A1 | 9/2005 | Rabbani et al. |
| 2005/0202456 A1 | 9/2005 | Rabbani et al. |
| 2005/0214784 A1 | 9/2005 | Rabbani et al. |
| 2005/0233343 A1 | 10/2005 | Rabbani et al. |
| 2006/0014156 A1 | 1/2006 | Rabbani et al. |
| 2006/0024735 A1 | 2/2006 | Babani et al. |
| 2006/0024737 A1 | 2/2006 | Babani et al. |
| 2006/0024738 A1 | 2/2006 | Rabbani et al. |
| 2006/0029968 A1 | 2/2006 | Rabbani et al. |
| 2006/0030015 A1 | 2/2006 | Uda et al. |
| 2006/0035238 A1 | 2/2006 | Rabbani et al. |
| 2006/0035264 A1 | 2/2006 | Rabbani et al. |
| 2006/0040270 A1 | 2/2006 | Rabbani et al. |
| 2006/0040271 A1 | 2/2006 | Rabbani et al. |
| 2006/0040272 A1 | 2/2006 | Rabbani et al. |
| 2006/0057583 A1 | 3/2006 | Rabbani et al. |
| 2006/0088883 A1 | 4/2006 | Smider et al. |
| 2006/0099601 A1 | 5/2006 | Rabbani et al. |
| 2006/0172310 A1 | 8/2006 | Rabbani et al. |
| 2006/0257906 A1 | 11/2006 | Rabbani et al. |
| 2007/0072177 A1 | 3/2007 | Bakker et al. |
| 2007/0196828 A1 | 8/2007 | Rabbani et al. |
| 2007/0281863 A1 | 12/2007 | Rabbani et al. |
| 2008/0070799 A1 | 3/2008 | Bakker et al. |
| 2008/0108514 A1 | 5/2008 | Mattheus Hoogenboom |
| 2008/0226652 A1 | 9/2008 | Bakker et al. |
| 2009/0042733 A1 | 2/2009 | Rabbani et al. |
| 2010/0184042 A1 | 7/2010 | Rabbani et al. |
| 2010/0272724 A1 | 10/2010 | Bakker et al. |
| 2010/0310572 A1 | 12/2010 | Bakker et al. |

FOREIGN PATENT DOCUMENTS

| | | | |
|---|---|---|---|
| JP | 2006-501856 A | | 1/2006 |
| JP | 2006-197930 A | | 8/2006 |
| JP | 2006197930 A | * | 8/2006 |
| JP | 2008-508859 A | | 3/2008 |
| JP | 2010-17196 A | | 1/2010 |
| WO | WO 2004033658 A2 | * | 4/2004 |
| WO | 2004/106375 A1 | | 12/2004 |

OTHER PUBLICATIONS

Results 8, 9 from JP 2006197930 for SCORE search results 20130517__160905_us-13-579-529.54.rag.*
Accession No. S58207 from Welschof et al. "Ig light chain V region anti-F(ab')2- human (fragment)", (Jul. 1995).*
Hifumi, Emi, et al. "A-gata Influenza (H1N1) ni Taisuru Antigenase (Super Kotai Koso) (Antigenase (Super Catalytic Antibody) against Influenza A Virus (H1N1))", Bio Kanren Kagaku Godo Symposium Koen Yoshishu (Abstract of Biology-Related Chemistry Joint Symposium), 2006, p. 215.
Hifumi, E., et al. "Hitogata Kotai Koso no Sakusei to sono Koka (Production of Human Catalytic Antibody and its Effect)", 20th Symposium on Polymers and Biosciences, Jul. 21, 2010, pp. 43-44.
Uda, T., et al. "Super Catalytic Antibody and Antigenase," Journal of Bioscience and Bioengineering (2004), vol. 97, No. 3, pp. 143-152.
Hifumi, E., et al. "How and Why 41S-2 Antibody Subunits Acquire the Ability to Catalyze Decomposition of the Conserved Sequence of gp41 of HIV-1," Applied Biochemistry and Biotechnology (2000), vol. 83, pp. 209-220.
English translation of International Search Report, PCT/JP2011/053752, dated May 10, 2011.
Sharma, Vikram, et al., "A Human Germ Line Antibody Light Chain with Hydrolytic Properties Associated with Multimerization Status," J. Biol. Chem. 2009, 284:33079-33087.
Sharma, Vikram, et al., "A Human Germ Line Antibody Light Chain with Hydrolytic Properties Associated with Multimerization Status," J. Biol. Chem. 2009, 284: Supplementary Data.

* cited by examiner

DVVMTQTPLSLSVTPGQPASISC KSSQSLLHSDGKTYLY WYLQKPGH*SPH*LLIY EVSSRF
SGVPDRFSGSGSGTDFTLKISRVEAEDVGVYYC MQGLHLP QYTFGQGTKL (SEQ ID NO. 97)

(b)

16(A17)

DVVMTQSPLSLPVTLGQPASISC RSSQSLVHSDGNTYLN WFQQKPGQAPRRLIY KVSNRD
SGVPDRFSGSGSGTDFTLKISRVEAEDVGVYYC MQGTHWP PWTFGQGTKVEIK
RTVAAPSVFIFPPSDEQLKSGTASVVCLLNNFYPREAKVQWKVD
NALQSGNSQESVTEQDSKDSTYSLSSTLTLSKADYEKHKL*YACEVTHQGLSSPV TKSFNRGEC
(SEQ ID NO. 78)

(c)

7(A3/A19)

DVVMTQSPLSLPVTPGEPASISC RSSQSLLHSNGYNYLD WYLQKPGQSPQLLIY LGSNRA
SGVPDRFSGSGSGTDFTLKISRVEAEDVGVYYC MQALQTP RTFGQGTKVEIK (SEQ ID NO. 18)

(d)

11(A18b)

DVVMTQTPLSLSVTPGQPASISC KSSQSLLHSDGKTYLY WYLQKPGQSPQLLIY EVSSRF
SGVPDRFSGSGSGTDFTLKISRVEAEDVGVYYC MQGIHLP PVHFWPGDQAGDQT (?) (SEQ ID NO. 79)

FIG. 6

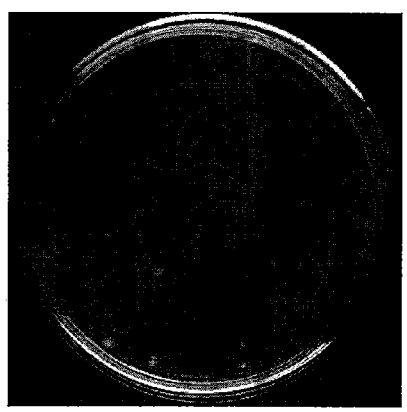
(a)

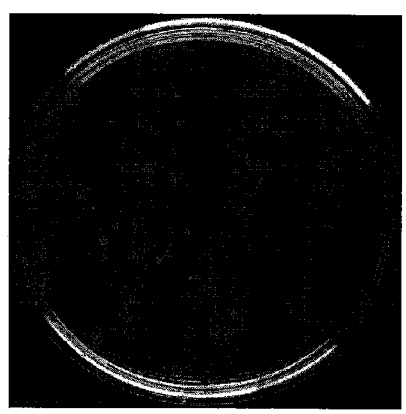
(b)

EVALUATION ON TEMP. & REACTION TIME

|  | A18#1 | |
|---|---|---|
|  | 24hr | 48hr |
| 15°C | 66.0 | 39.0 |
| 25°C | 31.7 | 2.4 |
| 30°C | 1.2 | – |

Assay condition : A18b#1 1mg/ml
Infection rate in infection using PBS is 100% for all temp.

(b)

EVALUATION ON CONC.

|  | 0.5mg/ml | 1.0mg/ml | 1.5mg/ml | 1.78mg/ml |
|---|---|---|---|---|
| 25°C | 59.2 | 20.7 | 0.5 | 10.9 |
| 30°C | 71.2 | 22.0 | 0.0 | 1.2 |
|  |  |  |  | exceptionally 24hr |

Assay condition : A18b#1 48hr reaction
Infection rate in infection using PBS is 100% for all conc.

Effect of rec. A18B#1 C220 A (Monomer) against VSV

MM: 1kb Plus DNA Ladder (Invitrogen)
(1): VK3bTOPO using PCR
(2): VK4aTOPO using PCR

FIG. 39

| | VARIABLE DOMAIN (CDR1, CDR2) | | SEQ ID NO. |
|---|---|---|---|
| #1-4 (A18b) | MDVVMTQTPLSLSVTPGQPASISCKSSQSLLHSDGKT-YLYWYLQKPGHSPHLLIYEVSS | 59 | 82 |
| #2-3 (A3/A19) | MDVVMTQSPLSLPVTPGEPASISCRSSQSLLYGNGNN-YLDWYLQKPGQSPQLLIYLGST | 59 | 83 |
| #4-1 (02/01) | MDVVMTQTPLSLSVTPGEPASISCRSTQSLLDSDGVNPSFDWYVQKPGQSPQLLIHRGFY | 60 | 84 |
| #5-2 (A3/A19) | MDVVMTQSPLSLPVTPGEPASISCRSSQSLLHSNGYN-YLDWYLQKPGQSPQLLIYLGSN | 59 | 85 |
| #6-2 (A18b) | MDVVMTQTPLSLSVTPGQPASISCKSSQSLLYSDGKT-YLYWYLQKPGQSPQLLIYEVSS | 59 | 23 |
| #7-2 (A3/A19) | MDVVMTQSPLSLPVTPGEPASISCRSSQSLLHSNGYN-YLDWYLQKPGQSPQLLIYLGSN | 59 | 19 |
| #8-2 (A18b) | MDVVMTQTPLSLSVTPGQPASLSCKSSQSLLHSDGKT-YLYWYLQKPGQSPQLLIYEVSS | 59 | 86 |
| #9a-2 (A18b) | MDVVMTQTPLSLSVTPGQPASISCKSSQSLLHSDGKT-YLYWYLQKPGQSPQLLIYEVSS | 59 | 87 |
| #10-3 (A18b) | MDVVMTQTPLSLSVTPGQPASISCKSSQSLLHSDGKT-YFYWYLQRPGRSPQLLIQEVSR | 59 | 88 |
| #11-1 (A18b) | MDIVMTQTPLSLSVTPGQPASISCKSSQSLLHSDGKT-YLYWYLQKPGQSPQLLIYEVSS | 59 | 89 |
| #12-1 (A3/A19) | MDVVMTQSPLSLPVTPGEPASISCLSSQSLLHSNGYN-YLDWYLQKPGQSPQLLIYRGSN | 59 | 90 |
| #13-1 (A3/A19) | MDVVMTQSPLSLPVTPGEPASISCRSSQSLLHSNGYN-YLDWYLQKPGQSPQLLIYLGSN | 59 | 91 |
| #14-1 (A3/A19) | MDIVMTQSPLSLPVTPGEPASISCRSSQSLLHSNGYN-YLDWYLQKPGQSPQLLIYLGSN | 59 | 92 |
| #15M-2 (A5) | MDVVMTQSPLSLPVTPGEAASISCRSSQSLLHNNGYT-YLYWFLQKARPVSTLLIYEVSN | 59 | 93 |
| #16WT-1 (A17) | MDVVMTQSPLSLPVTLGQPASISCRSSQSLVHSDGNT-YLNWFQQRPGQSPRRLIYKVSN | 59 | 17 |
| #18-1 (A18b) | MDVVMTQTPLSVSVTPGQPASVSCKSSQSLLYSDGKT-YLYWYLQRPGQSPQLLIYEVSR | 59 | 27 |
| #19-1 (A17) | MDIVMTQSPLSLPVTLGQPASISCRSSQSLVKSDGNT-YLSWFQQRPGQAPRRLFYRVSW | 59 | 94 |
| 22F6-4 (A3/A19) | MDIVMTQSPLSLPVTPGEPASISCRSSQSLLHSNGFN-YLDWYLQKPGQSPQLLIYLGST | 59 | 36 |
| 23D4-1 (A3/A19) | MDIVMTQSPLSLPVTPGEPASISCRSSQSLLHSNGYN-YLDWYLQKPGQSPQLLIYLGSN | 59 | 31 |
| 23F1-4 (A23) | MDIVMTQTPLSSPVTLGQPASISCRSSQSLVHSDGNT-YLSWLQQRPGQPPRLLIYKISN | 59 | 41 |

```
**:****:***  .** *:**:** *:***:  .:*.   :* *:.  . *:
```

| | CDR3, CONSTANT DOMAIN | | SEQ ID NO. |
|---|---|---|---|
| #1-4 (A18b) | RFSGVPDRFSGSGSGTDFTLKISRVEAEDVGVYYCMQGLHLPQYTFGQGTKLEIKRTVAA | 119 | 82 |
| #2-3 (A3/A19) | RASGVPDRFSGSGSGTDFQLKISRVEADDVGIYYCMQAQQGP-PTFGGGTKVEIKRTVAA | 118 | 83 |
| #4-1 (02/01) | RASGVPDRFSGSGSGTDFTLRISRVEAEDVGVYYCMQRIEFP-LTFGGGTKVEIKRTVAA | 119 | 84 |
| #5-2 (A3/A19) | RASGVPDRFSGSGSGTDFTLKISRVEAEDVGVYYCMQALQTR-FTFGPGTKVDIKRTVAA | 118 | 85 |
| #6-2 (A18b) | RFSGVPDRFSGSGSGTDFTLTISRVEAEDVGDYYCMQGIEIP-RTFGGGTKVEIKRTVAA | 118 | 23 |
| #7-2 (A3/A19) | RASGVPDRFSGSGSGTDFTLKISRVEAEDVGVYYCMQALQTP-RTFGQGTKVEIKRTVAA | 118 | 19 |
| #8-2 (A18b) | RFSGVPDRFSGSGSGTDFTLKISRVEAEDVGVYYCMEGTHLP-WTFGQGTKVEIKRTVAA | 118 | 86 |
| #9a-2 (A18b) | RFSGVPDRFSGSGSGTDFTLKISRVEAEDVGVYYCMQGIHLP-YTFGQGTKLEIKRTVAA | 118 | 87 |
| #10-3 (A18b) | RFSGVPDRFSGSGSGSDFTLKISRVEAEDVGVYYCMQGTYVP-HTFGQGTKVEIKRTVAA | 118 | 88 |
| #11-1 (A18b) | RFSGVPDRFSGSGSGTDFTLKISRVEAEDVGVYYCMQGIHLP-YTFGQGTKLEIKRTVAA | 118 | 89 |
| #12-1 (A3/A19) | RASGVPDRFSGSASGTDFTLKISKVEAEDVGVYYCMQGLST--RTFGQGTKVEIKRTVAA | 117 | 90 |
| #13-1 (A3/A19) | RASGVPDRFSGSGSGTDFTLKISRVEAEDVGVYYCMQALQTPPWTFGQGTKVEIKRTVAA | 119 | 91 |
| #14-1 (A3/A19) | RASGVPDRFSGSGSGTDFTLKISRVEAEDVGVYYCMQALQTP-RTFGQGTKLEIKRTVAA | 118 | 92 |
| #15M-2 (A5) | RFSGVPDRFSGSGSGTDFTLKISRVEAEDFGVYYCMQDAQDPPITFGQGTRLEIKRTVAA | 119 | 93 |
| #16WT-1 (A17) | RDSGVPDRFSGSGSGTDFTLKISRVEAEDVGVYYCMQGTHWPPWTFGQGTKVEIKRTVAA | 119 | 17 |
| #18-1 (A18b) | RFSGVPDRFSGSGSGTDFTLKISRVEAEDVGVYYCMQAIQLP-WTFGQGTKVDIKRTVAA | 118 | 27 |
| #19-1 (A17) | RDSGVPDRFRGSGSGTDFTLEISRVEAEDVGIYYCMQALQTP-PTFGGGTKVEIKRTVAA | 118 | 94 |
| 22F6-4 (A3/A19) | RASGVPDRFSGSGSGTDFTLRISRVEAEDVGVYFCMQAVQTP-FTFGPGTRLDIKRTVAA | 118 | 36 |
| 23D4-1 (A3/A19) | RASGVPDRFSGSGSGTDFTLKISRVEAEDVGVYYCMQALQTP-WTFGQGTKVEIKRTVAA | 118 | 31 |
| 23F1-4 (A23) | RFSGVPDRFSGSGAGTDFTLKISRVEAEDVGIYYCMQGLQTP-LTFGGGTKVDLKRTVAA | 118 | 41 |

|  |  |  | SEQ ID NO. |
|---|---|---|---|
| #1-4 (A18b) | PSVFIFPPSDEQLKSGTASVVCLLNNFYPREAKVQWKVDNALQSGNSQESVTEQDSKDST | 179 | 82 |
| #2-3 (A3/A19) | PSVFIFPPSDEQLKSGTASVVCLLNNFYPREAKVQWKVDNALQSGNSQESVTEQDSKDST | 178 | 83 |
| #4-1 (O2/O1) | PSVFIFPPSDEQLKSGTASVVCLLNNFYPREAKVQWKVDNALQSGNSQESVTEQDSKDST | 179 | 84 |
| #5-2 (A3/A19) | PSVFIFPPSDEQLKSGTASVVCLLNNFYPREAKVQWKVDNALQSGNSQESVTEQDSKDST | 178 | 85 |
| #6-2 (A18b) | PSVFIFPPSDEQLKSGTASVVCLLNNFYPREAKVQWKVDNALQSGNSQESVTEQDSKDST | 178 | 23 |
| #7-2 (A3/A19) | PSVFIFPPSDEQLKSGTASVVCLLNNFYPREAKVQWKVDNALQSGNSQESVTEQDSKDST | 178 | 19 |
| #8-2 (A18b) | PSVFIFPPSDEQLKSGTASVVCLLNNFYPREAKVQWKVDNALQSGNSQESVTEQDSKDST | 178 | 86 |
| #9a-2 (A18b) | PSVFIFPPSDEQLKSGTASVVCLLNNFYPREAKVQWKVDNALQSGNSQESVTEQDSKDST | 178 | 87 |
| #10-3 (A18b) | PSVFIFPPSDEQLKSGTASVVCLLNNFYPREAKVQWKVDNALQSGNSQESVTEQDSKDST | 178 | 88 |
| #11-1 (A18b) | PSVFIFPPSDEQLKSGTASVVCLLNNFYPREAKVQWKVDNALQSGNSQESVTEQDSKDST | 178 | 89 |
| #12-1 (A3/A19) | PSVFIFPPSDEQLKSGTASVVCLLNNFYPREAKVQWKVDNALQSGNSQESVTEQDSKDST | 177 | 90 |
| #13-1 (A3/A19) | PSVFIFPPSDEQLKSGTASVVCLLNNFYPREAKVQWKVDNALQSGNSQESVTEQDSKDST | 179 | 91 |
| #14-1 (A3/A19) | PSVFIFPPSDEQLKSGTASVVCLLNNFYPREAKVQWKVDNALQSGNSQESVTEQDSKDST | 178 | 92 |
| #15M-2 (A5) | PSVFIFPPSDEQLKSGTASVVCLLNNFYPREAKVQWKVDNALQSGNSQESVTEQDSKDST | 179 | 93 |
| #16WT-1 (A17) | PSVFIFPPSDEQLKSGTASVVCLLNNFYPREAKVQWKVDNALQSGNSQESVTEQDSKDST | 179 | 17 |
| #18-1 (A18b) | PSVFIFPPSDEQLKSGTASVVCLLNNFYPREAKVQWKVDNALQSGNSQESVTEQDSKDST | 178 | 27 |
| #19-1 (A17) | PSVFIFPPSDEQLKSGTASVVCLLNNFYPREAKVQWKVDNALQSGNSQESVTEQDSKDST | 178 | 94 |
| 22F6-4 (A3/A19) | PSVFIFPPSDEQLKSGTASVVCLLNNFYPREAKVQWKVDNALQSGNSQESVTEQDSKDST | 178 | 36 |
| 23D4-1 (A3/A19) | PSVFIFPPSDEQLKSGTASVVCLLNNFYPREAKVQWKVDNALQSGNSQESVTEQDSKDST | 178 | 31 |
| 23F1-4 (A23) | PSVFIFPPSDEQLKSGTASVVCLLNNFYPREAKVQWKVDNALQSGNSQESVTEQDSKDST | 178 | 41 |

\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*

|  |  |  | SEQ ID NO. |
|---|---|---|---|
| #1-4 (A18b) | YSLSSTLTLSKADYEKHKLYACEVTHQGLSSPVTKSFNRGECLEHHHHHH | 229 | 82 |
| #2-3 (A3/A19) | YSLSSTLTLSKADYEKHKLYACEVTHQGLSSPVTKSFNRGECLEHHHHHH | 228 | 83 |
| #4-1 (O2/O1) | YSLSSTLTLSKADYEKHKLYACEVTHQGLSSPVTKSFNRGECLEHHHHHH | 229 | 84 |
| #5-2 (A3/A19) | YSLSSTLTLSKADYEKHKLYACEVTHQGLSSPVTKSFNRGECLEHHHHHH | 228 | 85 |
| #6-2 (A18b) | YSLSSTLTLSKADYEKHKLYACEVTHQGLSSPVTKSFNRGECLEHHHHHH | 228 | 23 |
| #7-2 (A3/A19) | YSLSSTLTLSKADYEKHKLYACEVTHQGLSSPVTKSFNRGECLEHHHHHH | 228 | 19 |
| #8-2 (A18b) | YSLSSTLTLSKADYEKHKLYACEVTHQGLSSPVTKSFNRGECLEHHHHHH | 228 | 86 |
| #9a-2 (A18b) | YSLSSTLTLSKADYEKHKLYACEVTHQGLSSPVTKSFNRGECLEHHHHHH | 228 | 87 |
| #10-3 (A18b) | YSLSSTLTLSKADYEKHKLYACEVTHQGLSSPVTKSFNRGECLEHHHHHH | 228 | 88 |
| #11-1 (A18b) | YSLSSTLTLSKADYEKHKLYACEVTHQGLSSPVTKSFNRGECLEHHHHHH | 228 | 89 |
| #12-1 (A3/A19) | YSLSSTLTLSKADYEKHKLYACEVTHQGLSSPVTKSFNRGECLEHHHHHH | 227 | 90 |
| #13-1 (A3/A19) | YSLSSTLTLSKADYEKHKLYACEVTHQGLSSPVTKSFNRGECLEHHHHHH | 229 | 91 |
| #14-1 (A3/A19) | YSLSSTLTLSKADYEKHKLYACEVTHQGLSSPVTKSFNRGECLEHHHHHH | 228 | 92 |
| #15M-2 (A5) | YSLSSTLTLSKADYEKHKLYACEVTHQGLSSPVTKSFNRGECLEHHHHHH | 229 | 93 |
| #16WT-1 (A17) | YSLSSTLTLSKADYEKHKLYACEVTHQGLSSPVTKSFNRGECLEHHHHHH | 229 | 17 |
| #18-1 (A18b) | YSLSSTLTLSKADYEKHKLYACEVTHQGLSSPVTKSFNRGECLEHHHHHH | 228 | 27 |
| #19-1 (A17) | YSLSSTLTLSKADYEKHKLYACEVTHQGLSSPVTKSFNRGECLEHHHHHH | 228 | 94 |
| 22F6-4 (A3/A19) | YSLSSTLTLSKADYEKHKVYACEVTHQGLSSPVTKSFNRGECLEHHHHHH | 228 | 36 |
| 23D4-1 (A3/A19) | YSLSSTLTLSKADYEKHKVYACEVTHQGLSSPVTKSFNRGECLEHHHHHH | 228 | 31 |
| 23F1-4 (A23) | YSLSSTLTLSKADYEKHKVYACEVTHQGLSSPVTKSFNRGECLEHHHHHH | 228 | 41 |

Subgroup I

| | | AGCTCCTGGGGCTGCTAATG (SEQ ID NO. 44) | SEQ ID NO. |
|---|---|---|---|
| V kappa I, Z00001 | | atggacatgagggtccccgctcagctcctggggctcctgctgctctggctcccag--gtgccaaatgt | 95 |
| clone V1, M23851 | | atggacatgagggtccccgctcagctcctggggctcctgctgctctggctcccag--gtgccaaatgt | 95 |
| L11. M64858 | | atggacatgagggtccccgctcagctcctggggctcctgctgctctggctcccag--gtgccagatgt | 96 |
| V kappa I, Z00014 | | atggaggtccccgctcagctcctggggctcctgctgctctggctcccag--gtgccagatgt | 97 |
| V kappa I, Z00013 | | atggacatgagggtccccgctcagctcctggggctcctgctgctctggctcccag--gtgccagatgt | 96 |
| V kappa I, V01577 | | atggacatgagggtccccgctcagctcctggggctcctgctgctctggttcccag--gttccagatgc | 98 |
| V kappa I, V01576 | | atggacatgatggtccccgctcagctcctggggctcctgctgctctggttcccag--gttccagatgc | 99 |
| V kappa I, Z00006 | | atggacatgagggtccccgctcagctcctggggcttctgctgctctggctcccag--gtgccagatgt | 100 |
| IGKV-HK137, J00248 | | atggacatgagagtcctcgctcagctcctggggctcctgctgctctgtttcccag--gtgccagatgt | 101 |
| A30 X72808 | | atggacatgagggtccccgctcagctcctggggctcctgctgctctggttcccag--gtgccaggtgt | 102 |
| A20 X63398 | | atggacatgagggtccctgctcagctcctgggactcctgctgctctggctcccag--ataccagatgt | 103 |
| O18 M64856 | | atggacatgagggtccctgctcagctcctggggctcctgcagctctggctctcag--gtgccagatgt | 104 |
| O12 X59315 | | atggacatgagggtccccgctcagctcctggggctcctgctactctggctccgag--gtgccagatgt | 105 |
| O14 X59316 ORF | | atggacatgagggtccccgctcagctcctggggctcctactgctctgggtcccag--gtgccagatgt | 106 |
| V kappa I, Z00008 | | atggacatgagggtccccgctcagctcctggggctcctgctgctctggctcccag--gtgccagatgt | 96 |
| V-kappa-I, X17263 | | atggacatgagggtccccgctcagctcctggggctcctgctgctctggttcccag--gttccagatgc | 98 |
| V kappa I, V01576 | | atggacatgatggtccccgctcagctcctggggctcctgctgctctggttcccag--gttccagatgc | 99 |
| V-kappa-I, X17262 | | atggacatgagggtccccgctcagctcctggggcttctgctgctctggctcccag--gtgccagatgt | 100 |
| HK166 K01323 | | atggacatgagggtcctcgctcagctcctggggctcctgctgctctgtttcccag--gtgccagatgt | 101 |
| invariant region V00558 | | | |
| | | atggacatgagggtcctcgctcagctcctggggctcctgctgctctgtttcccag--gtgccagatgt | 101 |
| L14 X63392 | | atggacatgagggtccccgctcagctcctggggctcctgctgctctggttcccag--gtgccagatgt | 102 |
| O8. M64855 | | atggacatgagggtccctgctcagctcctggggctcctgctgctctggctctcag--gtgccagatgt | 107 |
| O4 and O5 X71893 ORF | | atggacatgagggtccccgctcagctcctggggctcctactgctctgggtcccag--gtgccagatgt | 108 |
| O2 X59312 | | atggacatgagggtccccgctcagctcctggggctcctgctactctggctccgag--gtgccagatgt | 105 |
| L22 X72816 ORF | | atggacatgagggtccccgctcagctcctggggctcctgctgctctggctcccag--gtgtcagattt | 108 |
| L23 X72817 | | atggacatgagggtgcccgctcagcgcctggggctcctgctgctctggttcccag--gtgccagatgt | 109 |

FIG. 44

SubgroupII

AGCTCCTGGGGCTGCTAATG (SEQ ID NO. 44)    SEQ ID NO.

| Clone | Sequence | SEQ ID NO. |
|---|---|---|
| A23 X12684 | atgaggctccttgctcagcttctggggctgctaatgctctgggtccctg--gatccagtggg | 110 |
| A19 X63397 | atgaggctccctgctcagctcctggggctgctaatgctctgggtctctg--gatccagtggg | 111 |
| VkA18b U41645 | atgaggctccctgctcagctcctggggctgctaatgctctggatccctg--gatccagtgcg | 112 |
| A17 X63403 | atgaggctccctgctcagctcctggggctgctaatgctctgggtcccag--gatccagtggg | 113 |
| O11 X59314 | atgaggctccctgctcagctcctggggctgctaatgctctgggtccctg--gatccagtgag | 114 |
| A7 X63401 ORF | atgaggctccttgctcagcttctggggctgctaatgctctgggtccctg--gatccagtggg | 110 |
| subclass II X12691 | atgaggctccctgctcagctcctggggctgctaatgctctgggtctctg--gatccagtggg | 111 |
| A2 M31952 | atgaggctccctgctcagctcctggggctgctaatgctctggatacctg--gatccagtgca | 115 |
| VkA2c U41644 | atgaggctccctgctcagctcctggggctgctaatgctctggatacctg--gatccagtgca | 115 |
| A1 X63402 | atgaggctccctgctcagctcctggggctgctaatgctctgggtcccag--gatccagtggg | 113 |
| O1 X59311 | atgaggctccctgctcagctcctggggctgctaatgctctgggtccctg--gatccagtgag | 114 |

SubgroupIII

AGCTCCTGGGGCTGCTAATG (SEQ ID NO. 44)    SEQ ID NO.

| Clone | Sequence | SEQ ID NO. |
|---|---|---|
| subgroup III X02725 ORF | atggaagccccagctcagcttctcttcctcctgctactctggctcccag--ataccaccaga | 116 |
| L10a X72812 ORF | atggaagccccagcgcagcttctcttcctcctgctactctggctcccag--ataccaccaga | 117 |
| subgroup III K02769 ORF | atggaagccccagctcagcttctcttcctcctgctactctggctcccag--ataccaccaga | 116 |
| IGKV3-7*04 FM164409 ORF | | |
| subgroup III, X01668 | atggaagccccagctcagcttctcttcctcctgctactctggctcccag--ataccaccgga | 118 |
| subgroup IIIa. K02768 | atggaagccccagctcagcttctcttcctcctgctactctggctcccag--ataccaccgga | 118 |
| clone Humkv328h5. M23090 | atggaagccccagcgcagcttctcttcctcctgctactctggctcccag--ataccactgga | 119 |
| A27 X12686 | atggaaacccagcgcagcttctcttcctcctgctactctggctcccag--ataccaccgga | 120 |
| 13k18, complete cds. L37729 | atggaaacccagcgcagcttctcttcctcctgctactctggctcccag--ataccaccgga | 120 |
| L25 X72820 | atggaaccatggaagccccagcacagcttcttcttcctcctgctactctggctcccag--ataccaccgga | 121 |
| V-kappa-III X17264 | atggaagccccagcgcagcttctcttcctcctgctactctggctcacag--ataccaccgga | 122 |
| L16 X72815 | atggaagccccagcgcagcttctcttcctcctgctactctggctcccag--ataccactgga | 119 |
| A11 gene X12687 | atggaaacccagcgcagcttctcttcctcctgctactctggctcccag--ataccaccgga | 123 |
| 13k04, L37728 | | |
| 13k07 and 13k09, L37727 | | |
| 13k16 and 13k17, L37730 | | SEQ ID NO. |
| 3A7 L19271 | acctcctgctactctggctcccag | 124 |
| 3A9 L19272 | acctcctgctactctggctcccag | 124 |

FIG. 45

SubgroupIV

AGCTCCTGGGGCTGCTAATG (SEQ ID NO. 44)

V kappa IV Z00023      atggtgttgcagacccaggtcttcatttctctgttgctctggatctctg-- gtgcctacggg (SEQ ID NO. 125)

SubgroupV

AGCTCCTGGGGCTGCTAATG (SEQ ID NO. 44)

X02485                atggggtcccaggttcacctcctcagcttcctcctcctttggatctctg-- ataccagggca (SEQ ID NO. 126)

SubgroupVI

AGCTCCTGGGGCTGCTAATG (SEQ ID NO. 44)

A26, X63399 ORF     atgttgccatcacaactcattgggtttctgctgctctggttccag--cctccaggggt (SEQ ID NO. 127)
A10, X12683 ORF     atgttgccatcacaactcattgggtttctgctgctctggttccag--cctccaggggt (SEQ ID NO. 127)
A14, M27751, ORF    atggtgtcccccgttgcaattcctgcggcttctgctcctctgggttccag--cctccaggggt (SEQ ID NO. 128)

FIG. 46

| | | SEQ ID NO. |
|---|---|---|
| Subgroup I : | agctcctggggctcctgctg | 129 |
| Subgroup II : | agctcctggggctgctaatg | 44 |
| Subgroup III : | ttctcttcctcctgctactc | 130 |
| Subgroup IV : | tcatttctctgttgctctgg | 131 |
| Subgroup V : | tcctcagcttcctcctcctt | 132 |
| Subgroup VI : | ggtttctgctgctctgggtt | 133 |

FIG. 47

Subgroup I

| | GATRTTGTGATGACYCAG (R=A or G, Y=C or T) (SEQ ID NO. 45) | SEQ ID NO. |
|---|---|---|
| V kappa I, Z00001 | gacatccagatgacccagtctccttccaccctgtctgcatctgtaggagacagagtcaccatcacttgccgg | 134 |
| clone V1, M23851 | gacatccagatgacccagtctccttccaccctgtctgcatctgtaggagacagagtcaccatcatttgccgg | 135 |
| L12a, X72813 | gacatccagatgacccagtctccttccaccctgtctgcatctgtaggagacagagtcaccatcacttgccgg | 134 |
| L11, M64858 | gccatccagatgacccagtctccatcctccctgtctgcatctgtaggagacagagtcaccatcacttgccgg | 136 |
| V kappa I, Z00014 | gccatccggatgacccagtctccatcctcattctctgcatctacaggagacagagtcaccatcacttgtcgg | 137 |
| V kappa I, Z00013 | gacatccagttgacccagtctccatccttcctgtctgcatctgtaggagacagagtcaccatcacttgccgg | 138 |
| V kappa I, V01577 | gacatccagatgacccagtctccatcttccgtgtctgcatctgtaggagacagagtcaccatcacttgtcgg | 139 |
| V kappa I, V01576 | gacatccagatgacccagtctccatcttccgtgtctgcatctgtaggagacagagtcaccatcacttgtcgg | 139 |
| V kappa I, Z00006 | gccatccagttgacccagtctccatcctccctgtctgcatctgtaggagacagagtcaccatcacttgccgg | 140 |
| IGKV-HK137, J00248 | gacatccagatgacccagtctccatcctcactgtctgcatctgtaggagacagagtcaccatcacttgtcg | 141 |
| A30 X72808 | gacatccagatgacccagtctccatcctccctgtctgcatctgtaggagacagagtcaccatcacttgccg | 142 |
| A20 X63398 | gacatccagatgacccagtctccatcctccctgtctgcatctgtaggagacagagtcaccatcacttgccgg | 143 |
| O18, M64856 | gacatccagatgacccagtctccatcctccctgtctgcatctgtaggagacagagtcaccatcacttgccag | 143 |
| O12 X59315 | gacatccagatgacccagtctccatcctccctgtctgcatctgtaggagacagagtcaccatcacttgccgg | 143 |
| O14 X59316 ORF | gacatccagttgacccagtctccatcctccctgtctgcatctgtaggagacagagtcaccatcacttgccgg | 144 |
| V kappa I, Z00008 | gtcatctggatgacccagtctccatcctctactctgcatctacaggagacagagtcaccatcagttgtcgg | 145 |
| V-kappa-I, X17263 | gacatccagatgacccagtctccatcttctgtgtctgcatctgtaggagacagagtcaccatcacttgtcgg | 146 |
| V kappa I, V01576 | gacatccagatgacccagtctccatcttccgtgtctgcatctgtaggagacagagtcaccatcacttgtcgg | 139 |
| V-kappa-I, X17262 | gacatccagttgacccagtctccatcctccctgtctgcatctgtaggagacagagtcaccatcacttgccgg | 144 |
| V-kappa-1, K01323 | gacatccagatgacccagtctccatcctcactgtctgcatctgtaggagacagagtcaccatcacttgtcgg | 147 |
| invariant region V00558 | | |
| | gacatccagatgacccagtctccatcctcactgtctgcatctgtaggagacagagtcaccatcacttgtcgg | 147 |
| IGKV1D-17*02 FM164407 | gacatccagatgacccagtctccatctgccatgtctgcatctgtaggagacagagtcaccatcacttgtcgg | 148 |
| 08, M64855 | gacatccagatgacccagtctccatcctccctgtctgcatctgtaggagacagagtcaccatcacttgccag | 149 |
| O4 and O5 X71893 ORF | gacatccagttgacccagtctccatcctccctgtctgcatctgtaggagacagagtcaccatcacttgccgg | 144 |
| 02 X59312 | gacatccagatgacccagtctccatcctccctgtctgcatctgtaggagacagagtcaccatcacttgccgg | 143 |
| L22 X72816 ORF | gacatccagatgatccagtctccatctttcctgtctgcatctgtaggagacagagtcagtatcatttgctgg | 150 |
| L23 X72817 | gccatccggatgacccagtctccattctccctgtctgcatctgtaggagacagagtcaccatcacttgctgg | 151 |

FIG. 48

Subgroup II

| | GATRTTGTGATGACYCAG (R=A or G, Y=C or T) (SEQ ID NO. 45) | SEQ ID NO. |
|---|---|---|
| A23 X12684 | gatattgtgatgacccagactccactctcctcacctgtcacccttggacagccggcctccatctcctgcagg | 152 |
| A19 X63397 | gatattgtgatgactcagtctccactctccctgcccgtcacccctggagagccggcctccatctcctgcagg | 153 |
| VkA18b U41645 | gatattgtgatgacccagactccactctctctgtccgtcacccctggacagccggcctccatctcctgcaag | 154 |
| IGKV2-29*03 AJ783437 | gatattgtgatgaccagactccactctctctgtccgtcacccctggacagccggcctccatctcctgcaag | 154 |
| A17 X63403 | gatgttgtgatgactcagtctccactctccctgcccgtcacccttggacagccggcctccatctcctgcagg | 155 |
| IGKV2-30*02 FM164408 | gatgttgtgatgactcagtctccactctccctgcccgtcacccttggacagccggcctccatctcctgcagg | 155 |
| O11 X59314 | gatattgtgatgaccagactccactctccctgcccgtcacccctggagagccggcctccatctcctgcagg | 156 |
| V3a X59317 | | |
| A7 X63401 ORF | gatattgtgatgaccagactccactctcctcgcctgtcacccttggacagccggcctccatctccttcagg | 157 |
| cos142. AP001216 | | |
| DPK14 gene Z27499 | gagattgtgatgaccagactccactctccttgtctatcacccctggagagcaggcctccatgtcctgcagg | 158 |
| subclass II X12691 | gatattgtgatgactcagtctccactctccctgcccgtcacccctggagagccggcctccatctcctgcagg | 153 |
| A2 M31952 | gatattgtgatgaccagactccactctctctgtccgtcacccctggacagccggcctccatctcctgcaag | 154 |
| VkA2c U41644 | gatattgtgatgaccagactccactctctctgtccgtcacccctggacagccggcctccatctcctgcaag | 154 |
| A1 X63402 | gatgttgtgatgactcagtctccactctccctgcccgtcacccttggacagccggcctccatctcctgcagg | 155 |
| O1 X59311 | gatattgtgatgaccagactccactctccctgcccgtcacccctggagagccggcctccatctcctgcagg | 156 |

FIG. 49

Subgroup III

| | GATRTTGTGATGACYCAG (R=A or G, Y=C or T) (SEQ ID NO. 45) | SEQ ID NO. |
|---|---|---|
| subgroup III X02725 ORF | gaaattgtaatgacacagtctccacccaccctgtctttgtctccaggggaaagagtcaccctctcctgcagg | 159 |
| L10a X72812 ORF | gaaattgtaatgacacagtctccacccaccctgtctttgtctccaggggaaagagtcaccctctcctgcagg | 159 |
| subgroup III K02769 ORF | | |
| | gaaattgtaatgacacagtctccacccaccctgtctttgtctccaggggaaagagtcaccctctcctgcagg | 159 |
| IGKV3-7*04 FM164409 ORF | | |
| | gaaattgtaatgacacagtctccacccaccctgtctttgtctccaggggaaagagtcaccctctcctgcagg | 159 |
| subgroup III X01668 | gaaattgtgttgacacagtctccagccaccctgtctttgtctccaggggaaagagccaccctctcctgcagg | 160 |
| subgroup IIIa K02768 | gaaattgtgttgacacagtctccagccaccctgtctttgtctccaggggaaagagccaccctctcctgcagg | 160 |
| clone Humkv328h5. M23090 | | |
| | gaaatagtgatgacgcagtctccagccaccctgtctgtgtctccaggggaaagagccaccctctcctgcagg | 161 |
| A27 X12686 | gaaattgtgttgacgcagtctccaggcaccctgtctttgtctccaggggaaagagccaccctctcctgcagg | 162 |
| 13k18, L37729 | gaaattgtgttgacacagtctccagccaccctgtctttgtctccaggggaaagagccaccctctcctgcagg | 160 |
| L25 X72820 | gaaattgtaatgacacagtctccagccaccctgtctttgtctccaggggaaagagccaccctctcctgcagg | 163 |
| V-kappa-III X17264 | gaaattgtgttgacacagtctccagccaccctgtctttgtctccaggggaaagagccaccctctcctgcagg | 160 |
| L16 X72815 | gaaatagtgatgacgcagtctccagccaccctgtctgtgtctccaggggaaagagccaccctctcctgcagg | 161 |
| A11 X12687 | gaaattgtgttgacgcagtctccagccaccctgtctttgtctccaggggaaagagccaccctctcctgcggg | 164 |
| 13k04, L37728 | gaaattgtgttgacacagtctccagccaccctgtctttgtctccaggggaaagagccaccctctcctgcagg | 160 |
| 13k07 and 13k09, L37727 | gaaattgtgttgacacagtctccagccaccctgtctttgtctccaggggaaagagccaccctctcctgcagg | 160 |
| 13k16 and 13k17, L37730 | gaaattgtgttgacacagtctccaggcaccctgtctttgtctccaggggaaagagccaccctctcctgcagg | 165 |
| 3A7 L19271 | gaaattgtgttgacacagtctccagccaccctgtctttgtctccaggggaaagagccaccctctcctgcagg | 160 |
| 3A9 L19272 | gaaattgtgttgacgcagtctccagccaccctgtctttgtctccaggggaaagagccaccctctcctgcagg | 164 |

SubgroupIV

| | GATRTTGTGATGACYCAG (R=A or G, Y=C or T) (SEQ ID NO. 45) | |
|---|---|---|
| V kappa IV Z00023 | gacatcgtgatgacccagtctccagactccctggctgtgtctctgggcgagagggccaccatcaactgcaag | 166 |

SubgroupV

| | GATRTTGTGATGACYCAG (R=A or G, Y=C or T) (SEQ ID NO. 45) | |
|---|---|---|
| X02485 | gaaacgacactcacgcagtctccagcattcatgtcagcgactccaggagacaaagtcaacatctcctgcaaa | 167 |

SubgroupVI

| | GATRTTGTGATGACYCAG (R=A or G, Y=C or T) (SEQ ID NO. 45) | |
|---|---|---|
| A26, X63399 ORF | gaaattgtgctgactcagtctccagactttcagtctgtgactccaaaggagaaagtcaccatcacctgccgg | 168 |
| A10, X12683 ORF | gaaattgtgctgactcagtctccagactttcagtctgtgactccaaaggagaaagtcaccatcacctgccgg | 168 |
| A14, M27751 ORF | gatgttgtgatgacacagtctccagctttcctctctgtgactccaggggagaaagtcaccatcacctgccag | 169 |

FIG. 50

|  |  |  | SEQ ID NO. |
|---|---|---|---|
| Subgroup I | : | gacatccagatgacccag | 170 |
| Subgroup II | : | gatattgtgatgacccag | 171 |
| Subgroup III | : | gaaattgtaatgacacag | 172 |
| Subgroup IV | : | gacatcgtgatgacccag | 173 |
| Subgroup V | : | gaaacgacactcacgcag | 174 |
| Subgroup VI | : | gaaattgtgctgactcag | 175 |

SEQUENCE LISTING

```
<160> NUMBER OF SEQ ID NOS: 175

<210> SEQ ID NO 1
<211> LENGTH: 220
<212> TYPE: PRT
<213> ORGANISM: human

<400> SEQUENCE: 1

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly His Ser
        35                  40                  45

Pro His Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu His Leu Pro Gln Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205
```

Ser Pro Val Thr Lys Ser Phe Asn Arg Gly Glu Cys
    210                 215                 220

<210> SEQ ID NO 2
<211> LENGTH: 660
<212> TYPE: DNA
<213> ORGANISM: human

<400> SEQUENCE: 2
gatattgtga tgacccagac tccactctct ctgtccgtca cccctggaca gccggcctcc     60
atctcctgca gtctagtca gagcctcctg catagtgatg aaagaccta tttgtattgg    120 tacctgcaga agccaggcca ctctccacat ctcctaatct atgaggtttc cagccggttc    180
tctggagtgc cagataggtt cagtggcagc gggtcaggga cagatttcac actgaaaatc    240
agccgggtgg aggctgagga tgttggggtt tattactgca tgcaaggttt acaccttcct    300
cagtacactt ttggccaggg gaccaagctg gagatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaaact ctacgcctgc    600
gaagtcaccc atcagggcct gagctcgccc gtcacaaaga gcttcaacag gggagagtgt    660

<210> SEQ ID NO 3
<211> LENGTH: 220
<212> TYPE: PRT
<213> ORGANISM: human

<400> SEQUENCE: 3

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser

```
              195                 200                 205
Ser Pro Val Thr Lys Ser Phe Asn Arg Gly Glu Cys
    210                 215                 220

<210> SEQ ID NO 4
<211> LENGTH: 660
<212> TYPE: DNA
<213> ORGANISM: human

<400> SEQUENCE: 4
gatgttgtga tgactcagtc tccactctcc ctgcccgtca cccttggaca gccggcctcc      60
atctcctgca ggtctagtca agcctcgta cacagtgatg aaacaccta cttgaattgg      120 tttcagcaga ggccaggcca atctccaagg cgcctaattt ataaggtttc taaccgggac      180
tctggggtcc cagacagatt cagcggcagt gggtcaggca ctgatttcac actgaaaatc      240
agcagggtgg aggctgagga tgttggggtt tattactgca tgcaaggtac acactggcct      300
ccgtggacgt tcggccaagg gaccaaggtg gaaatcaaac gaactgtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga aacacaaact ctacgcctgc      600
gaagtcaccc atcagggcct gagctcgccc gtcacaaaga gcttcaacag gggagagtgt      660

<210> SEQ ID NO 5
<211> LENGTH: 219
<212> TYPE: PRT
<213> ORGANISM: human

<400> SEQUENCE: 5

Asp Val Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

Lys His Lys Leu Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 6
<211> LENGTH: 657
<212> TYPE: DNA
<213> ORGANISM: human

<400> SEQUENCE: 6
gatgttgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300
cgtacgttcg gccaagggac caaggtggaa atcaaacgaa ctgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaactcta cgcctgcgaa   600
gtcacccatc agggcctgag ctcgcccgtc acaaagagct tcaacagggg agagtgt      657

<210> SEQ ID NO 7
<211> LENGTH: 220
<212> TYPE: PRT
<213> ORGANISM: Artificial Sequence
<220> FEATURE:
<223> OTHER INFORMATION: Description of Artificial Sequence:modified
      human polypeptide

<400> SEQUENCE: 7

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly His Ser
        35                  40                  45

Pro His Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu His Leu Pro Gln Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Ala
    210                 215                 220

<210> SEQ ID NO 8
<211> LENGTH: 660
<212> TYPE: DNA
<213> ORGANISM: Artificial Sequence
<220> FEATURE:
<223> OTHER INFORMATION: Description of Artificial Sequence:modified
      human polynucleotide

<400> SEQUENCE: 8
gatattgtga tgacccagac tccactctct ctgtccgtca cccctggaca gccggcctcc    60
atctcctgca gtctagtca gagcctcctg catagtgatg aaagaccta tttgtattgg    120 tacctgcaga agccaggcca ctctccacat ctcctaatct atgaggtttc cagccggttc    180
tctggagtgc cagataggtt cagtggcagc gggtcaggga cagatttcac actgaaaatc    240
agccgggtgg aggctgagga tgttggggtt tattactgca tgcaaggttt acaccttcct    300
cagtacactt ttggccaggg gaccaagctg gagatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaact ctacgcctgc    600
gaagtcaccc atcagggcct gagctcgccc gtcacaaaga gcttcaacag gggagaggct    660

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:Artificially    Synthesized
      DNA

<400> SEQUENCE: 9
agttccatgg agctcctggg gctgctaatg                                      30

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:Artificially    Synthesized
      DNA

<400> SEQUENCE: 10
ccgtctcgag acactctccc ctgttgaag                                       29

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:Artificially    Synthesized
      DNA

<400> SEQUENCE: 11
agttccatgg atrttgtgat gacycag                                27

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence:Artificially
      Synthesized Sequence

<400> SEQUENCE: 12

Ala Leu Glu His His His His His His
1               5

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Seqence

<400> SEQUENCE: 13
gctctcgagc accaccacca ccaccactga                             30

<210> SEQ ID NO 14
<211> LENGTH: 113
<212> TYPE: PRT
<213> ORGANISM: human

<400> SEQUENCE: 14

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly His Ser
        35                  40                  45

Pro His Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu His Leu Pro Gln Tyr Thr Phe Gly Gln Gly Thr Lys Leu Glu Ile
            100                 105                 110

Lys

<210> SEQ ID NO 15
<211> LENGTH: 229
<212> TYPE: PRT
<213> ORGANISM: Artificial Sequence
<220> FEATURE:
<223> OTHER INFORMATION: Description of Artificial Sequence:Artificially
      Synthesized Seqence

<400> SEQUENCE: 15

Met Asp Val Val Met Thr Gln Thr Pro Leu Ser Leu Ser Val Thr Pro
1               5                   10                  15

Gly Gln Pro Ala Ser Ile Ser Cys Lys Ser Ser Gln Ser Leu Leu His
            20                  25                  30

Ser Asp Gly Lys Thr Tyr Leu Tyr Trp Tyr Leu Gln Lys Pro Gly His

```
            35                  40                  45
Ser Pro His Leu Leu Ile Tyr Glu Val Ser Ser Arg Phe Ser Gly Val
 50                  55                  60
Pro Asp Arg Phe Ser Gly Ser Gly Ser Gly Thr Asp Phe Thr Leu Lys
 65                  70                  75                  80
Ile Ser Arg Val Glu Ala Glu Asp Val Gly Val Tyr Tyr Cys Met Gln
                 85                  90                  95
Gly Leu His Leu Pro Gln Tyr Thr Phe Gly Gln Gly Thr Lys Leu Glu
                100                 105                 110
Ile Lys Arg Thr Val Ala Ala Pro Ser Val Phe Ile Phe Pro Pro Ser
            115                 120                 125
Asp Glu Gln Leu Lys Ser Gly Thr Ala Ser Val Val Cys Leu Leu Asn
130                 135                 140
Asn Phe Tyr Pro Arg Glu Ala Lys Val Gln Trp Lys Val Asp Asn Ala
145                 150                 155                 160
Leu Gln Ser Gly Asn Ser Gln Glu Ser Val Thr Glu Gln Asp Ser Lys
                165                 170                 175
Asp Ser Thr Tyr Ser Leu Ser Ser Thr Leu Thr Leu Ser Lys Ala Asp
            180                 185                 190
Tyr Glu Lys His Lys Leu Tyr Ala Cys Glu Val Thr His Gln Gly Leu
        195                 200                 205
Ser Ser Pro Val Thr Lys Ser Phe Asn Arg Gly Glu Ala Leu Glu His
    210                 215                 220
His His His His His
225

<210> SEQ ID NO 16
<211> LENGTH: 113
<212> TYPE: PRT
<213> ORGANISM: human

<400> SEQUENCE: 16

Asp Val Val Met Thr Gln Ser Pro Leu Ser Leu Pro Val Thr Leu Gly
 1                   5                  10                  15
Gln Pro Ala Ser Ile Ser Cys Arg Ser Ser Gln Ser Leu Val His Ser
             20                  25                  30
Asp Gly Asn Thr Tyr Leu Asn Trp Phe Gln Gln Arg Pro Gly Gln Ser
         35                  40                  45
Pro Arg Arg Leu Ile Tyr Lys Val Ser Asn Arg Asp Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Gly
                 85                  90                  95
Thr His Trp Pro Pro Trp Thr Phe Gly Gln Gly Thr Lys Val Glu Ile
            100                 105                 110
Lys

<210> SEQ ID NO 17
<211> LENGTH: 229
<212> TYPE: PRT
<213> ORGANISM: Artificial Sequence
<220> FEATURE:
<223> OTHER INFORMATION: Description of Artificial Sequence:Artificially
      Synthesized Seqence

<400> SEQUENCE: 17
```

```
Met Asp Val Val Met Thr Gln Ser Pro Leu Ser Leu Pro Val Thr Leu
1               5                   10                  15
Gly Gln Pro Ala Ser Ile Ser Cys Arg Ser Ser Gln Ser Leu Val His
                20                  25                  30
Ser Asp Gly Asn Thr Tyr Leu Asn Trp Phe Gln Gln Arg Pro Gly Gln
            35                  40                  45
Ser Pro Arg Arg Leu Ile Tyr Lys Val Ser Asn Arg Asp Ser Gly Val
    50                  55                  60
Pro Asp Arg Phe Ser Gly Ser Gly Ser Gly Thr Asp Phe Thr Leu Lys
65                  70                  75                  80
Ile Ser Arg Val Glu Ala Glu Asp Val Gly Val Tyr Tyr Cys Met Gln
                85                  90                  95
Gly Thr His Trp Pro Pro Trp Thr Phe Gly Gln Gly Thr Lys Val Glu
            100                 105                 110
Ile Lys Arg Thr Val Ala Ala Pro Ser Val Phe Ile Phe Pro Pro Ser
            115                 120                 125
Asp Glu Gln Leu Lys Ser Gly Thr Ala Ser Val Val Cys Leu Leu Asn
    130                 135                 140
Asn Phe Tyr Pro Arg Glu Ala Lys Val Gln Trp Lys Val Asp Asn Ala
145                 150                 155                 160
Leu Gln Ser Gly Asn Ser Gln Glu Ser Val Thr Glu Gln Asp Ser Lys
                165                 170                 175
Asp Ser Thr Tyr Ser Leu Ser Ser Thr Leu Thr Leu Ser Lys Ala Asp
            180                 185                 190
Tyr Glu Lys His Lys Leu Tyr Ala Cys Glu Val Thr His Gln Gly Leu
    195                 200                 205
Ser Ser Pro Val Thr Lys Ser Phe Asn Arg Gly Glu Ala Leu Glu His
210                 215                 220
His His His His His
225

<210> SEQ ID NO 18
<211> LENGTH: 112
<212> TYPE: PRT
<213> ORGANISM: human

<400> SEQUENCE: 18

Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
                20                  25                  30
Asn Gly Tyr Asn Tyr Leu Asp Trp Tyr Leu Gln Lys Pro Gly Gln Ser
            35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Pro Arg Thr Phe Gly Gln Gly Thr Lys Val Glu Ile Lys
            100                 105                 110

<210> SEQ ID NO 19
<211> LENGTH: 228
<212> TYPE: PRT
```

<213> ORGANISM: Artificial Sequence
<220> FEATURE:
<223> OTHER INFORMATION: Description of Artificial Sequence:Artificially Synthesized Seqence

<400> SEQUENCE: 19

```
Met Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Thr Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Ala Leu Glu His His
    210                 215                 220

His His His His
225
```

<210> SEQ ID NO 20
<211> LENGTH: 219
<212> TYPE: PRT
<213> ORGANISM: human

<400> SEQUENCE: 20

```
Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Arg Val Glu Ala Glu Asp Val Gly Asp Tyr Tyr Cys Met Gln Gly
                85                  90                  95

Ile Glu Ile Pro Arg Thr Phe Gly Gly Gly Thr Lys Val Glu Ile Lys
```

```
            100                 105                 110
Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 21
<211> LENGTH: 657
<212> TYPE: DNA
<213> ORGANISM: human

<400> SEQUENCE: 21
gatgttgtga tgactcagac tccactctct ctgtccgtca cccctggaca gccggcctcc      60
atctcctgca agtctagtca gagcctcctg tatagtgatg aaagaccta  tttgtattgg     120 tacctgcaga agccaggcca gtctccacag ctcctaatct atgaagtttc cagccggttc     180
tcaggagtgc cagataggtt cagtggcagc gggtcaggga cagatttcac actgacaatc     240
agccgggtgg aggctgagga tgttggggat tattactgca tgcaaggtat agaaattcct     300
cggactttcg gcggagggac caaggtggag atcaaacgaa ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaactcta cgcctgcgaa     600
gtcacccatc agggcctgag ctcgcccgtc acaaagagct tcaacagggg agagtgt        657

<210> SEQ ID NO 22
<211> LENGTH: 112
<212> TYPE: PRT
<213> ORGANISM: human

<400> SEQUENCE: 22

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Arg Val Glu Ala Glu Asp Val Gly Asp Tyr Tyr Cys Met Gln Gly
                85                  90                  95
```

```
Ile Glu Ile Pro Arg Thr Phe Gly Gly Gly Thr Lys Val Glu Ile Lys
            100                 105                 110

<210> SEQ ID NO 23
<211> LENGTH: 228
<212> TYPE: PRT
<213> ORGANISM: Artificial Sequence
<220> FEATURE:
<223> OTHER INFORMATION: Description of Artificial Sequence:Artificailly
      synthesized sequence

<400> SEQUENCE: 23

Met Asp Val Val Met Thr Gln Thr Pro Leu Ser Leu Ser Val Thr Pro
1               5                   10                  15

Gly Gln Pro Ala Ser Ile Ser Cys Lys Ser Ser Gln Ser Leu Leu Tyr
            20                  25                  30

Ser Asp Gly Lys Thr Tyr Leu Tyr Trp Tyr Leu Gln Lys Pro Gly Gln
        35                  40                  45

Ser Pro Gln Leu Leu Ile Tyr Glu Val Ser Ser Arg Phe Ser Gly Val
50                  55                  60

Pro Asp Arg Phe Ser Gly Ser Gly Ser Gly Thr Asp Phe Thr Leu Thr
65                  70                  75                  80

Ile Ser Arg Val Glu Ala Glu Asp Val Gly Asp Tyr Tyr Cys Met Gln
                85                  90                  95

Gly Ile Glu Ile Pro Arg Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Ala Leu Glu His His
    210                 215                 220

His His His His
225

<210> SEQ ID NO 24
<211> LENGTH: 219
<212> TYPE: PRT
<213> ORGANISM: human

<400> SEQUENCE: 24

Asp Val Val Met Thr Gln Thr Pro Leu Ser Val Ser Val Thr Pro Gly
1               5                   10                  15

Gln Pro Ala Ser Val Ser Cys Lys Ser Ser Gln Ser Leu Leu Tyr Ser
            20                  25                  30

Asp Gly Lys Thr Tyr Leu Tyr Trp Tyr Leu Gln Arg Pro Gly Gln Ser
        35                  40                  45

Pro Gln Leu Leu Ile Tyr Glu Val Ser Arg Arg Phe Ser Gly Val Pro
50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Ile Gln Leu Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 25
<211> LENGTH: 657
<212> TYPE: DNA
<213> ORGANISM: human

<400> SEQUENCE: 25
gatgttgtga tgactcagac tccactctct gtgtccgtca cccctggaca gccggcctcc      60
gtctcctgca gtctagtcag agcctcctg tatagtgatg aaagaccta tttgtattgg     120 tacctgcaga ggccaggcca gtctccacaa ctcctaatct atgaggtttc aggcggttc     180 tctggagtgc cagataggtt tagtggcagc gggtcaggga cagatttcac actgaaaatc     240
agccgggtgg aggctgagga tgttggggtt tattactgca tgcaagctat acagcttcct     300
tggacgttcg gccaagggac caaggtggat atcaaacgaa ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaactcta cgcctgcgaa     600
gtcacccatc agggcctgag ctcgcccgtc acaaagagct tcaacagggg agagtgt         657

<210> SEQ ID NO 26
<211> LENGTH: 112
<212> TYPE: PRT
<213> ORGANISM: human

<400> SEQUENCE: 26

Asp Val Val Met Thr Gln Thr Pro Leu Ser Val Ser Val Thr Pro Gly
  1               5                  10                  15

Gln Pro Ala Ser Val Ser Cys Lys Ser Ser Gln Ser Leu Leu Tyr Ser
             20                  25                  30

Asp Gly Lys Thr Tyr Leu Tyr Trp Tyr Leu Gln Arg Pro Gly Gln Ser
         35                  40                  45

Pro Gln Leu Leu Ile Tyr Glu Val Ser Arg Arg Phe Ser Gly Val Pro
     50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Ile Gln Leu Pro Trp Thr Phe Gly Gln Gly Thr Lys Val Asp Ile Lys
            100                 105                 110
```

<210> SEQ ID NO 27
<211> LENGTH: 228
<212> TYPE: PRT
<213> ORGANISM: Artificial Sequence
<220> FEATURE:
<223> OTHER INFORMATION: Description of Artificial Sequence:Artificially
      Synthesized Seqence

<400> SEQUENCE: 27

```
Met Asp Val Val Met Thr Gln Thr Pro Leu Ser Val Ser Val Thr Pro
 1               5                  10                  15

Gly Gln Pro Ala Ser Val Ser Cys Lys Ser Ser Gln Ser Leu Leu Tyr
                 20                  25                  30

Ser Asp Gly Lys Thr Tyr Leu Tyr Trp Tyr Leu Gln Arg Pro Gly Gln
             35                  40                  45

Ser Pro Gln Leu Leu Ile Tyr Glu Val Ser Arg Arg Phe Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Ala Ile Gln Leu Pro Trp Thr Phe Gly Gln Gly Thr Lys Val Asp Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Ala Leu Glu His His
    210                 215                 220

His His His His
225
```

<210> SEQ ID NO 28
<211> LENGTH: 219
<212> TYPE: PRT
<213> ORGANISM: human

<400> SEQUENCE: 28

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30
```

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 29
<211> LENGTH: 657
<212> TYPE: DNA
<213> ORGANISM: human

<400> SEQUENCE: 29
gatattgtga tgactcagtc tccactctcc ctgcccgtca cccctggaga gccggcctcc      60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactccc    300
tggacgttcg gccaagggac caaggtggaa atcaaacgaa ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt       657

<210> SEQ ID NO 30
<211> LENGTH: 112
<212> TYPE: PRT
<213> ORGANISM: human

<400> SEQUENCE: 30

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser

```
                    20                  25                  30

Asn Gly Tyr Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Trp Thr Phe Gly Gln Gly Thr Lys Val Glu Ile Lys
                100                 105                 110

<210> SEQ ID NO 31
<211> LENGTH: 228
<212> TYPE: PRT
<213> ORGANISM: Artificial Sequence
<220> FEATURE:
<223> OTHER INFORMATION: Description of Artificial Sequence:Artificially
      Synthesized Seqence

<400> SEQUENCE: 31

Met Asp Ile Val Met Thr Gln Ser Pro Leu Ser Leu Pro Val Thr Pro
 1               5                  10                  15

Gly Glu Pro Ala Ser Ile Ser Cys Arg Ser Ser Gln Ser Leu Leu His
                 20                  25                  30

Ser Asn Gly Tyr Asn Tyr Leu Asp Trp Tyr Leu Gln Lys Pro Gly Gln
                35                  40                  45

Ser Pro Gln Leu Leu Ile Tyr Leu Gly Ser Asn Arg Ala Ser Gly Val
         50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Ala Leu Gln Thr Pro Trp Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Ala Leu Glu His His
    210                 215                 220

His His His His
225

<210> SEQ ID NO 32
<211> LENGTH: 687
<212> TYPE: DNA
<213> ORGANISM: Artificial Sequence
<220> FEATURE:
```

<223> OTHER INFORMATION: Description of Artificial Sequence:Artificially
      Synthesized Seqence

<400> SEQUENCE: 32

```
atggatattg tgatgactca gtctccactc tccctgcccg tcaccctgg agagccggcc      60
tccatctcct gcaggtctag tcagagcctc ctgcatagta atggatacaa ctatttggat    120
tggtacctgc agaagccagg gcagtctcca cagctcctga tctatttggg ttctaatcgg    180
gcctccgggg tccctgacag gttcagtggc agtggatcag gcacagattt tacactgaaa    240
atcagcagag tggaggctga ggatgttggg gtttattact gcatgcaagc tctacaaact    300
ccctggacgt tcggccaagg gaccaaggtg gaaatcaaac gaactgtggc tgcaccatct    360
gtcttcatct tcccgccatc tgatgagcag ttgaaatctg gaactgcctc tgttgtgtgc    420
ctgctgaata acttctatcc agagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagaggct    660
ctcgagcacc accaccacca ccactga                                         687
```

<210> SEQ ID NO 33
<211> LENGTH: 219
<212> TYPE: PRT
<213> ORGANISM: human

<400> SEQUENCE: 33

```
Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asn Gly Phe Asn Tyr Leu Asp Trp Tyr Leu Gln Lys Pro Gly Gln Ser
        35                  40                  45
Pro Gln Leu Leu Ile Tyr Leu Gly Ser Thr Arg Ala Ser Gly Val Pro
    50                  55                  60
Asp Arg Phe Ser Gly Ser Gly Ser Gly Thr Asp Phe Thr Leu Arg Ile
65                  70                  75                  80
Ser Arg Val Glu Ala Glu Asp Val Gly Val Tyr Phe Cys Met Gln Ala
                85                  90                  95
Val Gln Thr Pro Phe Thr Phe Gly Pro Gly Thr Arg Leu Asp Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215
```

<210> SEQ ID NO 34
<211> LENGTH: 657
<212> TYPE: DNA
<213> ORGANISM: human

<400> SEQUENCE: 34

```
gatattgtga tgactcagtc tccactctcc ctgcccgtca cccctggaga gccggcctcc    60
atctcctgca ggtctagtca gagcctcctg catagtaatg gattcaacta tttggattgg   120
tatctgcaga agccagggca gtctccacag ctcctgatct atttgggttc tactcgggcc   180
tccggggtcc ctgacaggtt cagtggcagt ggatcaggca cagattttac actgagaatc   240
agcagagtgg aggctgagga tgttggggtt tatttctgca tgcaagctgt ccaaactcct   300
ttcactttcg gccctgggac cagactggat atcaaacgaa ctgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct caacagggg agagtgt       657
```

<210> SEQ ID NO 35
<211> LENGTH: 112
<212> TYPE: PRT
<213> ORGANISM: human

<400> SEQUENCE: 35

```
Asp Ile Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Leu His Ser
            20                  25                  30

Asn Gly Phe Asn Tyr Leu Asp Trp Tyr Leu Gln Lys Pro Gly Gln Ser
        35                  40                  45

Pro Gln Leu Leu Ile Tyr Leu Gly Ser Thr Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Phe Cys Met Gln Ala
                85                  90                  95

Val Gln Thr Pro Phe Thr Phe Gly Pro Gly Thr Arg Leu Asp Ile Lys
            100                 105                 110
```

<210> SEQ ID NO 36
<211> LENGTH: 228
<212> TYPE: PRT
<213> ORGANISM: Artificial Sequence
<220> FEATURE:
<223> OTHER INFORMATION: Description of Artificial Sequence:Artificially
      Synthesized Seqence

<400> SEQUENCE: 36

```
Met Asp Ile Val Met Thr Gln Ser Pro Leu Ser Leu Pro Val Thr Pro
1               5                  10                  15

Gly Glu Pro Ala Ser Ile Ser Cys Arg Ser Ser Gln Ser Leu Leu His
            20                  25                  30

Ser Asn Gly Phe Asn Tyr Leu Asp Trp Tyr Leu Gln Lys Pro Gly Gln
        35                  40                  45
```

```
Ser Pro Gln Leu Leu Ile Tyr Leu Gly Ser Thr Arg Ala Ser Gly Val
    50                  55                  60
Pro Asp Arg Phe Ser Gly Ser Gly Ser Gly Thr Asp Phe Thr Leu Arg
 65                  70                  75                  80
Ile Ser Arg Val Glu Ala Glu Asp Val Gly Val Tyr Phe Cys Met Gln
                 85                  90                  95
Ala Val Gln Thr Pro Phe Thr Phe Gly Pro Gly Thr Arg Leu Asp Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Ala Leu Glu His His
    210                 215                 220
His His His His
225

<210> SEQ ID NO 37
<211> LENGTH: 687
<212> TYPE: DNA
<213> ORGANISM: Artificial Sequence
<220> FEATURE:
<223> OTHER INFORMATION: Description of Artificial Sequence:Artificially
      Synthesized Seqence

<400> SEQUENCE: 37
atggatattg tgatgactca gtctccactc tccctgcccg tcaccctgg agagccggcc      60 tccatctcct gcaggtctag tcagagcctc ctgcatagta atggattcaa ctatttggat    120
tggtatctgc agaagccagg gcagtctcca cagctcctga tctatttggg ttctactcgg    180
gcctccgggg tccctgacag gttcagtggc agtggatcag gcacagattt tacactgaga    240
atcagcagag tggaggctga ggatgttggg gtttatttct gcatgcaagc tgtccaaact    300
cctttcactt tcggccctgg gaccagactg gatatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc     600 gaagtcaccc atcagggcct gagctcgccc gtcacaaaga gcttcaacag gggagaggct    660
ctcgagcacc accaccacca ccactga                                        687

<210> SEQ ID NO 38
<211> LENGTH: 219
<212> TYPE: PRT
<213> ORGANISM: human

<400> SEQUENCE: 38
```

```
Asp Ile Val Met Thr Gln Thr Pro Leu Ser Pro Val Thr Leu Gly
  1               5                  10                 15
Gln Pro Ala Ser Ile Ser Cys Arg Ser Ser Gln Ser Leu Val His Ser
             20                  25                  30
Asp Gly Asn Thr Tyr Leu Ser Trp Leu Gln Gln Arg Pro Gly Gln Pro
         35                  40                  45
Pro Arg Leu Leu Ile Tyr Lys Ile Ser Asn Arg Phe Ser Gly Val Pro
     50                  55                  60
Asp Arg Phe Ser Gly Ser Gly Ala Gly Thr Asp Phe Thr Leu Lys Ile
 65                  70                  75                  80
Ser Arg Val Glu Ala Glu Asp Val Gly Ile Tyr Tyr Cys Met Gln Gly
                 85                  90                  95
Leu Gln Thr Pro Leu Thr Phe Gly Gly Gly Thr Lys Val Asp Leu Lys
             100                 105                 110
Arg Thr Val Ala Ala Pro Ser Val Phe Ile Phe Pro Pro Ser Asp Glu
         115                 120                 125
Gln Leu Lys Ser Gly Thr Ala Ser Val Val Cys Leu Leu Asn Asn Phe
     130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215
```

<210> SEQ ID NO 39
<211> LENGTH: 657
<212> TYPE: DNA
<213> ORGANISM: human

<400> SEQUENCE: 39

```
gatattgtga tgactcagac tccactctcc tcacctgtca cccttggaca gccggcctcc    60
atctcctgca ggtctagtca aagcctcgta cacagtgatg gaaacaccta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtgg aagctgagga tgtgggcatt tattactgca tgcagggtct acaaactcct   300
ctcacttcg gcggagggac caaggttgat ctcaaacgaa ctgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt      657
```

<210> SEQ ID NO 40
<211> LENGTH: 112
<212> TYPE: PRT
<213> ORGANISM: human

<400> SEQUENCE: 40

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Leu Gln Thr Pro Leu Thr Phe Gly Gly Gly Thr Lys Val Asp Leu Lys
            100                 105                 110

<210> SEQ ID NO 41
<211> LENGTH: 228
<212> TYPE: PRT
<213> ORGANISM: Artificial Sequence
<220> FEATURE:
<223> OTHER INFORMATION: Description of Artificial Sequence:Artificially
      Synthesized Seqence

<400> SEQUENCE: 41

Met Asp Ile Val Met Thr Gln Thr Pro Leu Ser Ser Pro Val Thr Leu
1               5                   10                  15

Gly Gln Pro Ala Ser Ile Ser Cys Arg Ser Ser Gln Ser Leu Val His
            20                  25                  30

Ser Asp Gly Asn Thr Tyr Leu Ser Trp Leu Gln Gln Arg Pro Gly Gln
        35                  40                  45

Pro Pro Arg Leu Leu Ile Tyr Lys Ile Ser Asn Arg Phe Ser Gly Val
50                  55                  60

Pro Asp Arg Phe Ser Gly Ser Gly Ala Gly Thr Asp Phe Thr Leu Lys
65                  70                  75                  80

Ile Ser Arg Val Glu Ala Glu Asp Val Gly Ile Tyr Tyr Cys Met Gln
                85                  90                  95

Gly Leu Gln Thr Pro Leu Thr Phe Gly Gly Gly Thr Lys Val Asp Leu
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Ala Leu Glu His His
    210                 215                 220

His His His His
225
```

<210> SEQ ID NO 42
<211> LENGTH: 687
<212> TYPE: DNA
<213> ORGANISM: Artificial Sequence
<220> FEATURE:
<223> OTHER INFORMATION: Description of Artificial Sequence:Artificially Synthesized Seqence

<400> SEQUENCE: 42

```
atggatattg tgatgactca gactccactc tcctcacctg tcaccttgg acagccggcc      60
tccatctcct gcaggtctag tcaaagcctc gtacacagtg atggaaacac ctacttgagt    120
tggcttcagc agaggccagg ccagcctcca agactcctaa tttataagat ttctaaccgg    180
ttctctgggg tcccagacag attcagtggc agtggggcag ggacagattt cacactgaaa    240
atcagcaggg tggaagctga ggatgtgggc atttattact gcatgcaggg tctacaaact    300
cctctcactt tcggcggagg gaccaaggtt gatctcaaac gaactgtggc tgcaccatct    360
gtcttcatct cccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600
gaagtcaccc atcagggcct gagctcgccc gtcacaaaga gcttcaacag gggagaggct    660
ctcgagcacc accaccacca ccactga                                        687
```

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:Artificially Synthesized DNA

<400> SEQUENCE: 43

```
agcttctggg gctgctaatg                                                  20
```

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:Artificially Synthesized DNA

<400> SEQUENCE: 44

```
agctcctggg gctgctaatg                                                  20
```

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence:Artificially Synthesized DNA

<400> SEQUENCE: 45

```
gatrttgtga tgacycag                                                    18
```

<210> SEQ ID NO 46
<211> LENGTH: 19
<212> TYPE: DNA
<213> ORGANISM: Artificial Sequence
<220> FEATURE:

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA

<400> SEQUENCE: 46
acactctccc ctgttgaag                                               19

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA

<400> SEQUENCE: 47
tcagctcctg gggctgctaa tgct                                         24

<210> SEQ ID NO 48
<211> LENGTH: 220
<212> TYPE: PRT
<213> ORGANISM: human

<400> SEQUENCE: 48

Asp Val Val Met Thr Gln Thr Pro Leu Ser Leu Ser Val Thr Pro Gly
1               5                   10                  15

Glu Pro Ala Ser Ile Ser Cys Arg Ser Thr Gln Ser Leu Leu Asp Ser
            20                  25                  30

Asp Gly Val Asn Pro Ser Phe Asp Trp Tyr Val Gln Lys Pro Gly Gln
        35                  40                  45

Ser Pro Gln Leu Leu Ile His Arg Gly Phe Tyr Arg Ala Ser Gly Val
    50                  55                  60

Pro Asp Arg Phe Ser Gly Ser Gly Ser Gly Thr Asp Phe Thr Leu Arg
65                  70                  75                  80

Ile Ser Arg Val Glu Ala Glu Asp Val Gly Val Tyr Tyr Cys Met Gln
                85                  90                  95

Arg Ile Glu Phe Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 49
<211> LENGTH: 660
<212> TYPE: DNA
<213> ORGANISM: human

<400> SEQUENCE: 49
gatgttgtga tgacccagac tccactctcc ctgtccgtca cccctggaga gccggcctcc    60

```
atctcctgca ggtctactca gagcctcttg gatagtgatg gtgtaaaccc ctctttcgac    120
tggtatgtac agaagccagg gcagtctcca caactcctga ttcatagagg tttctatcgg    180
gcctctggag tcccagacag gttcagtggc agtgggtcag gcactgattt cacactgagg    240
atcagcaggg tggaggctga ggatgttgga gtctattact gcatgcaacg catagagttt    300
cctctcactt tcggcggagg gaccaaggtg gagatcaagc gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaaact ctacgcctgc    600
gaagtcaccc atcagggcct gagctcgccc gtcacaaaga gcttcaacag gggagagtgt    660
```

<210> SEQ ID NO 50
<211> LENGTH: 113
<212> TYPE: PRT
<213> ORGANISM: human

<400> SEQUENCE: 50

```
Asp Val Val Met Thr Gln Thr Pro Leu Ser Leu Ser Val Thr Pro Gly
1               5                   10                  15

Glu Pro Ala Ser Ile Ser Cys Arg Ser Thr Gln Ser Leu Leu Asp Ser
            20                  25                  30

Asp Gly Val Asn Pro Ser Phe Asp Trp Tyr Val Gln Lys Pro Gly Gln
        35                  40                  45

Ser Pro Gln Leu Leu Ile His Arg Gly Phe Tyr Arg Ala Ser Gly Val
    50                  55                  60

Pro Asp Arg Phe Ser Gly Ser Gly Ser Gly Thr Asp Phe Thr Leu Arg
65                  70                  75                  80

Ile Ser Arg Val Glu Ala Glu Asp Val Gly Val Tyr Tyr Cys Met Gln
                85                  90                  95

Arg Ile Glu Phe Pro Leu Thr Phe Gly Gly Gly Thr Lys Val Glu Ile
            100                 105                 110

Lys
```

<210> SEQ ID NO 51
<211> LENGTH: 229
<212> TYPE: PRT
<213> ORGANISM: Artificial Sequence
<220> FEATURE:
<223> OTHER INFORMATION: Description of Artificial Sequence:Artificailly
      synthesized sequence

<400> SEQUENCE: 51

```
Met Asp Val Val Met Thr Gln Thr Pro Leu Ser Leu Ser Val Thr Pro
1               5                   10                  15

Gly Glu Pro Ala Ser Ile Ser Cys Arg Ser Thr Gln Ser Leu Leu Asp
            20                  25                  30

Ser Asp Gly Val Asn Pro Ser Phe Asp Trp Tyr Val Gln Lys Pro Gly
        35                  40                  45

Gln Ser Pro Gln Leu Leu Ile His Arg Gly Phe Tyr Arg Ala Ser Gly
    50                  55                  60

Val Pro Asp Arg Phe Ser Gly Ser Gly Ser Gly Thr Asp Phe Thr Leu
65                  70                  75                  80

Arg Ile Ser Arg Val Glu Ala Glu Asp Val Gly Val Tyr Tyr Cys Met
```

```
                        85                  90                  95
Gln Arg Ile Glu Phe Pro Leu Thr Phe Gly Gly Gly Thr Lys Val Glu
                100                 105                 110

Ile Lys Arg Thr Val Ala Ala Pro Ser Val Phe Ile Phe Pro Pro Ser
            115                 120                 125

Asp Glu Gln Leu Lys Ser Gly Thr Ala Ser Val Val Cys Leu Leu Asn
        130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Leu Tyr Ala Cys Glu Val Thr His Gln Gly Leu
        195                 200                 205

Ser Ser Pro Val Thr Lys Ser Phe Asn Arg Gly Glu Ala Leu Glu His
    210                 215                 220

His His His His His
225

<210> SEQ ID NO 52
<211> LENGTH: 219
<212> TYPE: PRT
<213> ORGANISM: human

<400> SEQUENCE: 52

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 53
<211> LENGTH: 660
<212> TYPE: DNA
<213> ORGANISM: human

<400> SEQUENCE: 53

```
atggatattg tgatgaccca gactccactc tctctgtccg tcaccctgg acagccggcc      60
tccatctcct gcaagtctag tcagagcctc ctgcatagtg atggaaagac ctatttgtat    120
tggtacctgc agaagccagg ccagtctcca cagctcctaa tctatgaagt ttccagccgg    180
ttctctggag tgccagatag gttcagtggc agcgggtcag ggacagattt cacactgaaa    240
atcagccggg tggaggctga ggatgttggg gtttattact gcatgcaagg tatacacctt    300
ccgtacactt ttggccaggg gaccaagctg gagatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaaact ctacgcctgc    600
gaagtcaccc atcagggcct gagctcgccc gtcacaaaga gcttcaacag gggagagtgt    660
```

<210> SEQ ID NO 54
<211> LENGTH: 112
<212> TYPE: PRT
<213> ORGANISM: human

<400> SEQUENCE: 54

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro Tyr Thr Phe Gly Gln Gly Thr Lys Leu Glu Ile Lys
            100                 105                 110
```

<210> SEQ ID NO 55
<211> LENGTH: 228
<212> TYPE: PRT
<213> ORGANISM: Artificial Sequence
<220> FEATURE:
<223> OTHER INFORMATION: Description of Artificial Sequence:Artificailly synthesized sequence

<400> SEQUENCE: 55

```
Met Asp Ile Val Met Thr Gln Thr Pro Leu Ser Leu Ser Val Thr Pro
1               5                   10                  15

Gly Gln Pro Ala Ser Ile Ser Cys Lys Ser Ser Gln Ser Leu Leu His
            20                  25                  30

Ser Asp Gly Lys Thr Tyr Leu Tyr Trp Tyr Leu Gln Lys Pro Gly Gln
        35                  40                  45
```

Ser Pro Gln Leu Leu Ile Tyr Glu Val Ser Ser Arg Phe Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Gly Ile His Leu Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Ala Leu Glu His His
210                 215                 220

His His His His
225

<210> SEQ ID NO 56
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 56
caccatgaac atccagatga cccag                                      25

<210> SEQ ID NO 57
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 57
caccatggac atccagatga cccag                                      25

<210> SEQ ID NO 58
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 58
caccatggac atccagttga cccag                                      25

<210> SEQ ID NO 59
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 59
caccatggcc atccagttga cccag							25

<210> SEQ ID NO 60
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 60
caccatggcc atccagatga cccag							25

<210> SEQ ID NO 61
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 61
caccatggcc atccggatga cccag							25

<210> SEQ ID NO 62
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 62
caccatggtc atctggatga cccag							25

<210> SEQ ID NO 63
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 63
caccatggac atccagatga tccag							25

<210> SEQ ID NO 64
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 64
caccatggat attgtgatga cccag							25

<210> SEQ ID NO 65
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 65
caccatggat attgtgatga ctcag							25

<210> SEQ ID NO 66

```
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 66
caccatggat gttgtgatga ctcag                                              25

<210> SEQ ID NO 67
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 67
caccatggag attgtgatga cccag                                              25

<210> SEQ ID NO 68
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 68
caccatggaa attgtgttga cacag                                              25

<210> SEQ ID NO 69
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 69
caccatggaa attgtgttga cgcag                                              25

<210> SEQ ID NO 70
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 70
caccatggaa atagtgatga cgcag                                              25

<210> SEQ ID NO 71
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 71
caccatggaa attgtaatga cacag                                              25

<210> SEQ ID NO 72
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 72
```
caccatggac atcgtgatga cccag                                              25

<210> SEQ ID NO 73
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 73
caccatggaa acgacactca cgcag                                              25

<210> SEQ ID NO 74
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 74
caccatggaa attgtgctga ctcag                                              25

<210> SEQ ID NO 75
<211> LENGTH: 25
<212> TYPE: DNA
<213> ORGANISM: Artificial Sequence
<220> FEATURE:
<223> OTHER INFORMATION: Artificially synthesized sequence

<400> SEQUENCE: 75
caccatggat gttgtgatga cacag                                              25

<210> SEQ ID NO 76
<211> LENGTH: 28
<212> TYPE: DNA
<213> ORGANISM: Artificial Sequence
<220> FEATURE:
<223> OTHER INFORMATION: Artificially synthesized sequence

<400> SEQUENCE: 76
acactctccc ctgttgaagc tctttgtg                                           28

<210> SEQ ID NO 77
<211> LENGTH: 111
<212> TYPE: PRT
<213> ORGANISM: Artificial Sequence
<220> FEATURE:
<223> OTHER INFORMATION: Artificially synthesized sequence

<400> SEQUENCE: 77

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly His Ser
        35                  40                  45

Pro His Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Asp Val Tyr Tyr Cys Met Gln
                85                  90                  95

Gly Leu His Leu Pro Gln Tyr Thr Phe Gly Gln Gly Thr Lys Leu
                100                 105                 110

<210> SEQ ID NO 78
<211> LENGTH: 220
<212> TYPE: PRT
<213> ORGANISM: Artificial Sequence
<220> FEATURE:
<223> OTHER INFORMATION: Artificially synthesized sequence

<400> SEQUENCE: 78

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Lys Pro Gly Gln Ala
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Trp Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 79
<211> LENGTH: 114
<212> TYPE: PRT
<213> ORGANISM: Artificial Sequence
<220> FEATURE:
<223> OTHER INFORMATION: Artificially synthesized sequence

<400> SEQUENCE: 79

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Met Gln Gly
            85                  90                  95

Ile His Leu Pro Pro Val His Phe Trp Pro Gly Asp Gln Ala Gly Asp
            100                 105                 110

Gln Thr

<210> SEQ ID NO 80
<211> LENGTH: 66
<212> TYPE: DNA
<213> ORGANISM: Artificial Sequence
<220> FEATURE:
<223> OTHER INFORMATION: Artificially synthesized sequence

<400> SEQUENCE: 80
gtcacaaaga gcttcaacag gggagagtgt ctcgagcacc accaccacca ccactgagat     60
ccggct                                                               66

<210> SEQ ID NO 81
<211> LENGTH: 66
<212> TYPE: DNA
<213> ORGANISM: Artificial Sequence
<220> FEATURE:
<223> OTHER INFORMATION: Artificially synthesized sequence

<400> SEQUENCE: 81
gtcacaaaga gcttcaacag gggagaggct ctcgagcacc accaccacca ccactgagat     60
ccggct                                                               66

<210> SEQ ID NO 82
<211> LENGTH: 229
<212> TYPE: PRT
<213> ORGANISM: Artificial Sequence
<220> FEATURE:
<223> OTHER INFORMATION: Artificially synthesized sequence

<400> SEQUENCE: 82

Met Asp Val Val Met Thr Gln Thr Pro Leu Ser Leu Ser Val Thr Pro
1               5                   10                  15

Gly Gln Pro Ala Ser Ile Ser Cys Lys Ser Ser Gln Ser Leu Leu His
            20                  25                  30

Ser Asp Gly Lys Thr Tyr Leu Tyr Trp Tyr Leu Gln Lys Pro Gly His
            35                  40                  45

Ser Pro His Leu Leu Ile Tyr Glu Val Ser Ser Arg Phe Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Leu His Leu Pro Gln Tyr Thr Phe Gly Gln Gly Thr Lys Leu Glu
            100                 105                 110

Ile Lys Arg Thr Val Ala Ala Pro Ser Val Phe Ile Phe Pro Pro Ser
            115                 120                 125

Asp Glu Gln Leu Lys Ser Gly Thr Ala Ser Val Val Cys Leu Leu Asn
        130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175
```

```
Asp Ser Thr Tyr Ser Leu Ser Ser Thr Leu Thr Leu Ser Lys Ala Asp
            180                 185                 190

Tyr Glu Lys His Lys Leu Tyr Ala Cys Glu Val Thr His Gln Gly Leu
        195                 200                 205

Ser Ser Pro Val Thr Lys Ser Phe Asn Arg Gly Glu Ala Leu Glu His
    210                 215                 220

His His His His His
225

<210> SEQ ID NO 83
<211> LENGTH: 228
<212> TYPE: PRT
<213> ORGANISM: Artificial Sequence
<220> FEATURE:
<223> OTHER INFORMATION: Artificially synthesized sequence

<400> SEQUENCE: 83

Met Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu Tyr
            20                  25                  30

Gly Asn Gly Asn Asn Tyr Leu Asp Trp Tyr Leu Gln Lys Pro Gly Gln
        35                  40                  45

Ser Pro Gln Leu Leu Ile Tyr Leu Gly Ser Ile Arg Ala Ser Gly Val
    50                  55                  60

Pro Asp Arg Phe Ser Gly Ser Gly Ser Gly Thr Asp Phe Gln Leu Lys
65                  70                  75                  80

Ile Ser Arg Val Glu Ala Asp Asp Val Gly Thr Tyr Tyr Cys Met Gln
                85                  90                  95

Ala Gln Gln Gly Pro Pro Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Ala Leu Glu His His
    210                 215                 220

His His His His
225

<210> SEQ ID NO 84
<211> LENGTH: 229
<212> TYPE: PRT
<213> ORGANISM: Artificial Sequence
<220> FEATURE:
<223> OTHER INFORMATION: Artificially synthesized sequence

<400> SEQUENCE: 84

Met Asp Val Val Met Thr Gln Thr Pro Leu Ser Leu Ser Val Thr Pro
```

```
1               5                   10                  15
Gly Glu Pro Ala Ser Ile Ser Cys Arg Ser Thr Gln Ser Leu Leu Asp
                20                  25                  30

Ser Asp Gly Val Asn Pro Ser Phe Asp Trp Tyr Val Gln Lys Pro Gly
            35                  40                  45

Gln Ser Pro Gln Leu Leu Ile His Arg Gly Phe Tyr Arg Ala Ser Gly
        50                  55                  60

Val Pro Asp Arg Phe Ser Gly Ser Gly Ser Gly Thr Asp Phe Thr Leu
65                  70                  75                  80

Arg Ile Ser Arg Val Glu Ala Glu Asp Val Gly Val Tyr Tyr Cys Met
                85                  90                  95

Gln Arg Ile Phe Phe Pro Leu Thr Phe Gly Gly Gly Thr Lys Val Glu
                100                 105                 110

Ile Lys Arg Thr Val Ala Ala Pro Ser Val Phe Ile Phe Pro Pro Ser
                115                 120                 125

Asp Glu Gln Leu Lys Ser Gly Thr Ala Ser Val Val Cys Leu Leu Asn
130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
                180                 185                 190

Tyr Glu Lys His Lys Leu Tyr Ala Cys Glu Val Thr His Gln Gly Leu
                195                 200                 205

Ser Ser Pro Val Thr Lys Ser Phe Asn Arg Gly Glu Ala Leu Glu His
                210                 215                 220

His His His His His
225

<210> SEQ ID NO 85
<211> LENGTH: 228
<212> TYPE: PRT
<213> ORGANISM: Artificial Sequence
<220> FEATURE:
<223> OTHER INFORMATION: Artificially synthesized sequence

<400> SEQUENCE: 85

Met Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
                20                  25                  30

Ser Asn Gly Tyr Asn Tyr Leu Asp Trp Tyr Leu Gln Lys Pro Gly Gln
            35                  40                  45

Ser Pro Gln Leu Leu Ile Tyr Leu Gly Ser Asn Arg Ala Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Thr Arg Phe Thr Phe Gly Pro Gly Thr Lys Val Asp Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
```

```
                130                 135                 140
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Leu Tyr Ala Cys Glu Val Thr His Gln Gly Leu Ser
                195                 200                 205

Ser Pro Val Thr Lys Ser Phe Asn Arg Gly Glu Ala Leu Glu His His
                210                 215                 220

His His His His
225

<210> SEQ ID NO 86
<211> LENGTH: 228
<212> TYPE: PRT
<213> ORGANISM: Artificial Sequence
<220> FEATURE:
<223> OTHER INFORMATION: Artificially synthesized sequence

<400> SEQUENCE: 86

Met Asp Val Val Met Thr Gln Thr Pro Leu Ser Leu Ser Val Thr Pro
1               5                   10                  15

Gly Gln Pro Ala Ser Leu Ser Cys Lys Ser Ser Gln Ser Leu Leu His
                20                  25                  30

Ser Asp Gly Lys Thr Tyr Leu Tyr Trp Tyr Leu Gln Lys Pro Gly Gln
                35                  40                  45

Ser Pro Gln Leu Leu Ile Tyr Glu Val Ser Ser Arg Phe Ser Gly Val
                50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Glu
                85                  90                  95

Gly Thr His Leu Pro Trp Thr Phe Gly Gln Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
                130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Leu Tyr Ala Cys Glu Val Thr His Gln Gly Leu Ser
                195                 200                 205

Ser Pro Val Thr Lys Ser Phe Asn Arg Gly Glu Ala Leu Glu His His
                210                 215                 220

His His His His
225

<210> SEQ ID NO 87
<211> LENGTH: 228
<212> TYPE: PRT
```

<213> ORGANISM: Artificial Sequence
<220> FEATURE:
<223> OTHER INFORMATION: Artificially synthesized sequence

<400> SEQUENCE: 87

Met Asp Val Val Met Thr Gln Thr Pro Leu Ser Leu Ser Val Thr Pro
1               5                   10                  15

Gly Gln Pro Ala Ser Ile Ser Cys Lys Ser Ser Gln Ser Leu Leu His
            20                  25                  30

Ser Asp Gly Lys Thr Tyr Leu Tyr Trp Tyr Leu Gln Lys Pro Gly Gln
        35                  40                  45

Ser Pro Gln Leu Leu Ile Tyr Glu Val Ser Ser Arg Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Ile His Leu Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Ala Leu Glu His His
    210                 215                 220

His His His His
225

<210> SEQ ID NO 88
<211> LENGTH: 228
<212> TYPE: PRT
<213> ORGANISM: Artificial Sequence
<220> FEATURE:
<223> OTHER INFORMATION: Artificially synthesized sequence

<400> SEQUENCE: 88

Met Asp Val Val Met Thr Gln Thr Pro Leu Ser Leu Ser Val Thr Pro
1               5                   10                  15

Gly Gln Pro Ala Ser Ile Ser Cys Lys Ser Ser Gln Ser Leu Leu His
            20                  25                  30

Ser Asp Gly Lys Thr Tyr Phe Tyr Trp Tyr Leu Gln Arg Pro Gly Arg
        35                  40                  45

Ser Pro Gln Leu Leu Ile Gln Glu Val Ser Arg Arg Phe Ser Gly Val
    50                  55                  60

Pro Asp Arg Phe Ser Gly Ser Gly Ser Gly Ser Asp Phe Thr Leu Lys
65                  70                  75                  80

Ile Ser Arg Val Glu Ala Glu Asp Val Gly Val Tyr Tyr Cys Met Gln
                85                  90                  95

```
Gly Thr Tyr Val Pro His Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Ala Leu Glu His His
            210                 215                 220

His His His His
225

<210> SEQ ID NO 89
<211> LENGTH: 228
<212> TYPE: PRT
<213> ORGANISM: Artificial Sequence
<220> FEATURE:
<223> OTHER INFORMATION: Artificially synthesized sequence

<400> SEQUENCE: 89

Met Asp Ile Val Met Thr Gln Thr Pro Leu Ser Leu Ser Val Thr Pro
1               5                   10                  15

Gly Gln Pro Ala Ser Ile Ser Cys Lys Ser Ser Gln Ser Leu Leu His
            20                  25                  30

Ser Asp Gly Lys Thr Tyr Leu Tyr Trp Tyr Leu Gln Lys Pro Gly Gln
        35                  40                  45

Ser Pro Gln Leu Leu Ile Tyr Glu Val Ser Ser Arg Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Ile His Leu Pro Tyr Thr Phe Gly Gln Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Ala Leu Glu His His
            210                 215                 220
```

His His His His
225

<210> SEQ ID NO 90
<211> LENGTH: 227
<212> TYPE: PRT
<213> ORGANISM: Artificial Sequence
<220> FEATURE:
<223> OTHER INFORMATION: Artificially synthesized sequence

<400> SEQUENCE: 90

Met Asp Val Val Met Thr Gln Ser Pro Leu Ser Leu Pro Val Thr Pro
1               5                   10                  15

Gly Glu Pro Ala Ser Ile Ser Cys Leu Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Arg Gly Ser Asn Arg Ala Ser Gly Val
    50                  55                  60

Pro Asp Arg Phe Ser Gly Ser Ala Ser Gly Thr Asp Phe Thr Leu Lys
65                  70                  75                  80

Ile Ser Lys Val Glu Ala Glu Asp Val Gly Val Tyr Tyr Cys Met Gln
                85                  90                  95

Gly Leu Ser Thr Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Ala Leu Glu His His His
    210                 215                 220

His His His
225

<210> SEQ ID NO 91
<211> LENGTH: 229
<212> TYPE: PRT
<213> ORGANISM: Artificial Sequence
<220> FEATURE:
<223> OTHER INFORMATION: Artificially synthesized sequence

<400> SEQUENCE: 91

Met Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Thr Pro Pro Trp Thr Phe Gly Gln Gly Thr Lys Val Glu
            100                 105                 110

Ile Lys Arg Thr Val Ala Ala Pro Ser Val Phe Ile Phe Pro Pro Ser
            115                 120                 125

Asp Glu Gln Leu Lys Ser Gly Thr Ala Ser Val Val Cys Leu Leu Asn
130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Leu Tyr Ala Cys Glu Val Thr His Gln Gly Leu
            195                 200                 205

Ser Ser Pro Val Thr Lys Ser Phe Asn Arg Gly Glu Ala Leu Glu His
    210                 215                 220

His His His His His
225

<210> SEQ ID NO 92
<211> LENGTH: 228
<212> TYPE: PRT
<213> ORGANISM: Artificial Sequence
<220> FEATURE:
<223> OTHER INFORMATION: Artificially synthesized sequence

<400> SEQUENCE: 92

Met Asp Ile Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
                20                  25                  30

Ser Asn Gly Tyr Asn Tyr Leu Asp Trp Tyr Leu Gln Lys Pro Gly Gln
            35                  40                  45

Ser Pro Gln Leu Leu Ile Tyr Leu Gly Ser Asn Arg Ala Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Thr Pro Arg Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

```
Glu Lys His Lys Leu Tyr Ala Cys Glu Val Thr His Gln Gly Leu Ser
        195                 200                 205

Ser Pro Val Thr Lys Ser Phe Asn Arg Gly Glu Ala Leu Glu His His
    210                 215                 220

His His His His
225

<210> SEQ ID NO 93
<211> LENGTH: 229
<212> TYPE: PRT
<213> ORGANISM: Artificial Sequence
<220> FEATURE:
<223> OTHER INFORMATION: Artificially synthesized sequence

<400> SEQUENCE: 93

Met Asp Val Val Met Thr Gln Ser Pro Leu Ser Leu Pro Val Thr Pro
1               5                   10                  15

Gly Glu Ala Ala Ser Ile Ser Cys Arg Ser Ser Gln Ser Leu Leu His
            20                  25                  30

Asn Asn Gly Tyr Thr Tyr Leu Tyr Trp Phe Leu Gln Lys Ala Arg Pro
        35                  40                  45

Val Ser Thr Leu Leu Ile Tyr Glu Val Ser Asn Arg Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Phe Gly Val Tyr Tyr Cys Met Gln
                85                  90                  95

Asp Ala Gln Asp Pro Pro Ile Thr Phe Gly Gln Gly Thr Arg Leu Glu
            100                 105                 110

Ile Lys Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Leu Tyr Ala Cys Glu Val Thr His Gln Gly Leu
        195                 200                 205

Ser Ser Pro Val Thr Lys Ser Phe Asn Arg Gly Glu Ala Leu Glu His
    210                 215                 220

His His His His His
225

<210> SEQ ID NO 94
<211> LENGTH: 228
<212> TYPE: PRT
<213> ORGANISM: Artificial Sequence
<220> FEATURE:
<223> OTHER INFORMATION: Artificially synthesized sequence

<400> SEQUENCE: 94

Met Asp Ile Val Met Thr Gln Ser Pro Leu Ser Leu Pro Val Thr Leu
1               5                   10                  15

Gly Gln Pro Ala Ser Ile Ser Cys Arg Ser Ser Gln Ser Leu Val Lys
```

```
              20                  25                  30
Ser Asp Gly Asn Thr Tyr Leu Ser Trp Phe Gln Gln Arg Pro Gly Gln
           35                  40                  45

Ala Pro Arg Leu Phe Tyr Arg Val Ser Trp Arg Asp Ser Gly Val
 50                  55                  60

Pro Asp Arg Phe Arg Gly Ser Gly Ser Gly Thr Asp Phe Thr Leu Glu
 65                  70                  75                  80

Ile Ser Arg Val Glu Ala Glu Asp Val Gly Ile Tyr Tyr Cys Met Gln
                 85                  90                  95

Ala Leu Gln Thr Pro Pro Thr Phe Gly Gly Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Ala Leu Glu His His
    210                 215                 220

His His His His
225

<210> SEQ ID NO 95
<211> LENGTH: 66
<212> TYPE: DNA
<213> ORGANISM: Homo sapiens

<400> SEQUENCE: 95
atggacatga gggtccccgc tcagctcctg gggctcctgc tgctctggct cccaggtgcc      60
aaatgt                                                                66

<210> SEQ ID NO 96
<211> LENGTH: 66
<212> TYPE: DNA
<213> ORGANISM: Homo sapiens

<400> SEQUENCE: 96
atggacatga gggtccccgc tcagctcctg gggctcctgc tgctctggct cccaggtgcc      60
agatgt                                                                66

<210> SEQ ID NO 97
<211> LENGTH: 60
<212> TYPE: DNA
<213> ORGANISM: Homo sapiens

<400> SEQUENCE: 97
atgagggtcc ccgctcagct cctggggctc ctgctgctct ggctcccagg tgccagatgt      60

<210> SEQ ID NO 98
<211> LENGTH: 66
<212> TYPE: DNA
```

```
<213> ORGANISM: Homo sapiens

<400> SEQUENCE: 98
atggacatga gggtccccgc tcagctcctg gggctcctgc tgctctggtt cccaggttcc    60
agatgc                                                              66

<210> SEQ ID NO 99
<211> LENGTH: 66
<212> TYPE: DNA
<213> ORGANISM: Homo sapiens

<400> SEQUENCE: 99
atggacatga tggtccccgc tcagctcctg gggctcctgc tgctctggtt cccaggttcc    60
agatgc                                                              66

<210> SEQ ID NO 100
<211> LENGTH: 66
<212> TYPE: DNA
<213> ORGANISM: Homo sapiens

<400> SEQUENCE: 100
atggacatga gggtccccgc tcagcttctg gggctcctgc tgctctggct cccaggtgcc    60
agatgt                                                              66

<210> SEQ ID NO 101
<211> LENGTH: 66
<212> TYPE: DNA
<213> ORGANISM: Homo sapiens

<400> SEQUENCE: 101
atggacatga gggtccccgc tcagctcctg gggctcctgc tgctctgttt cccaggtgcc    60
agatgt                                                              66

<210> SEQ ID NO 102
<211> LENGTH: 66
<212> TYPE: DNA
<213> ORGANISM: Homo sapiens

<400> SEQUENCE: 102
atggacatga gggtccccgc tcagctcctg gggctcctgc tgctctggtt cccaggtgcc    60
agatgt                                                              66

<210> SEQ ID NO 103
<211> LENGTH: 66
<212> TYPE: DNA
<213> ORGANISM: Homo sapiens

<400> SEQUENCE: 103
atggacatga gggtccctgc tcagctcctg gggctcctgc tgctctggct cccagatacc    60
agatgt                                                              66

<210> SEQ ID NO 104
<211> LENGTH: 66
<212> TYPE: DNA
<213> ORGANISM: Homo sapiens

<400> SEQUENCE: 104
atggacatga gggtccctgc tcagctcctg gggctcctgc agctctggct ctcaggtgcc    60
agatgt                                                              66
```

<210> SEQ ID NO 105
<211> LENGTH: 66
<212> TYPE: DNA
<213> ORGANISM: Homo sapiens

<400> SEQUENCE: 105
atggacatga gggtccccgc tcagctcctg gggctcctgc tactctggct ccgaggtgcc    60
agatgt    66

<210> SEQ ID NO 106
<211> LENGTH: 66
<212> TYPE: DNA
<213> ORGANISM: Homo sapiens

<400> SEQUENCE: 106
atggacatga gggtccccgc tcagctcctg gggctcctgc tgctctgggt cccaggtgcc    60
agatgt    66

<210> SEQ ID NO 107
<211> LENGTH: 66
<212> TYPE: DNA
<213> ORGANISM: Homo sapiens

<400> SEQUENCE: 107
atggacatga gggtccctgc tcagctcctg gggctcctgc tgctctggct ctcaggtgcc    60
agatgt    66

<210> SEQ ID NO 108
<211> LENGTH: 66
<212> TYPE: DNA
<213> ORGANISM: Homo sapiens

<400> SEQUENCE: 108
atggacatga gggtccccgc tcagctcctg gggctcctgc tgctctggct cccaggtgtc    60
agattt    66

<210> SEQ ID NO 109
<211> LENGTH: 66
<212> TYPE: DNA
<213> ORGANISM: Homo sapiens

<400> SEQUENCE: 109
atggacatga gggtgcccgc tcagcgcctg gggctcctgc tgctctggtt cccaggtgcc    60
agatgt    66

<210> SEQ ID NO 110
<211> LENGTH: 60
<212> TYPE: DNA
<213> ORGANISM: Homo sapiens

<400> SEQUENCE: 110
atgaggctcc ttgctcagct tctggggctg ctaatgctct gggtccctgg taccagtggg    60

<210> SEQ ID NO 111
<211> LENGTH: 60
<212> TYPE: DNA
<213> ORGANISM: Homo sapiens

<400> SEQUENCE: 111
atgaggctcc ctgctcagct cctggggctg ctaatgctct gggtctctgg taccagtggg    60

<210> SEQ ID NO 112
<211> LENGTH: 60
<212> TYPE: DNA
<213> ORGANISM: Homo sapiens

<400> SEQUENCE: 112
atgaggctcc ctgctcagct cctggggctg ctaatgctct ggatccctgg taccagtgcg    60

<210> SEQ ID NO 113
<211> LENGTH: 60
<212> TYPE: DNA
<213> ORGANISM: Homo sapiens

<400> SEQUENCE: 113
atgaggctcc ctgctcagct cctggggctg ctaatgctct gggtcccagg taccagtggg    60

<210> SEQ ID NO 114
<211> LENGTH: 60
<212> TYPE: DNA
<213> ORGANISM: Homo sapiens

<400> SEQUENCE: 114
atgaggctcc ctgctcagct cctggggctg ctaatgctct gggtccctgg taccagtgag    60

<210> SEQ ID NO 115
<211> LENGTH: 60
<212> TYPE: DNA
<213> ORGANISM: Homo sapiens

<400> SEQUENCE: 115
atgaggctcc ctgctcagct cctggggctg ctaatgctct ggataccTGG taccagtgca    60

<210> SEQ ID NO 116
<211> LENGTH: 60
<212> TYPE: DNA
<213> ORGANISM: Homo sapiens

<400> SEQUENCE: 116
atggaagccc cagctcagct tctcttcctc ctgctactct ggctcccaga taccaccaga    60

<210> SEQ ID NO 117
<211> LENGTH: 60
<212> TYPE: DNA
<213> ORGANISM: Homo sapiens

<400> SEQUENCE: 117
atggaagccc cagcgcagct tctcttcctc ctgctactct ggctcccaga taccaccaga    60

<210> SEQ ID NO 118
<211> LENGTH: 60
<212> TYPE: DNA
<213> ORGANISM: Homo sapiens

<400> SEQUENCE: 118
atggaagccc cagctcagct tctcttcctc ctgctactct ggctcccaga taccaccgga    60

<210> SEQ ID NO 119
<211> LENGTH: 60
<212> TYPE: DNA
<213> ORGANISM: Homo sapiens

<400> SEQUENCE: 119

```
atggaagccc cagcgcagct tctcttcctc ctgctactct ggctcccaga taccactgga    60
```

<210> SEQ ID NO 120
<211> LENGTH: 60
<212> TYPE: DNA
<213> ORGANISM: Homo sapiens

<400> SEQUENCE: 120

```
atggaaaccc cagcgcagct tctcttcctc ctgctactct ggctcccaga taccaccgga    60
```

<210> SEQ ID NO 121
<211> LENGTH: 69
<212> TYPE: DNA
<213> ORGANISM: Homo sapiens

<400> SEQUENCE: 121

```
atggaaccat ggaagcccca gcacagcttc ttcttcctcc tgctactctg gctcccagat    60
accaccgga                                                            69
```

<210> SEQ ID NO 122
<211> LENGTH: 60
<212> TYPE: DNA
<213> ORGANISM: Homo sapiens

<400> SEQUENCE: 122

```
atggaagccc cagcgcagct tctcttcctc ctgctactct ggctcacaga taccaccgga    60
```

<210> SEQ ID NO 123
<211> LENGTH: 60
<212> TYPE: DNA
<213> ORGANISM: Homo sapiens

<400> SEQUENCE: 123

```
atggaagccc cagcgcagct tctcttcctc ctgctactct ggctcccaga taccaccgga    60
```

<210> SEQ ID NO 124
<211> LENGTH: 24
<212> TYPE: DNA
<213> ORGANISM: Homo sapiens

<400> SEQUENCE: 124

```
acctcctgct actctggctc ccag                                           24
```

<210> SEQ ID NO 125
<211> LENGTH: 60
<212> TYPE: DNA
<213> ORGANISM: Homo sapiens

<400> SEQUENCE: 125

```
atggtgttgc agacccaggt cttcatttct ctgttgctct ggatctcgtg tgcctacggg    60
```

<210> SEQ ID NO 126
<211> LENGTH: 60
<212> TYPE: DNA
<213> ORGANISM: Homo sapiens

<400> SEQUENCE: 126

```
atggggtccc aggttcacct cctcagcttc ctcctccttt ggatctctga taccagggca    60
```

<210> SEQ ID NO 127
<211> LENGTH: 57
<212> TYPE: DNA

<213> ORGANISM: Homo sapiens

<400> SEQUENCE: 127
atgttgccat cacaactcat tgggtttctg ctgctctggg ttccagcctc caggggt    57

<210> SEQ ID NO 128
<211> LENGTH: 60
<212> TYPE: DNA
<213> ORGANISM: Homo sapiens

<400> SEQUENCE: 128
atggtgtccc cgttgcaatt cctgcggctt ctgctcctct gggttccagc ctccaggggt    60

<210> SEQ ID NO 129
<211> LENGTH: 20
<212> TYPE: DNA
<213> ORGANISM: Artificial Sequence
<220> FEATURE:
<223> OTHER INFORMATION: Artificially synthesized sequence

<400> SEQUENCE: 129
agctcctggg gctcctgctg    20

<210> SEQ ID NO 130
<211> LENGTH: 20
<212> TYPE: DNA
<213> ORGANISM: Artificial Sequence
<220> FEATURE:
<223> OTHER INFORMATION: Artificially synthesized sequence

<400> SEQUENCE: 130
ttctcttcct cctgctactc    20

<210> SEQ ID NO 131
<211> LENGTH: 20
<212> TYPE: DNA
<213> ORGANISM: Artificial Sequence
<220> FEATURE:
<223> OTHER INFORMATION: Artificially synthesized sequence

<400> SEQUENCE: 131
tcatttctct gttgctctgg    20

<210> SEQ ID NO 132
<211> LENGTH: 20
<212> TYPE: DNA
<213> ORGANISM: Artificial Sequence
<220> FEATURE:
<223> OTHER INFORMATION: Artificially synthesized sequence

<400> SEQUENCE: 132
tcctcagctt cctcctcctt    20

<210> SEQ ID NO 133
<211> LENGTH: 20
<212> TYPE: DNA
<213> ORGANISM: Artificial Sequence
<220> FEATURE:
<223> OTHER INFORMATION: Artificially synthesized sequence

<400> SEQUENCE: 133
ggtttctgct gctctgggtt    20

<210> SEQ ID NO 134
<211> LENGTH: 72

```
<212> TYPE: DNA
<213> ORGANISM: Homo sapiens

<400> SEQUENCE: 134
gacatccaga tgacccagtc tccttccacc ctgtctgcat ctgtaagaga cagagtcacc    60
atcacttgcc gg                                                        72

<210> SEQ ID NO 135
<211> LENGTH: 72
<212> TYPE: DNA
<213> ORGANISM: Homo sapiens

<400> SEQUENCE: 135
gacatccaga tgacccagtc tccttccacc ctgtctgcat ctgtaagaga cagagtcacc    60
atcatttgcc gg                                                        72

<210> SEQ ID NO 136
<211> LENGTH: 72
<212> TYPE: DNA
<213> ORGANISM: Homo sapiens

<400> SEQUENCE: 136
gccatccaga tgacccagtc tccatcctcc ctgtctgcat ctgtaagaga cagagtcacc    60
atcacttgcc gg                                                        72

<210> SEQ ID NO 137
<211> LENGTH: 72
<212> TYPE: DNA
<213> ORGANISM: Homo sapiens

<400> SEQUENCE: 137
gccatccgga tgacccagtc tccatcctca ttctctgcat ctgtaagaga cagagtcacc    60
atcacttgtc gg                                                        72

<210> SEQ ID NO 138
<211> LENGTH: 72
<212> TYPE: DNA
<213> ORGANISM: Homo sapiens

<400> SEQUENCE: 138
gacatccagt tgacccagtc tccatccttc ctgtctgcat ctgtaagaga cagagtcacc    60
atcacttgcc gg                                                        72

<210> SEQ ID NO 139
<211> LENGTH: 72
<212> TYPE: DNA
<213> ORGANISM: Homo sapiens

<400> SEQUENCE: 139
gacatccaga tgacccagtc tccatcttcc gtgtctgcat ctgtaagaga cagagtcacc    60
atcacttgtc gg                                                        72

<210> SEQ ID NO 140
<211> LENGTH: 72
<212> TYPE: DNA
<213> ORGANISM: Homo sapiens

<400> SEQUENCE: 140
gccatccagt tgacccagtc tccatcctcc ctgtctgcat ctgtaagaga cagagtcacc    60
```

```
atcacttgcc gg                                                             72

<210> SEQ ID NO 141
<211> LENGTH: 71
<212> TYPE: DNA
<213> ORGANISM: Homo sapiens

<400> SEQUENCE: 141
gacatccaga tgacccagtc tccatcctca ctgtctgcat ctgtaagaga cagagtcacc         60
atcacttgtc g                                                             71

<210> SEQ ID NO 142
<211> LENGTH: 71
<212> TYPE: DNA
<213> ORGANISM: Homo sapiens

<400> SEQUENCE: 142
gacatccaga tgacccagtc tccatcctcc ctgtctgcat ctgtaagaga cagagtcacc         60
atcacttgcc g                                                             71

<210> SEQ ID NO 143
<211> LENGTH: 72
<212> TYPE: DNA
<213> ORGANISM: Homo sapiens

<400> SEQUENCE: 143
gacatccaga tgacccagtc tccatcctcc ctgtctgcat ctgtaagaga cagagtcacc         60
atcacttgcc gg                                                            72

<210> SEQ ID NO 144
<211> LENGTH: 72
<212> TYPE: DNA
<213> ORGANISM: Homo sapiens

<400> SEQUENCE: 144
gacatccagt tgacccagtc tccatcctcc ctgtctgcat ctgtaagaga cagagtcacc         60
atcacttgcc gg                                                            72

<210> SEQ ID NO 145
<211> LENGTH: 72
<212> TYPE: DNA
<213> ORGANISM: Homo sapiens

<400> SEQUENCE: 145
gtcatctgga tgacccagtc tccatcctta ctctctgcat ctataagaga cagagtcacc         60
atcagttgtc gg                                                            72

<210> SEQ ID NO 146
<211> LENGTH: 72
<212> TYPE: DNA
<213> ORGANISM: Homo sapiens

<400> SEQUENCE: 146
gacatccaga tgacccagtc tccatcttct gtgtctgcat ctgtaagaga cagagtcacc         60
atcacttgtc gg                                                            72

<210> SEQ ID NO 147
<211> LENGTH: 72
<212> TYPE: DNA
<213> ORGANISM: Homo sapiens
```

<400> SEQUENCE: 147
gacatccaga tgacccagtc tccatcctca ctgtctgcat ctgtaagaga cagagtcacc    60
atcacttgtc gg    72

<210> SEQ ID NO 148
<211> LENGTH: 72
<212> TYPE: DNA
<213> ORGANISM: Homo sapiens

<400> SEQUENCE: 148
gacatccaga tgacccagtc tccatctgcc atgtctgcat ctgtaagaga cagagtcacc    60
atcacttgtc gg    72

<210> SEQ ID NO 149
<211> LENGTH: 72
<212> TYPE: DNA
<213> ORGANISM: Homo sapiens

<400> SEQUENCE: 149
gacatccaga tgacccagtc tccatcctcc ctgtctgcat ctgtaagaga cagagtcacc    60
atcacttgcc ag    72

<210> SEQ ID NO 150
<211> LENGTH: 72
<212> TYPE: DNA
<213> ORGANISM: Homo sapiens

<400> SEQUENCE: 150
gacatccaga tgatccagtc tccatctttc ctgtctgcat ctgtaagaga cagagtcagt    60
atcatttgct gg    72

<210> SEQ ID NO 151
<211> LENGTH: 72
<212> TYPE: DNA
<213> ORGANISM: Homo sapiens

<400> SEQUENCE: 151
gccatccgga tgacccagtc tccattctcc ctgtctgcat ctgtaagaga cagagtcacc    60
atcacttgct gg    72

<210> SEQ ID NO 152
<211> LENGTH: 72
<212> TYPE: DNA
<213> ORGANISM: Homo sapiens

<400> SEQUENCE: 152
gatattgtga tgacccagac tccactctcc tcacctgtca cccttggaca gccggcctcc    60
atctcctgca gg    72

<210> SEQ ID NO 153
<211> LENGTH: 72
<212> TYPE: DNA
<213> ORGANISM: Homo sapiens

<400> SEQUENCE: 153
gatattgtga tgactcagtc tccactctcc ctgcccgtca cccctggaga gccggcctcc    60
atctcctgca gg    72

```
<210> SEQ ID NO 154
<211> LENGTH: 72
<212> TYPE: DNA
<213> ORGANISM: Homo sapiens

<400> SEQUENCE: 154
gatattgtga tgacccagac tccactctct ctgtccgtca cccctggaca gccggcctcc    60
atctcctgca ag                                                       72

<210> SEQ ID NO 155
<211> LENGTH: 72
<212> TYPE: DNA
<213> ORGANISM: Homo sapiens

<400> SEQUENCE: 155
gatgttgtga tgactcagtc tccactctcc ctgcccgtca cccttggaca gccggcctcc    60
atctcctgca gg                                                       72

<210> SEQ ID NO 156
<211> LENGTH: 72
<212> TYPE: DNA
<213> ORGANISM: Homo sapiens

<400> SEQUENCE: 156
gatattgtga tgacccagac tccactctcc ctgcccgtca cccctggaga gccggcctcc    60
atctcctgca gg                                                       72

<210> SEQ ID NO 157
<211> LENGTH: 72
<212> TYPE: DNA
<213> ORGANISM: Homo sapiens

<400> SEQUENCE: 157
gatattgtga tgacccagac tccactctcc tcgcctgtca cccttggaga gccggcctcc    60
atctccttca gg                                                       72

<210> SEQ ID NO 158
<211> LENGTH: 72
<212> TYPE: DNA
<213> ORGANISM: Homo sapiens

<400> SEQUENCE: 158
gagattgtga tgacccagac tccactctcc ttgtctatca cccttggaga gcaggcctcc    60
atgtccttca gg                                                       72

<210> SEQ ID NO 159
<211> LENGTH: 72
<212> TYPE: DNA
<213> ORGANISM: Homo sapiens

<400> SEQUENCE: 159
gaaattgtaa tgacacagtc tccacccacc ctgtctttgt ctccagggga aagagtcacc    60
ctctcctgca gg                                                       72

<210> SEQ ID NO 160
<211> LENGTH: 72
<212> TYPE: DNA
<213> ORGANISM: Homo sapiens

<400> SEQUENCE: 160
```

```
gaaattgtgt tgacacagtc tccagccacc ctgtctttgt ctccagggga aagagccacc    60
ctctcctgca gg                                                       72
```

<210> SEQ ID NO 161
<211> LENGTH: 72
<212> TYPE: DNA
<213> ORGANISM: Homo sapiens

<400> SEQUENCE: 161

```
gaaatagtga tgacgcagtc tccagccacc ctgtctgtgt ctccagggga aagagccacc    60
ctctcctgca gg                                                       72
```

<210> SEQ ID NO 162
<211> LENGTH: 72
<212> TYPE: DNA
<213> ORGANISM: Homo sapiens

<400> SEQUENCE: 162

```
gaaattgtgt tgacgcagtc tccaggcacc ctgtctttgt ctccagggga aagagccacc    60
ctctcctgca gg                                                       72
```

<210> SEQ ID NO 163
<211> LENGTH: 72
<212> TYPE: DNA
<213> ORGANISM: Homo sapiens

<400> SEQUENCE: 163

```
gaaattgtaa tgacacagtc tccagccacc ctgtctttgt ctccagggga aagagccacc    60
ctctcctgca gg                                                       72
```

<210> SEQ ID NO 164
<211> LENGTH: 72
<212> TYPE: DNA
<213> ORGANISM: Homo sapiens

<400> SEQUENCE: 164

```
gaaattgtgt tgacgcagtc tccagccacc ctgtctttgt ctccagggga aagagccacc    60
ctctcctgca gg                                                       72
```

<210> SEQ ID NO 165
<211> LENGTH: 72
<212> TYPE: DNA
<213> ORGANISM: Homo sapiens

<400> SEQUENCE: 165

```
gaaattgtgt tgacacagtc tccaggcacc ctgtctttgt ctccagggga aagagccacc    60
ctctcctgca gg                                                       72
```

<210> SEQ ID NO 166
<211> LENGTH: 72
<212> TYPE: DNA
<213> ORGANISM: Homo sapiens

<400> SEQUENCE: 166

```
gacatcgtga tgacccagtc tccagactcc ctggctgtgt ctctgggcga gagggccacc    60
atcaactgca ag                                                       72
```

<210> SEQ ID NO 167

```
<211> LENGTH: 72
<212> TYPE: DNA
<213> ORGANISM: Homo sapiens

<400> SEQUENCE: 167
gaaacgacac tcacgcagtc tccagcattc atgtcagcga ctccaggaga caaagtcaac    60
atctcctgca aa                                                         72

<210> SEQ ID NO 168
<211> LENGTH: 72
<212> TYPE: DNA
<213> ORGANISM: Homo sapiens

<400> SEQUENCE: 168
gaaattgtgc tgactcagtc tccagactttt cagtctgtga ctccaaagga gaaagtcacc    60
atcacctgcc gg                                                         72

<210> SEQ ID NO 169
<211> LENGTH: 72
<212> TYPE: DNA
<213> ORGANISM: Homo sapiens

<400> SEQUENCE: 169
gatgttgtga tgacacagtc tccagctttc ctctctgtga ctccagggga gaaagtcacc    60
atcacctgcc ag                                                         72

<210> SEQ ID NO 170
<211> LENGTH: 18
<212> TYPE: DNA
<213> ORGANISM: Artificial Sequence
<220> FEATURE:
<223> OTHER INFORMATION: Artificially synthesized sequence

<400> SEQUENCE: 170
gacatccaga tgacccag                                                   18

<210> SEQ ID NO 171
<211> LENGTH: 18
<212> TYPE: DNA
<213> ORGANISM: Artificial Sequence
<220> FEATURE:
<223> OTHER INFORMATION: Artificially synthesized sequence

<400> SEQUENCE: 171
gatattgtga tgacccag                                                   18

<210> SEQ ID NO 172
<211> LENGTH: 18
<212> TYPE: DNA
<213> ORGANISM: Artificial Sequence
<220> FEATURE:
<223> OTHER INFORMATION: Artificially synthesized sequence

<400> SEQUENCE: 172
gaaattgtaa tgacacag                                                   18

<210> SEQ ID NO 173
<211> LENGTH: 18
<212> TYPE: DNA
<213> ORGANISM: Artificial Sequence
<220> FEATURE:
<223> OTHER INFORMATION: Artificially synthesized sequence

<400> SEQUENCE: 173
```

```
gacatcgtga tgacccag                                                    18

<210> SEQ ID NO 174
<211> LENGTH: 18
<212> TYPE: DNA
<213> ORGANISM: Artificial Sequence
<220> FEATURE:
<223> OTHER INFORMATION: Artificially synthesized sequence

<400> SEQUENCE: 174
gaaacgacac tcacgcag                                                    18

<210> SEQ ID NO 175
<211> LENGTH: 18
<212> TYPE: DNA
<213> ORGANISM: Artificial Sequence
<220> FEATURE:
<223> OTHER INFORMATION: Artificially synthesized sequence

<400> SEQUENCE: 175
gaaattgtgc tgactcag                                                    18
```

ANTIVIRAL AGENT, ABZYME, PRIMER SET, METHOD FOR PRODUCING POLYNUCLEOTIDE, AND METHOD FOR PRODUCING POLYPEPTIDE

CROSS REFERENCE TO RELATED APPLICATIONS

The present application is a Section 371 U.S. national stage entry of pending International Patent Application No. PCT/JP2011/053752, International Filing Date Feb. 21, 2011, which published on Aug. 25, 2011 as Publication No. WO 2011/102517, which claims the benefit of Japanese Patent Application No. 2010-034998, filed Feb. 19, 2010, and which claims the benefit of Japanese Patent Application No. 2010-035021, filed Feb. 19, 2010, and which claims the benefit of Japanese Patent Application No. 2010-092461, filed Apr. 13, 2010, the contents of which are incorporated by reference in their entireties.

TECHNICAL FIELD

The present invention relates to an antiviral agent, a human abzyme, a primer set, a method for producing a polynucleotide, and a method for producing a polypeptide.

BACKGROUND ART

The inventors of the present invention have conducted various and ingenious researches into abzymes (for example, refer to Patent Literature 1). Conventionally, abzymes which include fully human sequence have been obtained only from Bence Jones protein (BJP) that is obtained from multiple myeloma patients. The number of multiple myeloma patients is small, and besides, only a few BJP contain enzyme activity, so that it has been difficult to obtain human abzymes. However, side effects of human abzymes for a human body are expected to be less. Therefore, domestic and international pharmaceutical companies etc. have longed for useful human abzymes to be developed.

By the way, rabies is an infectious disease which still imposes a heavy disease burden in developing countries and a fatal disease with 100% of mortality rate at a time of the onset of rabies. There is no effective treatment for rabies at this time other than administration of vaccine to prevent rabies from developing after exposure to rabies viruses. Therefore, development of a treatment for rabies from a new viewpoint is desired.

Also, influenza viruses are so diverse in their antigenicity that influenza spreads wide and causes serious damage. Therefore, development of a treatment for influenza from a new viewpoint is desired.

CITATION LIST

Patent Literatures

Patent Literature 1

Japanese Patent Application Publication, Tokukai No. 2006-197930 (Publication Date: Aug. 3, 2006)

Patent Literature 2

Japanese Patent Application Publication, Tokukai No. 2004-97211 (Publication Date: Apr. 2, 2004)

SUMMARY OF INVENTION

Technical Problem

A main object of the present invention is to provide a novel and useful human antibody light chain.

Solution to Problem

The inventors of the present invention have diligently studied for establishment of methods for obtaining a human abzyme from substances other than BJP, and found that (i) cDNA of a κ light chain of a human antibody, the cDNA including a Vκ gene belonging to a subgroup II, or (ii) a fragment of the cDNA, the fragment at least encoding a variable domain, can be more selectively and effectively amplified from human cDNA by two-stage PCR reaction using a primer designed for a first primer on the basis of leader sequence which is characteristic of a Vκ gene belonging to a subgroup II. Based on this finding, the inventors have accomplished the present invention. Incidentally, the inventors mention, in Patent Literature 1, a method by using PCR reaction using a primer including a polynucleotide represented by the nucleotide sequence of SEQ ID NO: 5. The present invention has been made by improving the method described in Patent Literature 1 by changing the nucleotide sequence of SEQ ID NO: 5 to the nucleotide sequence of SEQ ID NO: 1 or 2, and in addition, by applying a second PCR reaction, on the basis of the inventors' ingenious ideas.

Next, the inventors of the present invention have studied novel human antibody light chains obtained by this technique to surprisingly find that some of the obtained human antibody light chains has a high-antiviral activity. Based on the finding, the inventors have accomplished the present invention.

That is, an antiviral agent in accordance with the present invention includes a human antibody κ light chain consisting of a polypeptide having a variable domain represented by the amino acid sequence shown in SEQ ID NO: 26, 14, 22, 30, 50, 54, or 35.

The present invention further provides a human abzyme which is a light chain of a human antibody for a rabies virus and includes enzyme activity.

That is, a human abzyme according to the present invention may be: (i) a human abzyme being a human antibody κ light chain against rabies virus and having an amidase activity and a variable domain consisting of a polypeptide represented by the amino acid sequence shown in SEQ ID NO: 14, 26, 16, 18, 30, 35, or 40; (ii) a human abzyme being a human antibody κ light chain against rabies virus and having a nucleolytic activity and a variable domain consisting of a polypeptide represented by the amino acid sequence shown in SEQ ID NO: 14, 26, 30, 50, or 54; (iii) a human abzyme being a human antibody κ light chain against rabies virus and cytotoxic to cancer cells, and having a variable domain consisting of a polypeptide represented by the amino acid sequence shown in SEQ ID NO: 14, or 30; (iv) a human abzyme being a human antibody κ light chain against rabies virus and having an anti virus activity and a variable domain consisting of a polypeptide represented by the amino acid sequence shown in SEQ ID NO: 14, 26, 22, 30, 50, 54, or 35. These abzymes are human abzymes and considered to produce no or little side effect when administered to humans.

The present invention also provides a polynucleotide according to the present invention for encoding the human antibody κ light chain. Moreover, the present invention also provides a vector containing the polynucleotide according to the present invention, and a transformant in which the polynucleotide according to the present invention is introduced.

Moreover, a primer set according to the present invention is a primer set for amplifying a polynucleotide for encoding at least a variable domain of a human antibody κ light chain via two-stage PCR reaction using a human cDNA as a template, comprising: a first primer for first-stage PCR reaction, the first primer being a polynucleotide having a domain hybridizable with the template in the first stage PCR reaction, the domain being represented by the nucleotide sequence shown in SEQ ID NO: 43 or 44.

By using the primer set according to the present invention, it is possible to selectively and effectively amplify, in human cDNA, a fragment for encoding (i) antibody light chain cDNA having Vκ gene belonging to the subgroup II or (ii) at least the variable domain thereof. This makes it possible to effectively obtain the human antibody κ light chain, which is an abzyme.

The present invention encompasses (i) a method for producing a polynucleotide, the method comprising: performing two-stage PCR reaction by using a primer set according to the present invention, so as to amplify the polynucleotide for encoding at least the variable domain of the human antibody κ light chain from human cDNA, and (ii) a method for producing a polypeptide, the method comprising: producing a polynucleotide by the above method; and expressing the polynucleotide inside a host cell.

Advantageous Effects of Invention

The present invention makes it possible to provide: an antiviral agent containing a significantly useful and novel human antibody κ light chain; a human abzyme which is a novel human antibody κ light chain; a polynucleotide, a vector, and a transformant, each associated with the human antibody κ light chains; a primer set, for efficiently obtaining a human antibody κ light chain, having functions as an antiviral agent or an abzyme; and a method for producing a polynucleotide or a polypeptide by using the primer set.

BRIEF DESCRIPTION OF DRAWINGS

FIG. 5 shows a part of sequence results of each clone.

FIG. 6 shows colony formations of Escherichia coli transformed by heat shock.

FIG. 20 (a) shows a result of another primary purification of a polypeptide of clone #1. FIG. 20 (b) shows a result of another secondary purification of the polypeptide of clone #1.

FIG. 21 shows results of examination on conditions for reaction of a polypeptide of clone #1 and a virus. FIG. 21 (a) shows a result of examination on temperature and time at a time of reaction of a polypeptide of clone #1 and a virus. FIG. 21 (b) shows a result of examination on density and time at a time of reaction of a polypeptide of clone #1 and a virus.

FIG. 22 shows a result of examination on antiviral activity of a polypeptide of clone #1 for various viruses FIG. 23 shows a result of a plaque assay by which antiviral activity of a polypeptide of clone #1 for a rabies virus CVS was examined.

FIG. 24 shows a result of erythrocyte agglutination by which membrane fusion activity of a polypeptide of clone #1 was examined.

FIG. 26 shows a result of examination on antiviral activity of a polypeptide of clone #1 for a vesicular stomatitis virus at different temperatures.

FIG. 27 shows a result of examination on antiviral activity of a polypeptide of clone #7 for a rabies virus CVS.

FIG. 39 shows an amino acid sequence of a human antibody κ light chain in which a cysteine forming a disulfide bonding is substituted.

FIG. 40 shows an amino acid sequence of a human antibody κ light chain in which a cysteine forming a disulfide bonding is substituted.

FIG. 43 shows a leader sequence of a k antibody light chain gene which includes a Vκ gene belonging to a subgroup I.

FIG. 44 shows a leader sequence of a k antibody light chain gene which includes Vκ gene s belonging to subgroups II and III.

FIG. 45 shows a leader sequence of a k antibody light chain gene which includes Vκ gene s belonging to subgroups IV to VI.

FIG. 46 shows parts of each leader sequence corresponding to a first primer in accordance with an embodiment of the present invention.

FIG. 47 shows approximately 60 nucleotides on the 5' end of a k antibody light chain gene which includes a Vκ gene belonging to a subgroup I.

FIG. 48 shows approximately 60 nucleotides on the 5' end of a k antibody light chain gene which includes a Vκ gene belonging to a subgroup II.

FIG. 49 shows approximately 60 nucleotides on the 5' end of a k antibody light chain gene which includes Vκ gene s belonging to subgroups III to VI.

FIG. 50 shows parts of sequence on each 5' end corresponding to a second primer in accordance with an embodiment of the present invention.

DESCRIPTION OF EMBODIMENTS

Figure 1:
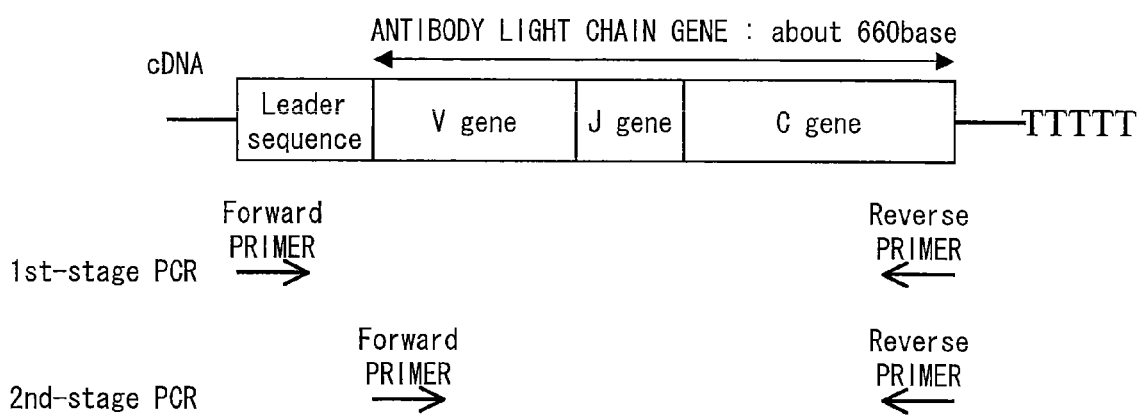
FIG. 1 is a schematic view illustrating a schematic configuration of a primer set in accordance with an embodiment of the present invention.

Embodiments of the present invention are described below. The following descriptions are to describe the present invention and do not imply any limitation on the scope of the present invention.

[1. Human Antibody κ Light Chain]

The present invention provides a novel and useful human antibody κ light chain. In the specification of the present invention, "a human antibody κ light chain" indicates a κ light chain of immune globulin originating from a human.

It is preferable that the human antibody κ light chain in accordance with the present invention is a monomer. Some human antibody κ light chains have much higher antiviral activity in a monomer than in a dimer (described later).

The human antibody κ light chain in accordance with the present invention consists of a polypeptide having a variable domain represented by the amino acid sequence shown in SEQ ID NO: 14, 16, 18, 22, 26, 30, 35, 40, 50, or 54, and reacts on a rabies virus.

Note that, the human antibody κ light chain which includes the variable domain consisting of the polypeptide represented by the amino acid sequence of SEQ ID NO: 14 is also denominated a human antibody κ light chain (#1). The human antibody κ light chain (#1) can be a human antibody κ light chain having the variable domain to which a publicly known human antibody constant domain is added, and the overall amino acid sequence is shown in SEQ ID NO: 1 in one embodiment. CDR1 in the human antibody κ light chain (#1) is the 24th through 39th amino acids in the amino acid sequence of SEQ ID NO 1 and 14. CDR2 is the 55th through 60th amino acids in the amino acid sequence of SEQ ID NO: 1 and 14. CDR3 is the 94th through 103th amino acids in the amino acid sequence of SEQ ID NO: 1 and 14.

The human antibody κ light chain which includes the variable domain consisting of the polypeptide represented by the amino acid sequence of SEQ ID NO: 16 is also denominated a human antibody κ light chain (#16). The human antibody κ light chain (#16) can be a human antibody κ light chain having the variable domain to which a publicly known human antibody constant domain is added, and the overall amino acid sequence is shown in SEQ ID NO: 3 in one embodiment. CDR1 in the human antibody κ light chain (#16) is the 24th through 39th amino acids in the amino acid sequence of SEQ ID NO: 3 and 16. CDR2 is the 55th through 60th amino acids in the amino acid sequence of SEQ ID NO: 3 and 16. CDR3 is the 94th through 103th amino acids in the amino acid sequence of SEQ ID NO: 3 and 16.

The human antibody κ light chain which includes the variable domain consisting of a polypeptide represented by the amino acid sequence of SEQ ID NO: 18 is also denominated a human antibody κ light chain (#7). The human antibody κ light chain (#7) can be a human antibody κ light chain having the variable domain to which a publicly known human antibody constant domain is added, and the overall amino acid sequence is shown in SEQ ID NO: 5 in an embodiment. CDR1 in the human antibody κ light chain (#7) is the 24th through 39th amino acids in the amino acid sequence of SEQ ID NO: 5 and 18. CDR2 is the 55th through 60th amino acids in the amino acid sequence of SEQ ID NO: 5 and 18. CDR3 is the 94th through 102th amino acids in the amino acid sequence of SEQ ID NO: 5 and 18.

The human antibody κ light chain which includes the variable domain consisting of the polypeptide represented by the amino acid sequence of SEQ ID NO: 22 is also denominated a human antibody κ light chain (#6). The human antibody κ light chain (#6) can be a human antibody κ light chain having the variable domain to which a publicly known human antibody constant domain is added, and the overall amino acid sequence is shown in SEQ ID NO: 20 in an embodiment. CDR1 in the human antibody κ light chain (#6) is the 24th through 39th amino acids in the amino acid sequence of SEQ ID NO 20 and 22. CDR2 is the 55th through 60th amino acids in the amino acid sequence of SEQ ID NO: 20 and 22. CDR3 is the 94th through 102th amino acids in the amino acid sequence of SEQ ID NO: 20 and 22.

The human antibody κ light chain which includes the variable domain consisting of the polypeptide represented by the amino acid sequence of SEQ ID NO: 26 is also denominated a human antibody κ light chain (#18). The human antibody κ light chain (#18) can be a human antibody κ light chain having the variable domain to which a publicly known human antibody constant domain is added, and the overall amino acid sequence is shown in SEQ ID NO: 24 in an embodiment. CDR1 in the human antibody κ light chain (#18) is the 24th through 39th amino acids in the amino acid sequence of SEQ ID NO: 24 and 26. CDR2 is the 55th through 60th amino acids in the amino acid sequence of SEQ ID NO: 24 and 26. CDR3 is the 94th through 102th amino acids in the amino acid sequence of SEQ ID NO: 24 and 26.

The human antibody κ light chain which includes the variable domain consisting of the polypeptide represented by the amino acid sequence of SEQ ID NO: 30 is also denominated a human antibody κ light chain (23D4). The human antibody κ light chain (23D4) can be a human antibody κ light chain having the variable domain to which a publicly known human antibody constant domain is added, and the overall amino acid sequence is shown in SEQ ID NO: 28 in one embodiment. CDR1 in the human antibody κ light chain (23D4) is the 24th through 39th amino acids in the amino acid sequence of SEQ ID NO: 28 and 30. CDR2 is the 55th through 60th amino acids in the amino acid sequence of SEQ ID NO: 28 and 30. CDR3 is the 94th through 102th amino acids in the amino acid sequence of SEQ ID NO: 28 and 30.

The human antibody κ light chain which includes the variable domain consisting of the polypeptide represented by the amino acid sequence of SEQ ID NO: 35 is also denominated a human antibody κ light chain (22F6). The human antibody κ light chain (22F6) can be a human antibody κ light chain having the variable domain to which a publicly known human antibody constant domain is added, and the overall amino acid sequence is shown in SEQ ID NO: 33 in one embodiment. CDR1 in the human antibody κ light chain (22F6) is the 24th through 39th amino acids in the amino acid sequence of SEQ ID NO: 33 and 35. CDR2 is the 55th through 60th amino acids in the amino acid sequence of SEQ ID NO: 33 and 35. CDR3 is the 94th through 102th amino acids in the amino acid sequence of SEQ ID NO: 33 and 35.

The human antibody κ light chain which includes the variable domain consisting of the polypeptide represented by the amino acid sequence of SEQ ID NO: 40 is also denominated a human antibody κ light chain (23F1). The human antibody κ light chain (23F1) can be a human antibody κ light chain having the variable domain to which a publicly known human antibody constant domain is added, and the overall amino acid sequence is shown in SEQ ID NO: 38 in an embodiment. CDR1 in the human antibody κ light chain (23F1) is the 24th through 39th amino acids in the amino acid sequence of SEQ ID NO: 38 and 40. CDR2 is the 55th through 60th amino acids in the amino acid sequence of SEQ ID NO: 38 and 40. CDR3 is the 94th through 102th amino acids in the amino acid sequence of SEQ ID NO: 38 and 40.

The human antibody κ light chain which includes the variable domain consisting of the polypeptide represented by the amino acid sequence of SEQ ID NO: 50 is also denominated a human antibody κ light chain (#4). The human antibody κ light chain (#4) can be a human antibody κ light chain having the variable domain to which a publicly known human antibody constant domain is added, and the overall amino acid sequence is shown in SEQ ID NO: 48 in an embodiment. CDR1 in the human antibody κ light chain (#4) is the 24th through 40th amino acids in the amino acid sequence of SEQ ID NO: 48 and 50. CDR2 is the 56th through 61th amino acids in the amino acid sequence of SEQ ID NO: 48 and 50. CDR3 is the 95th through 103th amino acids in the amino acid sequence of SEQ ID NO: 48 and 50.

The human antibody κ light chain which includes the variable domain consisting of the polypeptide represented by the amino acid sequence of SEQ ID NO: 54 is also denominated a human antibody κ light chain (#11). The human antibody κ light chain (#11) can be a human antibody κ light chain having the variable domain to which a publicly known human antibody constant domain is added, and the overall amino acid sequence is shown in SEQ ID NO: 52 in one embodiment. CDR1 in the human antibody κ light chain (#11) is the 24th through 39th amino acids in the amino acid sequence of SEQ ID NO: 52 and 54. CDR2 is the 55th through 60th amino acids in the amino acid sequence of SEQ ID NO: 52 and 54. CDR3 is the 94th through 102th amino acids in the amino acid sequence of SEQ ID NO: 52 and 54.

In one embodiment, the human antibody κ light chain in accordance with the present invention can also be a variant of the human antibody κ light chain described above. The amino acid sequence of the variant is preferably such that cysteine for forming a disulfide bonding with another light chain is either deleted or substituted with any amino acid other than cysteine. This makes it possible to (i) avoid forming of a disulfide bonding of a human antibody κ light chain with another human antibody κ light chain so as to be dimerized and therefore (ii) easily achieve a monomeric human antibody κ light chain. In this case, the human antibody κ light chain in accordance with the present invention consists of a polypeptide represented by the amino acid sequence shown in SEQ ID NO: 15, 17, 19, 23, 27, 31, 36, 41, 51, or 55. Note that "ALEHHHHHH (SEQ ID NO: 12)" at the end of each of the amino acid sequence shown in SEQ ID NO: 15, 17, 19, 23, 27, 31, 36, 41, 51, and 55 is a sequence for refining the human antibody κ light chain, and can be modified as needed.

In a case where there exists a variation other than the cysteine in the amino acid sequence of the variant, such a variation should be such that (i) it does not alter an amidase activity, a nucleolytic degradation activity, cytotoxicity against cancer cells, or an antiviral activity, (ii) it preferably exists outside of the CDR sequence described above, and (iii) it preferably exists outside of the variable domain.

The following human antibody κ light chain s involve antiviral activities (described later in Implementation of Embodiment): the human antibody κ light chain (#6), the human antibody κ light chain (#18), the human antibody κ light chain (#1), the human antibody κ light chain (23D4), the human antibody κ light chain (#4), the human antibody κ light chain (#11), and the human antibody κ light chain (22F6). Also, the following human antibody κ light chain s involve amidase activities, and are referred to also as abzyme in accordance with the present invention (described later in Implementation of Embodiment): the human antibody κ light chain (#18), the human antibody κ light chain (#1), the human antibody κ light chain (23D4), the human antibody κ light chain (#7), the human antibody κ light chain (#16), the human antibody κ light chain (22F6), and the human antibody κ light chain (23F1). Additionally, the following human antibody κ light chain s involve nucleolytic degradation activities, and are referred to also as abzyme in accordance with the present invention (described later in Implementation of Embodiment as with the ones above): the human antibody κ light chain (#18), the human antibody κ light chain (#1), the human antibody κ light chain (#23D4), the human antibody κ light chain (#4), and the human antibody κ light chain (#11). Moreover, the following human antibody κ light chain s involve cytotoxicity against cancer cells, and are referred to also as abzyme in accordance with the present invention (described later in Implementation of Embodiment as with the ones above): the human antibody κ light chain (#1) and the human antibody κ light chain (23D4). Furthermore, the following human antibody κ light chain s involve antiviral activities, and are referred to also as abzyme in accordance with the present invention (described later in Implementation of Embodiment as with the ones above): the human antibody κ light chain (#1), the human antibody κ light chain (#18), the human antibody κ light chain (#6), the human antibody κ light chain (23D4), the human antibody κ light chain (#4), the human antibody κ light chain (#11), and the human antibody κ light chain (22F6).

Speaking from the different perspective, the present invention provides a polypeptide that involves an amidase activity, and is a human antibody κ light chain or its fragment. The polypeptide in accordance with the present invention is immunoglobulin of human origin that exhibits amidase activities.

It is preferable that the polypeptide in accordance with the present invention can be provided either as a monomer or as a dimer, and it is especially preferable that the polypeptide is a monomer.

It is also preferable that the polypeptide is a human antibody κ light chain involving an amidase activity or is a fragment of the human antibody κ light chain. Examples of the polypeptide encompass polypeptides respectively represented by the amino acid sequences shown in SEQ ID NO: 1, 3, and 5, and their respective variants. Note that the polypeptide represented by the amino acid sequence shown in SEQ ID NO: 1 and its variant may be referred to as first polypeptides, (ii) the polypeptide represented by the amino acid sequence shown in SEQ ID NO: 3 and its variant may be referred to as second polypeptides, and (iii) the polypeptide represented by the amino acid sequence shown in SEQ ID NO: 5 and its variant may be referred to as third polypeptides.

In this specification, when used with regard to protein or polypeptide, (i) the term "variants" refer to polypeptides maintaining particular activities involved in aimed polypeptides and (ii) the term "variants of the peptides represented by the amino acid sequence shown in SEQ ID NO: 1, 3, and 5" refer to polypeptides that are human antibody κ light chain s involving amidase activities or are fragments of such, or, more preferably, to polypeptides that are human antibody κ light chain s involving antiviral activities or are fragments of such.

It is a well-known fact in the technical field that some amino acids of an amino residue making up a polypeptide can easily be altered without significantly affecting the structure or function of the polypeptide. In addition to the above fact, it is also a well-known fact that there exist variants of natural proteins that do not significantly alter the structure of function of the natural protein. As has been described, the polypeptide in accordance with the present invention is (i) a human antibody κ light chain involving an amidase activity or (ii) a fragment of such. Thus, the active center of the polypeptide falls in the variable domain. This means that (a) the first polypeptide in accordance with the present invention has no variation in a range of 1st and 113th amino acids corresponding to the variable domain in the amino acid sequence shown in SEQ ID NO: 1 (or 7), especially in ranges of 24th to 39th, 55th to 60th, and 94th to 103rd amino acids corresponding to CDR1, CDR3, and CDR3, respectively, (b) the second polypeptide in accordance with the present invention has no variation in a range of 1st and 113th amino acids corresponding to the variable domain in the amino acid sequence shown in SEQ ID NO: 3, especially in ranges of 24th to 39th, 55th to 60th, and 94th to 103rd amino acids corresponding to CDR1, CDR3, and CDR3, respectively, and (c) the third polypeptide in accordance with the present invention has no variation in a range of 1st and 112th amino acids corresponding to the variable domain in the amino acid sequence shown in SEQ ID NO: 5, especially in ranges of 24th to 39th, 55th to 60th, and 94th to 103rd amino acids corresponding to CDR1, CDR3, and CDR3, respectively.

A person skilled in the art could easily vary one to several amino acids in the amino acids constituting the polypeptide, with the use of well-known technologies. For example, it is possible to vary any one of nucleotides of a polynucleotide for encoding a polypeptide with the use of a well-known point mutation method. It is also possible to (i) design a primer corresponding to any part of the polynucleotide for encoding a polypeptide and then (ii) produce a deletion variant or an insertion variant.

It is preferable that a variant contains a conservative (or non-conservative) amino acid substitution, a deletion, or an insertion, which does not change an amidase activity or an antiviral activity of the polypeptides of the present invention.

It is preferable that a variant of the first polypeptide is the one represented by the amino acid sequence shown in SEQ ID NO: 7. In other words, it is preferable that the cysteine at the 220th site of the polypeptide represented by the amino acid sequence shown in SEQ ID NO: 1 is substituted by another amino acid. For example, the cysteine at the 220th site may be substituted by alanine. Such an amino acid substitution does not cause the S—S bonding between the cysteines at the 220th site, and therefore makes it easy to obtain the first polypeptide in accordance with the present invention in the form of a monomer. As described later, the first polypeptide in accordance with the present invention exhibits a highly antiviral activity especially when in the form of a monomer. Such an amino acid substitution can be carried out by, in a case where, for example, a DNA template for encoding the whole length of a human abzyme is amplified by use of PCR, employing a primer that (i) as a 3'-end primer, has AGC adjacently to a restriction recognition site and (ii) has a sequence adjacently to the AGC, which sequence is specific with respect to the DNA template. Other than this method, well-known methods in the field (e.g. site-directed mutagenesis) can be employed to produce such a variation. In addition, it is also possible to produce a human abzyme forming only monomers by PCR amplification with a specific primer designed for encoding the region up to the 219th amino acid of the DNA template.

Moreover, it is possible to further add a variant to the peptide represented by the amino acid sequence shown in SEQ ID NO: 7. Likewise, monomers can be easily obtained by substituting the cysteine at the 219th site of the second polypeptide and the cysteine at the 220th site of the third polypeptide with other amino acids respectively.

The polypeptide in accordance with the present embodiment is thus a human antibody κ light chain involving an amidase activity or is a fragment of such. It is then preferable that the polypeptide in accordance with the present invention is (i) a polypeptide represented by the amino acid sequence shown in SEQ ID NO: 1, 3, 5, or 7 or (ii) a polypeptide consisting of an amino acid sequence in which one to several amino acids are substituted, deleted, or inserted, in the amino acid sequence shown in SEQ ID NO: 1, 3, 5, or 7.

It is preferable that such variations of one to several amino acids are produced in a constant domain. In other words, it is preferable that (i) the variations of the first polypeptide are produced (a) in a range of the 114th to 220th amino acids of the amino acid sequence shown in SEQ ID NO: 1 or (b) in a range of the 114th to 219th amino acids of the amino acid sequence shown in SEQ ID NO: 7, (ii) the variations of the second polypeptide are produced in a range of the 114th to 220th amino acids of the amino acid sequence shown in SEQ ID NO: 3, and (iii) the variations of the third polypeptide are produced in a range of the 113th to 219th amino acids of the amino acid sequence shown in SEQ ID NO: 5.

The polypeptide in accordance with the present invention is a human antibody κ light chain or a fragment of such, and can also be an abzyme involving an amidase activity. In the embodiment, the abzyme in accordance with the present invention can be an antibody against the rabies virus, and preferably involves an antiviral activity.

A first abzyme in accordance with the present invention has a variable domain falling in a range of 1st to 113th amino acids of the amino acid sequence shown in SEQ ID NO: 1. The 24th to 39th, 55th to 60th, and 94th to 103rd amino acids of the first abzyme correspond to CDR1, CDR2, and CDR3, respectively. A second abzyme in accordance with the present invention has a variable domain falling in a range of 1st to 113th amino acids of the amino acid sequence shown in SEQ ID NO: 3. The 24th to 39th, 55th to 60th, and 94th to 103rd amino acids of the second abzyme correspond to CDR1, CDR2, and CDR3, respectively. A third abzyme in accordance with the present invention has a variable domain falling in a range of 1st to 113th amino acids of the amino acid sequence shown in SEQ ID NO: 1. The 24th to 39th, 55th to 60th, and 94th to 103rd amino acids of the third abzyme correspond to CDR1, CDR2, and CDR3, respectively.

The human antibody κ light chain and the polypeptide in accordance with the present invention include products recombinantly engineered from (i) naturally refined products, (ii) products of chemosynthetic procedures, and (iii) prokaryotic hosts or eukaryotic hosts (including bacterial cells, yeast cells, higher-plant cells, insect cells, and mammalian cells, for example). Depending on the hosts used during the recombinant engineering procedures, the polypeptide in accordance with the present invention can be glycosylated or non-glycosylated. Additionally, the polypeptide can, in some cases, contain modified initiating methionine residues as a result of host-mediating processes.

The human antibody κ light chain and the polypeptide in accordance with the present invention need to be polypeptides made of amino acids being combined through peptide-bonding. However, the human antibody κ light chain and the polypeptide are not limited to such, but can be peptide complexes containing structures other than that of a polypeptide. Examples of the "structures other than that of a polypeptide", if used at all in the present specification, encompass, but not limited to, a sugar chain and an isoprenoid residue.

In addition, the human antibody κ light chain and the polypeptide in accordance with the present invention can contain additional polypeptides. Examples of the additional polypeptides encompass epitope-tagged polypeptides such as His, Myc, and Flag.

Another aspect of the present invention is to provide a method for producing (i) a polypeptide that is a human antibody κ light chain involving an amidase activity or is a fragment of such or (ii) a polypeptide that is a human antibody κ light chain involving an antiviral activity or is a fragment of such. The method in accordance with the present invention for producing the polypeptide can also be a method for producing a human antibody κ light chain or an abzyme.

In one embodiment, the method in accordance with the present invention for producing the polypeptide uses a vector containing polynucleotide that is for encoding the polypeptide.

In one aspect of the present embodiment, the method may be preferably such that the vector is a recombinant expression vector. In a case where the vector is a recombinant expression vector, it is possible to employ a method such as one including the steps of (i) introducing a polynucleotide, which is for encoding the polypeptide in accordance with the present invention, into a recombinant expression vector, (ii) introducing the polynucleotide into a host capable of allowing expression of the polypeptide by use of a well-known method, and (iii) refining the polypeptide that can be obtained through translation inside the host (transformant). The recombinant expression vector can be a plasmid, and will accomplish its purpose as long as the vector can introduce a targeted polynucleotide into the host. It is preferable that the method in accordance with the present embodiment for producing the polypeptide includes the step of introducing the vector into the host.

In a case where a foreign polynucleotide is thus introduced into a host, it is preferable that a promoter, which functions to express the foreign polynucleotide inside the host, is incorporated into the recombinant expression vector. A method for refining a polypeptide having been recombinantly engineered varies, depending on a type of host, a characteristic of the polypeptide, and the like. However, by use of a tag and the like, it is possible to refine the polypeptide with relative ease.

It is preferable that the method in accordance with the present embodiment for producing the polypeptide further includes the step of refining the polypeptide out of a cell or tissue extract, each of which contains the polypeptide. It is preferable that the step of refining the polypeptide includes the steps of, but not limited to, (i) preparing a cell extract out of a cell or a tissue by use of a well-known method (e.g. a method by which a cell or a tissue is destroyed and then subjected to centrifugation so that soluble fractions are collected) and (ii) refining the polypeptide by use of a well-known method (e.g. ammonium sulfate precipitation or ethanol precipitation, acid extraction, negative ion or positive ion exchange chromatography, phosphocellulose chromatography, hydrophobic interaction chromatography, affinity chromatography, hydroxyapatite chromatography, and lectin chromatography). It is most preferable to use high-performance liquid chromatography (HPLC) for refining the polypeptide.

In another aspect of the present embodiment, the method in accordance with the present embodiment for producing the polypeptide is preferably arranged such that the vector is used in a cell-free protein synthetic system. In a case where a cell-free protein synthetic system is employed, various commercial kits can be used. It is preferable that the method includes the step of incubating the vector and a cell-free protein synthetic liquid.

The cell-free protein synthetic system (also called a cell-free protein synthetic method or a cell-free protein translation system) (i) is a method widely used for identification etc. of various proteins that are encoded into intracellular mRNAs and cloned cDNAs and (ii) uses a cell-free protein synthetic liquid.

Examples of the cell-free protein synthesis system encompass a system using a wheat germ extract, a system using a rabbit reticulocyte extract, a system using an *escherichia coli* S30 extract, and a cell component extract that can be obtained from vacuolization protoplast of plants. Generally, in order to translate eukaryote genes, an eukaryotic cell system, that is, the system using a wheat germ extract or the system using a rabbit reticulocyte extract, is selected. However, in view of the origins (prokaryote/eukaryote) of the genes to be translated, any one of the synthetic systems can be employed.

Note that many of viral gene products express activities after being translated and then subjected to complex biochemical reactions involving intracellular membranes such as endoplasmic reticulum and Golgi apparatus. Thus, in order to reproduce the various biochemical reactions in test tubes, it is necessary to add intracellular membrane components (e.g. microsomal membrane). A cell component extract, which can be obtained from de-vacuolization protoplast of plants, can be used as a cell-free protein synthetic liquid maintaining an intracellular membrane component. This makes it unnecessary to add a microsomal membrane. Therefore, such a cell component extract is preferred.

The term "intracellular membrane component", when used in the present specification, refers to organelles (i.e. overall intracellular granules such as endoplasmic reticulum, Golgi apparatus, mitochondrion, chloroplast, and vacuole) made up of lipid membranes that exist inside cytoplasm. Endoplasmic reticulum and Golgi apparatus especially play important roles in post-translation modifications of protein, and are therefore indispensable cell components for maturation of membrane protein and secretory protein.

In another embodiment, the method in accordance with the present invention for producing the polypeptide is preferably arranged such that the polypeptide is refined from a cell or tissue that naturally expresses the polypeptide. Moreover, it is preferable that the method in accordance with the present embodiment for producing the polypeptide includes the step of identifying, by use of an antibody or oligonucleotide, a cell or tissue that naturally expresses the polypeptide in accordance with the present invention. It is also preferable that the method in accordance with the present embodiment for producing the polypeptide includes the step of refining the polypeptide.

In a further embodiment, the method in accordance with the present invention for producing the polypeptide chemically synthesizes the polypeptide in accordance with the present invention. A person skilled in the art recognizes, without any difficulty, that the polypeptide in accordance with the present invention can be chemically synthesized if a well-known chemosynthesis technology is applied to it on the basis of the amino acid sequence of the polypeptide in accordance with the present invention described in the present specification.

A polypeptide thus obtained by use of the method in accordance with the present invention for producing the polypeptide can be a polypeptide variant that exists in nature or a polypeptide variant that is artificially produced.

Thus, it can be said that the method in accordance with the present invention for producing the polypeptide can be achieved by use of technologies that are well known and commonly used, provided that at least the amino acid sequence of the polypeptide or the nucleotide sequence of polynucleotide for encoding the polypeptide is used as a basis. Therefore, it should be noted that the technical scope of the present invention encompasses methods for producing the polypeptide, which methods include steps other than the various steps described above.

[2: Polynucleotide]

In one aspect, the present invention provides a gene that encodes (i) a human antibody κ light chain according to the present invention or (ii) a polypeptide according to the present invention. The expression "gene that encodes a human antibody κ light chain", when used in the present specification, means a polynucleotide that encodes a human antibody κ light chain or a polypeptide which is a fragment of the human antibody κ light chain.

The term "polynucleotide", when used in the present specification, is used replaceable with "gene", "nucleic acid" and "nucleic acid molecule", and intends to mean a polymer of a nucleotide. The term "nucleotide sequence", when used in the present specification, is used replaceable with "nucleic acid sequence" and "nucleotide sequence", and is shown as a sequence of a deoxyribonucleotide (abbreviated as A, G, C, and T).

It is preferable that the polynucleotide according to the present invention encode a polypeptide according to the present invention. In a case in which an amino acid sequence of a specific polypeptide is obtained, a nucleotide sequence of a polynucleotide that encodes that polypeptide is easily designable.

It is preferable that a polynucleotide according to the present invention be (i) a gene encoding a κ light chain of a human antibody that has amidase activity, (ii) a gene encoding a κ light chain of a human antibody that has nucleolytic degradation activity, (iii) a gene encoding a κ light chain of a human antibody having cytotoxicity against cancer cells, or (iv) a gene encoding a κ light chain of a human antibody having antiviral activity, and is further preferable to be a polynucleotide represented by the nucleotide sequence of SEQ ID NO: 2, 4, 6, 8, 21, 25, 29, 34, 39, 49 or 53, or a variant thereof. The polynucleotide represented by the nucleotide sequence of SEQ ID NO: 2 or the variant thereof encodes a first polypeptide, and may be called a first polynucleotide. The polynucleotide represented by the nucleotide sequence of SEQ ID NO: 4 or the variant thereof encodes a second polypeptide, and may be called a second polynucleotide. A polynucleotide represented by the nucleotide sequence of SEQ ID NO: 6 or a variant thereof encodes a third polypeptide, and may be called a third polynucleotide. Note that a polynucleotide represented by the nucleotide sequence of SEQ ID NO: 8 encodes a polypeptide represented by an amino acid sequence of SEQ ID NO: 7, and corresponds to the third polynucleotide.

The term "variant", when used in the present specification in relation to the polynucleotide, intends to mean a polynucleotide that encodes a polypeptide having identical activity to an activity of a specific polypeptide, and "a variant of a polynucleotide represented by a nucleotide sequence of any one of SEQ ID NO: 2, 4, 6, 8, 21, 25, 29, 34, 39, 49, or 53" intends to mean a polynucleotide that encodes a κ light chain of the amidase activity, nucleolytic degradation activity, cytotoxicity against cancer cells, or antiviral activity. Namely, when used in the present specification, the variant in viewpoint of the polynucleotide is a polynucleotide that encodes a κ light chain of a human antibody that has amidase activity, nucleolytic degradation activity, cytotoxicity against cancer cells, or antiviral activity, and can be the followings:

a polynucleotide represented by a nucleotide sequence in which one or several nucleotides is substituted, deleted or added in the nucleotide sequence of SEQ ID NO: 2, 4, 6, 8, 21, 25, 29, 34, 39, 49 or 53;

a polynucleotide that can be hybridized under a stringent condition with a complementary strand represented by the nucleotide sequence of SEQ ID NO: 2, 4, 6, 8, 21, 25, 29, 34, 39, 49, or 53; or a polynucleotide in which TGT at an end of a nucleotide sequence of any one of SEQ ID NO: 2, 4, 6, 8, 21, 25, 29, 34, 39, 49, or 53, which end encodes cysteine, is substituted with a nucleotide sequence encoding another amino acid.

As described above, a polypeptide according to the present invention is a κ light chain of a human antibody or a fragment thereof, which antibody has amidase activity, nucleolytic degradation activity, cytotoxicity against cancer cell, or antiviral activity, and which its activity center is in a variable domain. Hence, the human antibody κ light chain according to the present invention that encodes a polynucleotide includes no variation in an amino acid corresponding to CDR in an amino acid sequence of the human antibody κ light chain according to the present invention, and preferably includes no variation in an amino acid corresponding to the variable domain. For example, a polypeptide encoded by a first polynucleotide according to the present invention includes no variation on 1st to 113th amino acids of the amino acid sequence of SEQ ID NO: 1 corresponding to the variable domain, in particular on 24th to 39th amino acids, 55th to 60th amino acids, and 94th to 103th amino acids, which correspond to CDR1, CDR2, and CDR3, respectively. The polypeptide encoded by a second polynucleotide according to the present invention includes no variation on the 1st to 113th amino acids corresponding to a variable domain in the amino acid sequence of SEQ ID NO: 3, in particular, on 24th to 39th amino acids, 55th to 60th amino acids, and 94th to 103th amino acids, which correspond to CDR1, CDR2, and CDR3, respectively. The polypeptide encoded by a third polynucleotide according to the present invention includes no variation in the amino acid sequence of SEQ ID NO: 5 on 1st to 112th amino acids that correspond to the variable domain, in particular on 24th to 39th amino acids, 55th to 60th amino acids, and 94th to 102th amino acids, which correspond to CDR1, CDR2, and CDR3, respectively.

Moreover, by substituting cysteine that forms a disulfide bond on a C-end of the antibody light chain, it is possible to easily achieve a monomeric human antibody light chain according to the present invention, as described above. For this reason, a polynucleotide whose end TGT that codes cysteine is substituted with a nucleotide sequence that encodes another amino acid, in the nucleotide sequence of any one of SEQ ID NO: 2, 4, 6, 8, 21, 25, 29, 34, 39, 49, or 53, can be used suitably. As the nucleotide sequence encoding another amino acid, for example, GCTCTCGAGCACCACCACCACCAC-CACTGA (SEQ ID NO: 13) that encodes ALEHHHHHH (SEQ ID NO: 12) (+termination codon) may be used.

The polynucleotide according to the present invention may be present in a form of RNA (e.g. mRNA) or a form of DNA (e.g. cDNA or genomic DNA). The DNA may be double stranded or single stranded. The single stranded DNA or RNA may be a coding strand (also known as sense strand), or may be a noncoding strand (also known as antisense strand).

The term "oligonucleotide", when used in the present specification, intends to mean several to several ten nucleotides that are bonded together, and can be used in replacement of "polynucleotide". Short oligonucleotides are called dinucleotides (dimer) or trinucleotides (trimer), whereas long oligonucleotides are represented by the number of polymerized nucleotides, such as 30 mer or 100 mer. The oligonucleotide may be generated as a fragment of a longer polynucleotide, or may be chemically synthesized.

The polynucleotide according to the present invention can also be fused into a polynucleotide that encodes the foregoing tagged label (tagged sequence or marker sequence) on its 5'-end or 3'-end.

Hybridization can be performed by a known method such as a method disclosed in Sambrook et al., Molecular Cloning, A Laboratory Manual, 2d Ed., Cold Spring Harbor Laboratory (1989). Usually, the higher the temperature and the lower the salt concentration, the higher the stringency is (becomes difficult to hybridize), which allows for obtaining a more homologous polynucleotide. An appropriate hybridization temperature differs depending on the nucleotide sequence and a length of that nucleotide sequence. For example, when a DNA fragment consisted of 18 nucleotides encoding 6 amino acids is used as a probe, it is preferable that the temperature be not more than 50° C.

The term "stringent hybridization condition", when used in the present specification, intends to mean (i) incubation in a hybridization solution (containing 50% formaldehyde, 5×SSC (150 mM NaCl, 15 mM trisodium citrate), 50 mM sodium phosphate (pH 7.6), 5× Denhartdt's solution, 10% dextran sulfate, and 20 µg/ml denatured sheared salmon sperm DNA) for one night at 42° C., and thereafter (ii) washing a filter in 0.1×SSC at approximately 65° C. A polynucleotide that hybridizes with "a part" of the polynucleotide intends to mean a polynucleotide (either of DNA or RNA) that hybridizes with a part of a reference polynucleotide, which part is at least longer than approximately 15 nucleotide (nt), more preferably at least longer than approximately 20 nt, further preferably at least longer than 30 nt, and further more preferably longer than approximately 30 nt. Such a polynucleotide (oligonucleotide) that hybridizes with "a part" of the polynucleotide is also useful as a detection probe discussed in more details in the present specification.

As described above, the polynucleotide according to the present invention is a polynucleotide that encodes a κ light chain of a human antibody that has amidase activity, a κ light chain of a human antibody having nucleolytic degradation activity, a κ light chain of a human antibody having cytotoxicity against cancer cell, or a κ light chain of a human antibody having antiviral activity, and is preferably any one of the following polynucleotides: (1) a polynucleotide represented by the nucleotide sequence of SEQ ID NO: 2, 4, 6, 8, 21, 25, 29, 34, 39, 49, or 53; (2) a polynucleotide represented by a nucleotide sequence in which one or several nucleotides is substituted, deleted or added in the nucleotide sequence of any one of polynucleotides of SEQ ID NO: 2, 4, 6, 8, 21, 25, 29, 34, 39, 49 or 53; (3) a polynucleotide being hybridizable under a stringent condition with a polynucleotide made of a complementary strand represented by a nucleotide sequence in which one or several nucleotides is substituted, deleted or added in the nucleotide sequence of any one of SEQ ID NO: 2, 4, 6, 8, 21, 25, 29, 34, 39, 49 or 53; or (4) a polynucleotide whose nucleotide sequence is such that cysteine-encoding TGT at an end of the nucleotide sequence of any one of SEQ ID NO: 2, 4, 6, 8, 21, 25, 29, 34, 39, 49, or 53, is substituted with a nucleotide sequence encoding another amino acid.

The polynucleotide according to the present invention may include a sequence of an untranslated region (UTR), a vector sequence (including an expression vector sequence), or like sequence.

A vector according to the present invention can be prepared by inserting a predetermined vector into the polynucleotide according to the present invention, by a known gene recombination technique. The vector is not limited to this, and a cloning vector may be used as well as a recombinant expression vector later described.

A supply source for obtaining the polynucleotide according to the present invention is not limited in particular, however it is preferable to be biological material. The term "biological material", when used in the present specification, intends to mean a biological sample (tissue sample or cell sample obtained from a living body). For example, a human lymphocyte is suitably used in Examples described later, however the present invention is not limited to this.

[3: Antiviral Agent]

The present invention also provides an antiviral agent. In the present specification, antiviral activity means activities that reduce virus infectiousness, proliferation potency or immune evasion ability. The virus infectiousness means the property of a virus that adsorbs to or enters into a host cell. An antiviral activity at this time is, for example, an activity of at least partially cleaving or decomposing surface protein of virus particles by activity of human abzyme, to minimize the adsorbing or entering of the virus into the host cell. Namely, the antiviral activity can be reworded as a neutralization activity of the virus.

A proliferation potency of the virus means (i) a synthesis ability of structural protein of virus particles in a host cell, (ii) forming ability of the virus particles, or (iii) replication ability of the virus gene. This antiviral activity means, for example, an activity that down-regulates the formation of a matured virus particle by decomposing a certain virus protein in the host cell. Examples of the virus protein encompass a virus protein that promotes synthesis of the virus protein or that is essential for synthesis, or a virus protein which promotes the replication of a virus gene or which is essential for the replication.

The immune evasion ability of the virus means an ability to evade an immune system of the host. This antiviral activity is an activity which cleaves a part of the surface protein of the virus particle, to change the virus particle into a form recognizable as an antigen, or is an activity which decomposes the virus protein that partially obstructs the immune system of the host.

A virus that a first antiviral agent according to the present invention targets may be an envelope virus, may be a negative single stranded RNA virus, and may be a virus belonging to the Rhabdoviridae family (e.g. rabies virus and vesicular stomatitis virus), and is targeted to rabies virus in particular.

The human antibody κ light chain (#1) (first polypeptide), human antibody κ light chain (#6), human antibody κ light chain (#18), and human antibody κ light chain (23D4), each according to the present invention, has an effect as described in Examples later described of remarkably reducing the infectiousness of rabies virus. The infectious disease of rabies virus can be easily prevented by vaccination. However, when the infectious disease of rabies virus is onset, there is currently no positive treatment available, and mortality of the patients in which symptoms of this infectious disease appear is almost 100%, even if an immune response is induced. Accordingly, the human antibody κ light chain (#1) (first polypeptide), the human antibody κ light chain (#6), the human antibody κ light chain (#18) and the human antibody κ light chain (23D4), each according to the present invention, are particularly useful for treating the onset infectious disease of rabies virus.

Hence, in one embodiment, a first antiviral agent according to the present invention includes any one of a human antibody κ light chain (#1) (first polypeptide), a human antibody κ light chain (#6), a human antibody κ light chain (#18), and a human antibody κ light chain (23D4), each according to the present invention. Moreover, the antiviral agent shows antiviral activity against viruses belonging to Rhabdoviridae. The virus against which the antiviral agent shows antiviral activity is, for example, rabies virus or vesicular stomatitis virus.

The virus targeted by a second antiviral agent according to the present invention may be an envelope virus, a negative single stranded RNA virus, or a virus belonging to Orthomyxoviridae, in particular, influenza virus. The type of the targeted influenza virus is not limited in particular, however may suitably be targeted to influenza virus type A.

The human antibody κ light chain (#1) (first polypeptide), human antibody κ light chain (#4), human antibody κ light chain (#11), human antibody κ light chain (#18), and human antibody κ light chain (22F6), each according to the present invention, each has an effect of remarkably reducing the infectiousness of the influenza virus, as described in Examples later described. The influenza virus is one of viruses that are given medical attention, due to the easiness in occurrence of variation and the seriousness of damage caused thereby. The human antibody κ light chain (#1) (first polypeptide), human antibody κ light chain (#4), human antibody κ light chain (#11), human antibody κ light chain (#18), and human antibody κ light chain (22F6), each according to the present invention, may be useful in particular to prevent the prevalence of the influenza virus.

Hence, in one embodiment, a second antiviral agent according to the present invention includes any one of the human antibody κ light chain (#1) (first polypeptide), human antibody κ light chain (#4), human antibody κ light chain (#11), human antibody κ light chain (#18), and human antibody κ light chain (22F6), each according to the present invention. Moreover, the antiviral agent may show antiviral activity against the influenza virus. The virus that the antiviral agent shows antiviral activity against is, for example, influenza virus type A.

Moreover, it is preferable that the antiviral agent of the present invention shows no fusing activity of a lipid bilayer. This is because when the antiviral agent of the present invention affects the envelope to show the antiviral activity, this may damage the host cell. As described later in Examples, human abzyme according to the present invention shows no fusing activity of the lipid bilayer.

In one embodiment, the antiviral agent according to the present invention may be administered by direct injection, to be used in a human or an animal. The antiviral agent according to the present invention may also be prescribed for parenteral administration, mucosal administration, intramuscular administration, intravenous administration, subcutaneous administration, intraocular administration, or percutaneous administration. Typically, protein is contained in the composition by an amount of 0.01 to 30 mg/kg weight, preferably 0.1 to 10 mg/kg weight, more preferably 0.1 to 1 mg/kg weight.

The antiviral agent according to the present embodiment may include, other than the human antibody κ light chain (#1) (first polypeptide), human antibody κ light chain (#6), human antibody κ light chain (#18), or human antibody κ light chain (23D4), a pharmaceutically acceptable carrier, a diluent, or an excipient (including combinations of these).

The antiviral agent according to the present embodiment is to be used for a human or an animal, and typically optionally includes at least one of a pharmaceutically acceptable diluent, carrier, or excipient. A pharmaceutically acceptable carrier or excipient for treatment use is well known in the pharmaceutical field, and for example is disclosed in Remington's Pharmaceutical Sciences, Mack Publishing Co. (edited by A. R. Gennaro, 1985). The pharmaceutically acceptable carrier, diluent or excipient can be easily selected by a skilled person, depending on an intended administration route and a standard pharmaceutical practice. Moreover, the antiviral agent according to the present embodiment may further optionally include an appropriate binding agent, lubricant, suspending agent, coating flux, or solubilizing agent.

Essential conditions of the composition/prescriptions may differ depending on different delivery systems. As an example, the antiviral agent according to the present invention may be prescribed to be used as a nose spray or aerosol for inhalation with use of a mini pump or through a mucosal course, or for parenteral delivery (here, the antiviral agent according to the present invention is prescribed as an injectable form for delivery through, for example, an intravenous course, intramuscular course, or subcutaneous course). Alternatively, this prescribed object may be designed to be delivered from both courses.

Moreover, when the human antibody κ light chain or the antiviral agent according to the present invention is used to be administered inside a living body, various techniques may be used to improve stability (half-life in blood) of the human antibody κ light chain in vivo. For example, it is known that an antibody such as IgG extends in the half-life in blood when a neonatal Fc receptor (FcRn) bonds to Fc (e.g. see Roopenian, D. C. et al., Nat Rev Immunol vol. 7, 715-725 (2007)), and it is possible to modify a C-terminal of the human antibody κ light chain according to the present invention so as to have a bonding activity with FcRn. Moreover, by making the human antibody κ light chain according to the present invention be a dimer, it is possible to add PEG (polyethylene glycol).

On the basis of the description in the present specification, it is easily understandable by a skilled person that another form (e.g. a kit) of an antiviral agent according to the present embodiment and a method of processing (prevention and/or treatment) a disease with use of the antiviral agent according to the present invention are also within the scope of the present invention. In the method of treating a disease with use of the antiviral agent according to the present invention, the disease to be treated may be a virus infectious disease, for example rabies virus infectious disease, vesicular stomatitis virus infectious disease, or influenza virus infectious disease. Moreover, in the method of treating a disease with use of the antiviral agent according to the present invention, a subject to be treated may be a human or a non-human animal.

Moreover, in another embodiment, the antiviral agent according to the present invention may be used for eliminating the virus from an article from which the virus is to be eliminated. For example, the antiviral agent according to the present invention may be in the form of a spray, an embrocation, an immersion agent or the like, which are respectively used for spraying or applying to the subject object, or immersing the subject object therein. The antiviral agent according to the present embodiment may further include, in accordance with its use, a known antiviral agent, surfactant, stabilizer, pH adjuster, buffer, isotonizing agent, chelating agent, preservative, thickener, solvent, or the like.

[4. Primer Set]

The inventors of the present invention found that an abzyme in many cases has a κ light chain, which light chain has a catalytic triad residues-like structure, by analyzing a sequence and conformation of a monoclonal antibody (abzyme) of a mouse having enzyme activity. The catalytic triad residues-like structure is, for example, a structure formed by a serine residue, histidine residue and asparagine residue, and is considered as having catalyst activity.

The gene of the antibody κ light chain is constructed by selecting and reforming genes from a Vκ gene group and a Jκ gene group, each present in a germline gene, and a constant domain gene group.

The inventors of the present invention analyzed the antibody κ light chain of a mouse as to how a germline gene type of the Vκ gene related to conformation of the antibody κ light chain of a mouse. As a result, the inventors found that only 10 kinds of the genes construct an antibody light chain having a catalytic triad residues-like structure, among 93 kinds of germline gene kinds in the germline gene kind of the Vκ gene. Furthermore, the inventors found that when the germline gene kind of the Vκ gene is included in these 10 kinds, the antibody light chain becomes an abzyme by a high probability (Patent Literature 2).

In consideration of application to medical treatment, the inventors of the present invention further proceeded with their analysis as to whether or not the same phenomenon occurs with a human antibody, not just the mouse antibody. The inventors of the present invention discussed information all around the world that has been reported until now, which relate to antibodies. As a result, it was found that in case of humans, the antibody light chain has the catalytic triad residues-like structure by a high frequency when the Vκ gene belongs to subgroup II (Patent Literature 1).

Hence, if it is possible to obtain, from a human cDNA library, an antibody light chain having a Vκ gene that belongs to subgroup II or at least a fragment that encodes a variable domain, the present invention is useful.

However, the nucleotide sequence of Vκ gene is similar between the subgroups, so it is not easy to positively select and amplify just the antibody light chain cDNA or its fragment, which light chain cDNA has the Vκ gene belonging to the subgroup II, from a human lymphocyte cDNA, for example by PCR reaction.

Moreover, even if the Vκ gene belongs to the same subgroup II, an actually obtained cDNA from a human lymphocyte has diversity due to the reformation described above. Hence, there is a possibility that the level of the abzyme activity obtained from the selected cDNA, a target substrate, and the like may differ. Moreover, not all of antibodies having the triad residue-like structure have enzyme activity. Whether or not an antibody has enzyme activity is considered to be determined depending on a slight difference in conformation other than the triad residue-like structure of the antibody conformation.

Hence, by obtaining an extremely large amount of types of the antibody light chain cDNA or its fragment, which antibody light chain cDNA has the Vκ gene belonging to subgroup II, it is possible to produce abzymes of different uses and abzymes having high usability for specific uses. Hence, techniques for selecting and efficiently amplifying an antibody light chain cDNA or its fragment from a human cDNA library, which antibody light chain cDNA has a Vκ gene belonging to the subgroup II, has been in the need for the use of developing a useful abzyme.

Accordingly, the present invention provides a primer set for amplifying, by two-stage PCR reaction with the human cDNA serving as a template, a polynucleotide at least encoding a variable domain of a κ light chain of a human antibody belonging to the subgroup II. By performing the two-stage PCR reaction with use of the primer set according to the present invention and with the human cDNA serving as the template, it is possible to efficiently obtain a human antibody κ light chain that functions as an antiviral agent or abzyme as described above.

As a primer for the first PCR reaction, a 5'-end primer and a 3'-end primer are designed. The 5'-end primer typically includes a 15 to 30-nucleotide polynucleotide that specifically hybridizes with a complementary strand of a region downstream from the 5'-end of the polynucleotide to be amplified, and preferably has a nucleotide sequence identical to that of a region downstream from the 5'-end of the polynucleotide to be amplified. Moreover, the 3'-end primer typically includes a 15 to 30-nucleotide polynucleotide that specifically hybridizes with a region upstream from a 3'-end of a polynucleotide to be amplified, and preferably has an identical nucleotide sequence to that of a complementary strand in a region upstream from the 3'-end of the polynucleotide to be amplified.

The primer set according to the present invention includes, as the 5'-end primer, a 5'-end primer (first primer) for the first stage PCR reaction and a 5'-end primer (second primer) for the second stage PCR reaction, and includes, as a 3'-end primer, a 3'-end primer (third primer) for the first stage PCR reaction and a 3'-end primer (fourth primer) for the second stage PCR reaction. The first to fourth primers are, as shown in FIG. 1, in a nested relationship.

In the present specification, what is meant by "specifically hybridizing" is to form no polynucleotide double strand in regions other than the region to be targeted by the polynucleotide that serves as the template. Here, a Tm value is preferably not less than 50° C., is more preferably not less than 55°

C., is further preferably not less than 60° C., and is most preferably not less than 65° C.

The 5'-end primers are not limited as long as it at least has a region for hybridizing with a template in the PCR reaction; for example, it may have an optional restriction enzyme recognition site on the 5'-end of the region. The restriction enzyme recognition site is, for example, a site that is cleaved with a commercially available restriction enzyme. A sequence of the restriction enzyme recognition site is a publicly known sequence that is disclosed on a catalog or the like distributed by various producers that provide restriction enzymes. Hence, the restriction enzyme recognition site may be selected as appropriate in accordance with a vector used in (sub)cloning or expression. The restriction enzyme recognition site encompasses, for example, a restriction enzyme site cleaved with a restriction enzyme, thereby having a blunt end, and a restriction enzyme site cleaved with a restriction enzyme, thereby having a sticky end. For example, when a vector that allows for ligating a DNA fragment having a blunt end with use of topoisomerase is used as a subcloning vector, no restriction enzyme digestion of the vector or purification of the vector that has been subjected to the restriction enzyme process is necessary. This simplifies the operation.

Moreover, the 5'-end primers may have a further nucleotide on the 5'-end of the restriction enzyme recognition site. A skilled person is capable of designing the number and type of the further nucleotide as appropriate to suitably amplify the PCR product, such as avoiding the formation of a primer dimer, avoiding formation of a hairpin, and alleviation of PCR reaction conditions.

The 3'-end primers are sufficient as long as it includes at least a region for hybridizing with a target sequence in the PCR reaction, and the region may have the restriction enzyme recognition site on its 3'-end. Moreover, the 3'-end primer may have a further nucleotide on the 3'-end of the restriction enzyme recognition site. The restriction enzyme recognition site on the 3'-end primer and the further nucleotide may be optionally selected based on a standard similar to the design of the 5'-end primer.

The PCR reaction may be performed by use of a commercially available thermal cycler. Moreover, a commercially available PCR reagent may be used. The operation of the thermal cycler is sufficiently performed by following its attached instructions; for example, a temperature to denature DNA may be 94° C., a temperature for annealing DNA may be 50° C. to 60° C., and a temperature for elongation reaction of the DNA may be 68° C.

The human cDNA is not particularly limited as long as it includes cDNA of the antibody light chain, and can be taken out from human body fluid or tissue, more preferably from blood, lymph fluid, spleen tissue or the like, however it is particularly preferable that the human cDNA be a cDNA derived from a human lymphocyte that is prepared from human lymphocytes. The cDNA derived from the human lymphocyte can be obtained by, for example, isolating lymphocytes from body fluid including the human lymphocytes such as peripheral blood or the like with use of Ficoll-paque or the like, extracting a total RNA with use of a commercially available RNA extraction kit, and applying the publicly known RT-PCR method. However, there are no limitations in particularly how it is obtained.

Next described in detail is the nucleotide sequence of the first to fourth primers, in particular, nucleotide sequences of a region for hybridizing with a template by the PCR reaction.

FIG. 1 illustrates an example of a design of the first to fourth primers. As illustrated in FIG. 1, the antibody κ light chain gene is arranged in the order of, from the 5'-end, V gene, J gene and C gene, and a total length is approximately 660 nucleotides. Moreover, the 5'-end of the antibody light chain gene is connected to a leader sequence. In one embodiment, a forward primer (first primer) for the first stage PCR reaction is provided mid of the leader sequence. A forward primer (second primer) for the second stage PCR reaction is provided on the 5'-end region of the antibody light chain gene (V gene). Reverse primers (third and fourth primers) of the first stage and the second stage are provided on the 3'-end region of the antibody light chain gene (C gene).

In one embodiment, a nucleotide sequence of a region of the 5'-end primer (first primer) for the first stage PCR reaction, which region hybridizes with a template in the first stage PCR reaction, is AGCTTCTGGGGCTGCTAATG (SEQ ID NO: 43) or AGCTCCTGGGGCTGCTAATG (SEQ ID NO: 44). By designing the first primer as such, it is possible to selectively and efficiently amplify the antibody κ light chain gene having a Vκ gene that belongs to the subgroup II, by the two-stage PCR reaction. The following describes this reason.

FIG. 43 is a view illustrating a leader sequence of an antibody κ light chain gene having a Vκ gene that belongs to subgroup I, FIG. 44 is a view illustrating a leader sequence of an antibody κ light chain gene having a Vκ gene that belongs to subgroups II and III, and FIG. 45 is a view illustrating a leader sequence of an antibody κ light chain gene having a Vκ gene that belongs to subgroups IV to VI. FIGS. 43 to 45 shows homology with the first primer. In FIGS. 43 to 45, parts having a sequence identical to AGCTTCTGGGGCT-GCTAATG (SEQ ID NO: 43) described above are underlined. Parts corresponding to the first primer for each of the leader sequences are collectively shown in FIG. 46.

As illustrated in FIG. 44, the leader sequence of the antibody κ light chain gene having the Vκ gene that belongs to the subgroup II has a substantially identical nucleotide sequence to AGCTTCTGGGGCTGCTAATG (SEQ ID NO: 43) or AGCTCCTGGGGCTGCTAATG (SEQ ID NO: 44). Hence, it is possible to suitably amplify the antibody κ light chain gene having the Vκ gene that belongs to the subgroup II, by the PCR reaction using the first primer.

As illustrated in FIGS. 43 to 46, each of the leader sequences of the antibody κ light chain gene having the Vκ gene that belongs to its respective subgroup differ from the first primer (20 nucleotides) as follows: 2 to 3 nucleotides (subgroup I), at least 9 nucleotides (subgroup III), 14 nucleotides (subgroup IV), 12 nucleotides (subgroup V), and at least 8 nucleotides (subgroup VI). As such, just the leader sequence of the antibody κ light chain gene having the Vκ gene that belongs to the subgroup I has a close sequence, and the other leader sequences of the antibody κ light chain gene having the Vκ gene that belong to respective other subgroups each have sequences largely different from the first primer. Accordingly, by performing the two-stage PCR reaction, with use of the first primer having such a sequence as the 5'-end primer for the first stage PCR reaction, it is possible to selectively amplify the antibody light chain gene or its fragment, which antibody light chain gene has the Vκ gene that belongs to the subgroup II.

It should be noted that the nucleotide sequence of the first primer may slightly change. For example, a part corresponding to the first primer in the leader sequence of the antibody light chain gene having the Vκ gene that belongs to the subgroup II can be one whose 5th nucleotide from the 5'-end is T, as illustrated in FIG. 44. Accordingly, the 5th nucleotide from the left of the part represented by SEQ ID NO: 43 of the first primer may be changed to T. As described above, a polynucleotide that is specifically hybridizable with a polynucleotide represented by a sequence complementary to the nucleotide sequence of SEQ ID NO: 43 or SEQ ID NO: 44 may be used as the first primer for example, within a range that allows selectively and efficiently amplifying the antibody κ light chain gene having the Vκ gene that belongs to the first subgroup II. However, it is not preferable to add TC to the 5'-end or to add CT to the 3'-end, each of the nucleotide sequence of SEQ ID NO: 43 or SEQ ID NO: 44, as in the nucleotide sequence of SEQ ID NO: 47 disclosed in Patent Literature 1. This is because affinity with the leader sequence of the antibody light chain gene having the Vκ gene that belongs to the subgroup II increases, thereby causing the non-specific amplification to easily occur, as illustrated in FIG. 43. Moreover, it is expected that the antibody light chain gene having the Vκ gene that belongs to the subgroup II is easily amplified specifically, as illustrated in FIG. 44. From the above, it is particularly preferable that the region (sequence specific to the template) of the 5'-end primer (first primer) for the first stage PCR reaction, which region is hybridizable with the template in the first stage of the PCR reaction, be AGCTCCTGGGGCTGCTAATG (SEQ ID NO: 43) or AGCTTCTGGGGCTGCTAATG (SEQ ID NO: 44).

As such, the primer set according to the present embodiment allows for selectively and efficiently amplifying the antibody light chain gene or its fragment, which antibody light chain gene has the Vκ gene that belongs to the subgroup II, by use of a primer different from the primer disclosed in Patent Literature 1. Furthermore, the primer set according to the present embodiment is different from the primer set disclosed in Patent Literature 1, and includes the primer for a second stage. This allows for further selectively and efficiently amplifying the antibody light chain gene or its fragment, which antibody light chain gene has the Vκ gene that belongs to the subgroup II.

In one embodiment, the 5'-end primer (second primer) for the second stage PCR reaction can be any primer as long as it specifically hybridizes with an antibody light chain gene having a Vκ gene that belongs to the subgroup II or with a complementary strand that is a part of the leader sequence of the antibody light chain gene. However, it is preferable that the primer is specifically hybridizable with a complementary strand to GATRTTGTGATGACYCAG (SEQ ID NO: 45; where R is A or G, and Y is C or T) corresponding to the 5'-end region of the antibody light chain gene; for example, the primer may be one in which a nucleotide sequence of a region that is hybridizable with the template in the second stage PCR reaction is GATRTTGTGATGACYCAG (SEQ ID NO: 45). This allows for further selectively and efficiently amplifying the antibody light chain gene or its fragment, which antibody light chain gene has the Vκ gene that belongs to the subgroup II. The reason for this is described below.

FIG. 47 is a view illustrating approximately 60 nucleotides of the 5'-end side of the antibody κ light chain gene having the Vκ gene that belongs to the subgroup I, FIG. 48 is a view illustrating approximately 60 nucleotides of the 5'-end side of the antibody κ light chain gene having the Vκ gene that belongs to the subgroup II, and FIG. 49 is a view illustrating approximately 60 nucleotides on the 5'-end side of each of the antibody κ light chain genes having the Vκ gene that belongs to the subgroups III to VI. FIGS. 47 to 49 together show a homology with the second primer. In FIGS. 47 to 49, parts having a sequence identical to GATRTTGTGATGACYCAG (SEQ ID NO: 45) described above are underlined, and when the sequence is identical to one of selectable nucleotides, that part is further hatched. Parts corresponding to the second primer of each of the leader sequences are collectively shown in FIG. 50.

As shown in FIG. 48, a 5'-end of an antibody κ light chain gene having a Vκ gene that belongs to the subgroup II has a nucleotide sequence substantially identical to GATRTTGT-GATGACYCAG (SEQ ID NO: 45). Note that the 4th nucleotide from the 5'-end is A or G, and the 20th nucleotide is C or T. Hence, by the PCR reaction using the second primer, it is possible to suitably amplify the antibody κ light chain gene or its fragment, which antibody κ light chain gene has the Vκ gene that belongs to the subgroup II.

As shown in FIG. 47 and FIG. 50, the 5'-end of the antibody κ light chain gene having the Vκ gene that belongs to subgroup I differs by 4 nucleotides at the minimum from the second primer. Further, when R is made into G and Y is made into T, 6 nucleotides differ at the minimum. Hence, when the second stage PCR reaction is performed with use of the second primer, it is possible to prevent the antibody κ light chain gene having the Vκ gene that belongs to the subgroup I from amplifying non-specifically. Here, as described above, the first primer is close to the leader sequence of the antibody κ light chain gene having the Vκ gene that belongs to the subgroup I, however by performing the two-stage PCR reaction with use of the first primer and the second primer in combination, it is further possible to selectively and efficiently amplify the antibody light chain gene or its fragment, which antibody light chain gene has the Vκ gene that belongs to the subgroup II.

Moreover, as illustrated in FIGS. 48 to 50, the 5'-end of the antibody κ light chain gene having the Vκ gene that belongs to the subgroups III, IV, or VI have a substantially identical nucleotide sequence to the second primer, and the 5'-end of the antibody κ light chain gene having a Vκ gene that belongs to the subgroup V has a nucleotide sequence largely different from the second primer. As such, in a single stage PCR reaction with use of the second primer, it is difficult to successfully amplify the antibody light chain gene having the Vκ gene that belongs to the subgroup II, selectively.

As described above, by using the 5'-end primer (first primer) according to the present invention as the primer for the first stage PCR reaction of the two-stage PCR reaction and further performing the second stage PCR with use of any suitable primer, it is possible to selectively and efficiently amplify the antibody light chain gene or its antibody light chain gene, which antibody light chain gene has the Vκ gene that belongs to the subgroup II. Moreover, by use of the 5'-end primer (second primer) according to the present invention as the primer for the second stage PCR reaction of the two-stage PCR reaction, it is possible to further suitably selectively and efficiently amplify the antibody light chain gene or its fragment, which antibody light chain gene has the Vκ gene that belongs to the subgroup II.

As described above, the 5'-end primers (first and second primers) may have a restriction enzyme recognition site and a further nucleotide connected to its 5'-end. An example of such a first primer is a polynucleotide made up of the nucleotide sequence of AGTTCCATGGAGCTTCTGGGGCT-GCTAATG (SEQ ID NO: 9), and an example of such a second primer is a polynucleotide made up of the nucleotide sequence of AGTTCCATGGATRTTGTGATGACYCAG (SEQ ID NO: 11).

The 3'-end primers (third and fourth primer) for the first stage and the second stage of PCR may be any primer as long as that primer can amplify an antibody light chain gene having the Vκ gene that belongs to the subgroup II or a fragment that encodes its variable domain, in combination with the foregoing 5' end primer.

Examples of such a primer encompass, for example, a primer that specifically hybridizes with approximately 15 to 20 nucleotides of the 3'-end of a variable domain of the antibody light chain gene having the Vκ gene that belongs to the subgroup II, and a primer that specifically hybridizes with a part of a constant domain of the antibody κ light chain gene. Among these primers, it is preferable that the primer is one that specifically hybridizes with a part (e.g. a complementary strand of CTCGAGACACTCTCCCCTGTTGAAG (SEQ ID NO: 46)) of the 3'-end region of the antibody light chain gene (constant domain), and for example can be a primer whose a nucleotide sequence of a region hybridizable with a template in the PCR reaction is represented by CTCGAGA-CACTCTCCCCTGTTGAAG (SEQ ID NO: 46). When the third and fourth primers specifically hybridize with the 3'-end region of the antibody light chain gene (constant domain), it is possible to amplify the entire antibody light chain gene. However, it is considered that an abzyme made from the antibody light chain has a catalytic triad residues-like structure in its variable domain and therefore the catalytic activity of the abzyme is attributed to the variable domain. Hence, it is possible to achieve the object of the present invention, as long as it is possible to amplify a fragment that at least encodes the variable domain in the antibody light chain gene.

As described above, the 3'-end primers (third and fourth primers) may have a restriction enzyme recognition site and a further nucleotide connected to its 3'-end. An example of such third and fourth primers is a polynucleotide represented by the nucleotide sequence of ccgtCTCGAGACACTCTC-CCCTGTTGAAG (SEQ ID NO: 10).

[5. Production Method of Polynucleotide]

The present invention provides a production method of a polynucleotide. In one embodiment, the method according to the present invention of producing a polynucleotide includes a process of amplifying a polynucleotide that encodes at least a variable domain of a κ light chain of a human antibody from a human cDNA, by two-stage PCR reaction with use of the primer set described above. The design of the used primer, a condition of the PCR reaction, the template cDNA and the like, are all as described above.

After the process of amplifying, a reaction product of the two-stage PCR reaction can be confirmed as to, for example, whether or not the polynucleotide has a desirable length, by a publicly known method (e.g. agarose gel electrophoresis). The reaction product that has been confirmed in its desirable length, for example, can be purified and introduced into a subcloning vector that is used for sequencing. The reaction product introduced into the subcloning vector may be confirmed as to which germline gene the subcloning vector is derived from, by sequence analysis and homology search.

With the method according to the present embodiment, it is possible to amplify an antibody light chain gene having a Vκ gene that belongs to the subgroup II or a polynucleotide which is a fragment of the antibody light chain gene, by a percentage near 100%. By amplifying the antibody light chain gene or its fragment, which antibody light chain gene has the Vκ gene that belongs to various subgroups II, it is possible to express an abzyme which either has a high activity or acts with various substrates. Here, although not limited in particular, it is preferable that the enzyme activity that the abzyme has is protease activity or peptitase activity.

[6. Production Method of Polypeptide]

A polynucleotide produced by the method according to the present invention of producing a polynucleotide is an antibody light chain gene having a Vκ gene that belongs to the subgroup II, or is its fragment that encodes at least a variable domain. Hence, it is possible to introduce this into an appropriate host (e.g. bacterium, yeast), to express the antibody light chain having the Vκ gene that belongs to the subgroup II, or its fragment that at least includes the variable domain.

The introduction of the polynucleotide uses a method of, for example, preparing a recombinant expression vector that contains the polynucleotide, and introducing it into a host cell. The preparation of the recombinant expression vector may use a plasmid, phage, cosmid or the like, however it is not limited in particular. A specific kind of vector is not limited in particular, and a vector that is expressible in a host cell is selected as appropriate. Namely, a promoter sequence is selected as appropriate to positively express a gene depending on the kind of host cell, and is incorporated with the polynucleotide into various plasmids or the like to be used as an expression vector.

In order to confirm whether or not the polynucleotide is introduced into the host cell, and further to confirm whether or not the polynucleotide is positively being expressed in the host cell, various markers may be used. For example, a gene deleted in the host cell may be used as a marker; a plasmid or the like including this marker and the gene of the present invention is introduced into the host cell as the expression vector. This allows for confirming the introduction of the gene of the present invention, by the expression of the marker gene.

The host cell is not limited in particular, and various conventionally known cells may be suitably used. More specifically, examples of the host cell in the case of a gene having a full length DNA as described in [2: Gene according to the present invention] encompass, human or mouse-derived cells, and further a nematode, an oocyte of *Xenopus laevis*, culture cells of various mammals (rat, rabbit, pig, monkey, etc.), or animal cells such as culture cells of insects such as *Drosophila melanogaster* or silkworm moth. As a host cell in the case of a DNA fragment, examples encompass bacteria such as *Escherichia coli*, yeast (budding yeast and fission yeast) and the like, however it is not limited in particular.

A method of introducing the expression vector into a host cell, that is, a transformation method, is not limited in particular, and conventionally known methods may be suitably used, for example electroporation, calcium phosphate method, liposome method, or DEAE dextran method.

The polynucleotide introduced into the host cell may be expressed by IPTG induction, or like method.

[6. Summary]

An antiviral agent according to the present invention is an antiviral agent comprising a human antibody κ light chain consisting of a polypeptide having a variable domain represented by the amino acid sequence shown in SEQ ID NO: 14, 26, 22, 30, 50, 54, or 35.

The antiviral agent according to the present invention is preferably configured such that the human antibody κ light chain is a monomer.

Conventionally, a neutralization antibody against rabies virus is a tetramer consisting of two light chains and two heavy chains, like natural antibodies. The neutralization antibody expresses its neutralization activity by binding to the rabies virus. A technique using monomeric κ light chain has not been known conventionally, and it could not be expectable for a person skilled in the art to obtain a high anti virus activity by solely using such monomeric κ light chain.

It is preferable in the antiviral agent according to the present invention that the amino acid sequence of the human antibody κ light chain is modified such that cysteine forming a disulfide bonding with another light chain is deleted or substituted with another amino acid than cysteine. The antiviral agent according to the present invention may be configured such that the human antibody κ light chain consists of a polypeptide represented by the amino acid sequence shown in SEQ ID NO: 15, 27, 31, 51, 55, or 36. These configurations make it possible to provide the monomeric κ light chain having a high anti virus activity.

It is preferable in the antiviral agent according to the present invention that the virus is an minus single-strand RNA virus. As described in Examples later, the antiviral agent according to the present invention is highly effective against an minus single-strand RNA virus ((−)ssRNA virus).

The antiviral agent according to the present invention may be configured such that the variable domain consists of a polypeptide represented by the amino acid sequence shown in SEQ ID NO: 14, 26, 22 or 30; and the virus is a virus belonging to Rhabdoviridae. When the variable domain consists of such a polypeptide, the antiviral agent is highly effective against rhabdovirus, such as rabies virus and vesicular stomatitis virus, as described in Examples later.

The antiviral agent according to the present invention may be configured such that the variable domain consists of a polypeptide represented by the amino acid sequence shown in SEQ ID NO: 14, 26, 50, 54 or 35; and the virus is an influenza virus. When the variable domain consists of such a polypeptide, the antiviral agent is highly effective against influenza viruses as described in Examples later.

The present invention also provides a human abzyme being a human antibody κ light chain against rabies virus and having an enzyme activity.

That is, a human abzyme according to the present invention may be: (i) a human abzyme being a human antibody κ light chain against rabies virus and having an amidase activity and a variable domain consisting of a polypeptide represented by the amino acid sequence shown in SEQ ID NO: 14, 26, 16, 18, 30, 35, or 40; (ii) a human abzyme being a human antibody κ light chain against rabies virus and having a nucleolytic activity and a variable domain consisting of a polypeptide represented by the amino acid sequence shown in SEQ ID NO: 14, 26, 30, 50, or 54; (iii) a human abzyme being a human antibody κ light chain against rabies virus and cytotoxic to cancer cells, and having a variable domain consisting of a polypeptide represented by the amino acid sequence shown in SEQ ID NO: 14, or 30; (iv) a human abzyme being a human antibody κ light chain against rabies virus and having an anti virus activity and a variable domain consisting of a polypeptide represented by the amino acid sequence shown in SEQ ID NO: 14, 26, 22, 30, 50, 54, or 35. These abzymes are human abzymes and considered to produce no or little side effect when administered to humans.

It is preferable in the human abzyme according to the present invention that the human antibody κ light chain is such that cysteine for forming a disulfide bond with another light chain is deleted or substituted with an amino acid or amino acids other than cysteine. The human abzyme according to the present invention may be such that the κ light chain consists of a polypeptide represented by the amino acid sequence shown in SEQ ID NO: 15, 27, 17, 19, 31, 36, 41, 23, 51, or 55. With these configurations, it is possible to easily provide a human abzyme being a monomeric κ light chain, which shows a high activity.

The present invention also provides a polynucleotide according to the present invention for encoding the human antibody κ light chain. Moreover, the present invention also provides a vector containing the polynucleotide according to the present invention, and a transformant in which the polynucleotide according to the present invention is introduced.

The present invention encompasses the following inventions as a matter of course.

A polypeptide according to the present invention is a polypeptide being a polypeptide (A) represented by the amino acid sequence shown in SEQ ID NO: 1, 3, 5 or 7; or a polypeptide (B) in which one or several amino acids are substituted, deleted, or added in the amino acid sequence represented by the amino acid sequence shown in SEQ ID NO: 1, 3, 5 or 7, and which has amidase activity.

It is preferable that the polypeptide is a human antibody κ light chain.

A polynucleotide according to the present invention is a polynucleotide for encoding a polypeptide according to the present invention.

The polynucleotide according to the present invention may be: a polynucleotide (A) represented by the nucleotide sequence shown in SEQ ID NO: 2, 4, 6, or 8; a polynucleotide (B) in which one or several nucleotides are substituted, deleted, or added in the nucleotide sequence shown in SEQ ID NO: 2, 4, 6, or 8, and which encodes a human antibody κ light chain having an amidase activity; or a polynucleotide (C) hybridizable, under a stringent condition, with a complementary chain represented by the nucleotide sequence shown in SEQ ID NO: 2, 4, 6, or 8, and which encodes a human antibody κ light chain having an amidase activity.

A vector according to the present invention is a vector containing a polynucleotide according to the present invention.

A transformant according to the present invention is a transformant in which a polynucleotide according to the present invention is introduced.

An abzyme according to the present invention is a human antibody κ light chain or a fragment thereof, has a variable domain represented by the 1st to 113th amino acids in the amino acid sequence shown in SEQ ID NO: 1, the 1st to 113th amino acids in the amino acid sequence shown in SEQ ID NO: 3, or the 1st to 112th amino acids in the amino acid sequence shown in SEQ ID NO: 5, and has an amidase activity.

An antiviral agent according to the present invention contains a polypeptide according to the present invention or an abzyme according to the present invention.

The antiviral agent according to the present invention is preferably an antiviral agent against a virus belonging to Rhabdoviridae. It is more preferable that the virus is rabies virus or vesicular stomatitis virus.

A primer set according to the present invention being a primer set for amplifying a polynucleotide for encoding at least a variable domain of a human antibody κ light chain via two-stage PCR reaction using a human cDNA as a template, comprising: a first primer for first-stage PCR reaction, the first primer being a polynucleotide having a domain hybridizable with the template in the first stage PCR reaction, the domain being represented by the nucleotide sequence shown in SEQ ID NO: 43 or 44.

By using the primer set according to the present invention, it is possible to selectively and effectively amplify, in human cDNA, a fragment for encoding (i) antibody light chain cDNA having Vκ gene belonging to the subgroup II or (ii) at least the variable domain thereof. This makes it possible to effectively obtain the human antibody κ light chain, which is an abzyme.

The primer set according to the present invention preferably comprises: a second primer for second-stage PCR reaction, the second primer being a polynucleotide hybridizable specifically with a polynucleotide represented by a complementary sequence for the nucleotide sequence shown in SEQ ID NO: 45.

As one alternative, a primer set according to the present invention is a primer set for amplifying a polynucleotide for encoding at least a variable domain of a human antibody κ light chain via two-stage PCR reaction using a human cDNA as a template, comprising: a first primer for first-stage PCR reaction, the first primer being a polynucleotide hybridizable specifically with a poly nucleotide represented by a complementary sequence for the nucleotide sequence shown in SEQ ID NO: 43 or 44; and a second primer for second-stage PCR reaction, the second primer being a polynucleotide hybridizable specifically with a poly nucleotide represented by a complementary sequence for the nucleotide sequence shown in SEQ ID NO: 45.

Moreover, the primer set according to the present invention preferably further comprises: a third primer for the first-stage PCR reaction, the third primer being a polynucleotide hybridizable specifically with part of a gene sequence of a constant domain of the human antibody κ type light chain; and a fourth primer for the second-stage PCR reaction, the fourth primer being a polynucleotide hybridizable specifically with part of the gene sequence of the constant domain of the human antibody κ type light chain. It is preferable in the primer set according to the present invention that the third primer is a polynucleotide hybridizable specifically with a polynucleotide represented by a complementary sequence for the nucleotide sequence shown in SEQ ID NO: 46; and the fourth primer is the polynucleotide hybridizable specifically with the polynucleotide represented by the complementary sequence for the nucleotide sequence shown in SEQ ID NO: 46.

The primer set according to the present invention may be such that the human cDNA is derived from a lymph cell.

The present invention encompasses (i) a method for producing a polynucleotide, the method comprising: performing two-stage PCR reaction by using a primer set according to the present invention, so as to amplify the polynucleotide for encoding at least the variable domain of the human antibody κ light chain from human cDNA, and (ii) a method for producing a polypeptide, the method comprising: producing a polynucleotide by the above method; and expressing the polynucleotide inside a host cell.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

EXAMPLES

Clone Preparation by Uniquely-Developed Two-Stage PCR Reaction (1-1. Designing Primer)

As illustrated in FIG. 1, a forward primer and a reverse primer for the first-stage PCR reason, and a forward primer and a reverse primer for the second-stage PCR reaction were designed.

The inventors of the present invention analyzed details of properties and structural characteristics of human-derived abzyme having an activity to cleave or decompose peptides and antigen proteins. As a result of the analysis, the inventors demonstrated that serine residue, aspartyl residue, and histidine residue exist closely to each other in the steric structure of "the abzyme having an activity to cleave or decompose peptides or antigen proteins". Here, what is meant by "existing closely to each other" is the serine residue, aspartyl residue, and histidine residue exist within a distance of at most 3 Å to 20 Å, preferably of 3 Å to 10 Å. Hereinafter, the structure in which the three amino acid resides exit closely to each other is referred to as "catalytic triad residue-like structure". It is deduced that the catalytic triad residue-like structure and the substrate (a peptide or an antigen protein) react with each other sufficiently, when the distance between the three amino acid residues is within the range of at most 3 Å to 20 Å, preferably of 3 Å to 10 Å.

The antibody has a heavy chain (H chain) and a light chain (L chain). The heavy chain and the light chain is composed of a variable domain (VR) and a constant domain (CR). The variable domain includes a complimentarity determining region (CDR). Further, the light chain of the antibody is classified into a κ type and a λ type.

The antibody gene encodes the variable domain and the constant domain. A structural gene of the variable domain of the light chain is composed of a V gene and a J gene. Because each germline gene encodes a different amino acid sequence, each antibody produced from the gene has a different sequence depending on the structural gene in the variable domain constituting the antibody gene. This accounts for diversity of the antibody. The germline genes are classified into sub groups based on their nucleotide sequences.

The inventors of the present invention proved that the polypeptide encoded from the V gene of κ type light chain belonging to the subgroup II (V κ gene of the subgroup II) has the triad residue-like structure highly frequently (see, for example, Patent Literature 1). From this, it is expected that a useful human abzyme can be obtained especially in case where an enzyme activity is attained due to a triad residue-like structure formed in a variable domain constituting a bonding site for bonding with an antigen.

However, because the subgroups of V κ genes are very similar in sequence, it has been very difficult to specifically design a primer for amplifying an antibody light chain gene having a V κ gene belonging to the subgroup II. The inventors of the present invention found through try-and-error works that two-stage PCR reaction using a primer having a later-described nucleotide sequence can effectively amplify such an antibody light chain gene having a V κ gene belonging to the subgroup II.

(1-2. Preparation of Human Peripheral Blood cDNA)

From a peripheral blood sample obtained from a volunteer hyperimmunized by being immunized plural times with a vaccine for rabies virus, lymph cells were isolated by using Ficoll-paque. By using a RNA extraction kit (Stratagene), a total RNA was obtained from about $3.0 \times 10^7$ lymph cells thus isolated. By using TheromoScript RT-PCR System (Invitrogen), reverse transcription of the total RNA was performed with oligo (dt) as a primer, so as to prepare cDNA (cDNA library) as desired.

(1-3. First-Stage PCR Reaction)

First state PCR reaction was performed with, as a template, the human peripheral blood cDNA thus prepared in 1-2. As a forward primer, an oligonucleotide having the nucleotide sequence agttCCATGGAGCTTCTGGGGCTGCTAATG (SEQ ID NO: 9) was used, in which the 5th to 10th nucleotides (CCATGG) are a restriction enzyme site. As a reverse primer, an oligonucleotide having the nucleotide sequence ccgtCTCGAGACACTCTCCCCTGTTGAAG (SEQ ID NO: 10) was used, in which the 5th to 10th nucleotides (CTCGAG) are a restriction enzyme site. Details of the primers are shown in Table 1.

TABLE 1

| TYPE/NAME | NUCLEOTIDE SEQUENCE |
|---|---|
| Forward/HukNcoI20L-2 | agtt<u>CCATGG</u>AGCTTCTGGGGCTGCTAATG |
| Reverse/HukIIChoI203' | ccgt<u>CTCGAG</u>ACACTCTCCCCTGTTGAAG | underlined: Restriction enzyme site
half-toned: Sequence specific to cDNA

The PCR reaction was carried out in a PCR tube with a reaction liquid of 20.0 μl in total. The reaction liquid had been prepared by adding 0.2 μl of Phusion DNA polymerase to a mixture of the human peripheral blood cDNA (0.5 μl), 5× Phusion HF buffer (4.0 μl), 10 mM dNTPs (0.4 μl), 10 μM reverse primer (0.8 μl), 10 μM forward primer (0.8 μl), a sterilized mili Q water (13.3 μl).

The thermal cycles were as follows: 98° C. for 30 seconds ⇒ repeating (1) 98° C. for 10 sections ⇒ (2) 60° C. for 30 seconds ⇒ (3) 72° C. for 30 sections (30 cycles) ⇒ 72° C. for 5 minutes, ⇒ maintained at 4° C.

Figure 2:
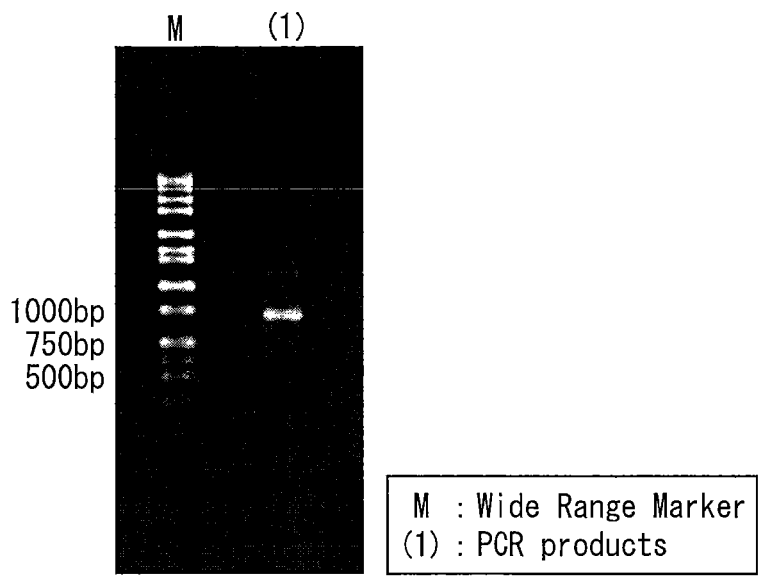
FIG. 2 shows a result of SDS-PAGE after a first stage of PCR reaction

The reaction liquid having been subjected to the PCR reaction was electrophoresed with 2% agarose gel (NuSieve GTG agarose). In the electrophoresed gel then stained with EtBr and UV-irradiated, a band indicting amplification of a desired gene was observed at about 750 bp (FIG. 2).

From the gel, the PCR product was purified by using a phenol chloroform method.

(1-4. Second-Stage PCR Reaction)

In the second-stage PCR reaction, the PCR product of the first-stage PCR reaction obtained in 1-3. was used as a template. As a forward primer, an oligonucleotide having the nucleotide sequence of agttCCATGGATRTTGTGATGACYCAG (SEQ ID NO: 11) was used, in which the 5th to 10th nucleotides (CCATGG) are a restriction enzyme site. As a reverse primer, an oligonucleotide having the nucleotide sequence of ccgtCTCGAGACACTCTCCCCTGTTGAAG (SEQ ID NO: 10) was used, in which the 5th to 10th nucleotides (CTCGAG) are a restriction enzyme site. Details of the primer are shown in Table 2.

TABLE 2

| TYPE/NAME | NUCLEOTIDE SEQUENCE |
|---|---|
| Forward/ HukNcoI205'-2 | agtt<u>CCATGG</u>ATRTTGTGATGACYCAG |
| Reverse/HukIIChoI203 | ccgt<u>CTCGAG</u>ACACTCTCCCCTGTTGAAG | underlined: Restriction enzyme site
half-toned: Sequence specific to cDNA

The PCR reaction was carried out in a PCR tube with a reaction liquid of 20.0 μl in total. The reaction liquid had been prepared by adding 0.2 μl of Phusion DNA polymerase to a mixture of the first-stage PCR product obtained in 1-3. (diluted to 1/10 or 1/100) (0.5 μl), 5× Phusion HF buffer (4.0 μl), 10 mM dNTPs (0.4 μl), 10 μM reverse primer (0.8 μl), 10 μM forward primer (0.8 μl), a sterilized mili Q water (13.3 μl).

The thermal cycles were as follows: 98° C. for 30 seconds ⇒ repeating (1) 98° C. for 10 sections ⇒ (2) 60° C. for 30 seconds ⇒ (3) 72° C. for 30 sections (30 cycles) ⇒ 72° C. for 5 minutes, ⇒ maintained at 4° C.

Figure 3:
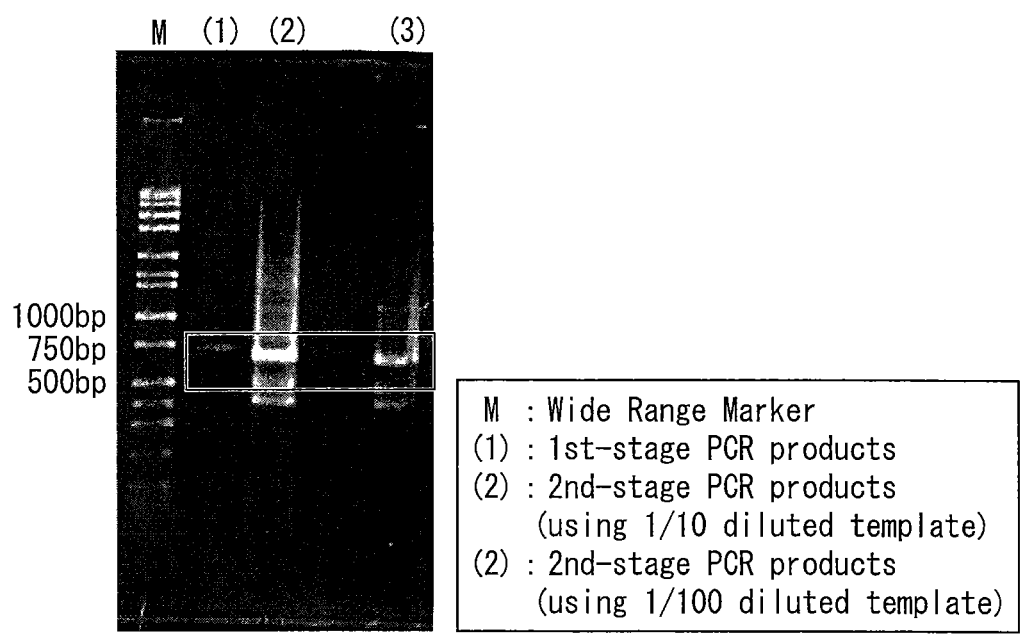
FIG. 3 shows a result of SDS-PAGE after a second stage of PCR reaction.

The post-amplification PCR product was detected by electrophoresis with 2% agarose gel (NuSieve GTG agarose), in the same way as in 1-3. As shown in FIG. 3, a band indicating amplification of the desired gene was observed around 750 bp. FIG. 3 demonstrates that the second-stage PCR products using 1/10-diluted template and using 1/100-diluted template have shorter bands than that of the first-stage PCR product.

From the gel, the PCR product was purified by using a phenol chloroform method.

(1-5. Insertion into Vector)

The PCR products (K type light chain gene belonging to the subgroup II) at about 750 pb obtained via the two-stage PCR reactions in 1-4. was inserted into a pCR Blunt II-TOPO. A reaction liquid of 2.5 μl in total was prepared from the PCR product (about 750 bp) (0.5 μl), saline solution (0.5 μl), mili Q water (1.5 μl), and TOPO vector (0.5 μl), and then reacted at 23° C.

(1-6. Transformation of E. coli)

To 33.3 μl of competent cells (DH5α), 2 μl of the TOPO vector cloned with the κ light chain gene belonging to the subgroup II was added. After that, the competent cells and the TOPO vector were let stand in an ice bath for 10 minute. Then the competent cells and the TOPO vector are subjected to 45-second heat shock in a 42° C. water bath. Immediately after that, the competent cells and the TOPO vector were returned in the ice bath and let stand for 2 min therein. After 300 ml of SOC medium was then added thereto in a clean bench, the competent cells and the TOPO vector were incubated at 37° C. for 1 min under vibration (reviving culturing).

The culture liquid after the reviving culturing was smeared on a 2×YT (KM+) solid medium, which have been kept warm. Then, the medium was incubated at 37° C. overnight.

(1-7. Confirmation of Insert)

Figure 4:
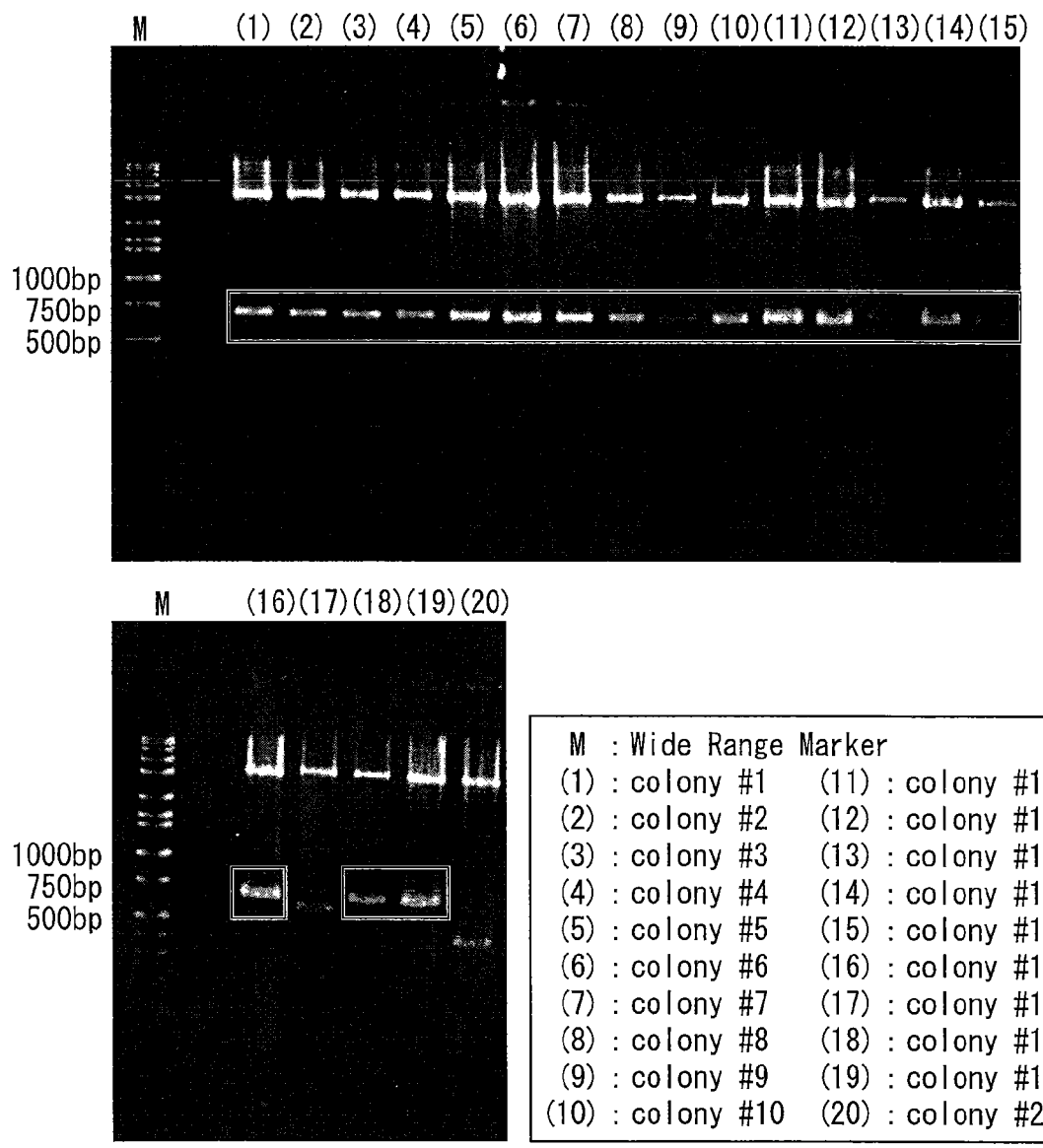
FIG. 4 shows a result of SDS-PAGE for identifying reaction products developed by two steps of PCR reaction.

For 20 colonies (colonies #1 to #20), whether the insertion was successful or not. Firstly, plasmid was collected from a microorganism body by using a standard method in the art. A reaction liquid of 15.0 μl in total was prepared from the collected plasmid (1.0 μl), 10× buffer (1.5 μl), Eco RI (0.3 μl), and sterilized mili Q water (12.2 μl). The reaction liquid was subjected to restriction enzyme reaction at 37° C. overnight, and then electrophoresis with 2% agarose gel (NuSieve GTG agarose). As illustrated in FIG. 4, insertion of the desired gene was confirmed in the colonies #1 to #16, #18, and #19. Hereinafter, these colonies are referred to as clones #1 to #16, #18, and #19.

(1-8. Sequence Analysis and Germline Gene Identification)

Sequence analysis was carried out for clones #1 to #16, #18, and #19. Then, a V κ gene in each germline gene was determined by homology search. Results thereof are shown in Table 3. It was found that all the 18 clones belonged to the subgroup II.

TABLE 3

| Germline gene to which the clones belong | |
|---|---|
| | original germline gene |
| #1 | A18b |
| #2 | A3/A19 |
| #3 | A3/A19 |
| #4 | O11/o1 |
| #5 | A3/A19 |
| #6 | A18b |
| #7 | A3/A19 |
| #8 | A18b |
| #9 | A18b |
| #10 | A18b |
| #11 | A18b |
| #12 | A3/A19 |
| #13 | A3/A19 |
| #14 | A3/A19 |

TABLE 3-continued

Germline gene to which the clones belong

| | original germline gene |
|---|---|
| #15 | A5 |
| #16 | A17 |
| #18 | A18b |
| #19 | A17 |

As to the clone #1 (germline gene: A18b), the clone #16 (germline gene: A17), the clone #7 (germline gene: A3/A19), and the clone #11 (germline gene: A18b), parts of the amino acid sequences deduces from the results of the sequencing are shown in (a) to (d) of FIG. 5. As to the amino acid sequences deduced from the results of the sequencing for the other clones, see FIGS. 39 and 40. The amino acid sequences shown in FIGS. 39 and 40 are such that they have methionine at the starting end, and that the end terminal cysteine thereof is substituted with alanine, and leucine and histidine are added to the terminal. A person skilled in the art will easily understand that the amino acid sequence of the antibody light chain can be easily obtained from the sequences by removing methionine from the starting end and substituting the terminal ALEHHHHHH with C. FIGS. 39 and 40 show the variable domain, constant domain, and the positions of CDR1 to 3.

In more details, the whole nucleotide sequence of the clone #1 is the one shown in SEQ ID NO: 2, and deduced to encode the amino acid sequence of SEQ ID NO: 1. In the amino acid sequence of SEQ ID NO: 1, the 1st to 113th amino acids constitute the variable domain. Among them, the 24th to 39th amino acids are CDR1, the 55th to 60th amino acids are CDR2, and the 94th to 103th amino acids are CDR3. Only the amino acids in the variable domain are shown in SEQ ID NO: 14.

The whole nucleotide sequence of the clone #16 is the one shown in SEQ ID NO: 4, and deduced to encode the amino acid sequence of SEQ ID NO: 3. In the amino acid sequence of SEQ ID NO: 3, the 1st to 113th amino acids constitute the variable domain. Among them, the 24th to 39th amino acids are CDR1, the 55th to 60th amino acids are CDR2, and the 94th to 103th amino acids are CDR3. Only the amino acids in the variable domain are shown in SEQ ID NO: 16.

The whole nucleotide sequence of the clone #7 is the one shown in SEQ ID NO: 6, and deduced to encode the amino acid sequence of SEQ ID NO: 5. In the amino acid sequence of SEQ ID NO: 5, the 1st to 112th amino acids constitute the variable domain. Among them, the 24th to 39th amino acids are CDR1, the 55th to 60th amino acids are CDR2, and the 94th to 102th amino acids are CDR3. Only the amino acids in the variable domain are shown in SEQ ID NO: 18.

The whole nucleotide sequence of the clone #6 is the one shown in SEQ ID NO: 21 and deduced to encode the amino acid sequence of SEQ ID NO: 20. In the amino acid sequence of SEQ ID NO: 20, the 1st to 112th amino acids constitute the variable domain. Among them, the 24th to 39th amino acids are CDR1, the 55th to 60th amino acids are CDR2, and the 94th to 102th amino acids are CDR3. Only the amino acids in the variable domain are shown in SEQ ID NO: 22.

The whole nucleotide sequence of the clone #18 is the one shown in SEQ ID NO: 25 and deduced to encode the amino acid sequence of SEQ ID NO: 24. In the amino acid sequence of SEQ ID NO: 24, the 1st to 112th amino acids constitute the variable domain. Among them, the 24th to 39th amino acids are CDR1, the 55th to 60th amino acids are CDR2, and the 94th to 102th amino acids are CDR3. Only the amino acids in the variable domain are shown in SEQ ID NO: 26.

(1-9. Transformation by Heat Shock)

The clones #1, #16, #7, and #11 were introduced in plasmids having a His tag sequence site, respectively. Then, 1 µl of the plasmid DNA adjusted to 5 ng/µL was added to BL21 (DE3) pLysS of 50 µL melted on ice, and let stand for 5 min on ice. Then, the plasmid DNA was incubated for 30 sec in a water bath of 42° C., and then let stand on ice for 2 min or longer. Then, SOC medium of 250 µL warmed at 37° C. was added thereto in a clean bench. Then, thus prepared culture liquid was transferred into a round tube and incubated at 37° C. under vibration of 200 rpm (reviving culturing). After the reviving culturing, 50 µL or 10 µL of the culture liquid was introduced in a plate and incubated at 37° C. overnight. Then, colonies formed on the plate were counted.

(a) of FIG. 6 is a view illustrating a plate with the culture liquid of 50 µL. (b) of FIG. 6 is a view illustrating a plate with the culture liquid of 50 µL. As illustrated therein, 5 colonies were formed on the plate with the culture liquid of 50 µL, and transformation efficiency was $7.2 \times 10^3$ pfu/g DNA. Meanwhile, 35 colonies were formed on the plate with the culture liquid of 100 µL, and transformation efficiency was $2.1 \times 10^4$ pfu/g DNA.

(1-10. Transformation by Electroporation)

Apart from the transformation by the heat shock in 1-9, transformation by electroporation was conducted. After 5 µL of the plasmid was added to the competent cells of 50 µL, the plasmid and the competent cells were quickly transferred to a cuvette and left stand on ice for 1 min. Then, by placing the cuvette on an electropolator, which was set to 2.5 kV, pulses were applied thereon. Right after that, 450 µL of SOC medium was added therein and then shaken. The content in the cuvette was transferred in 2-mL tube and incubated at 37° C. for 1 hour under vibration.

(1-11. Protein Expression Induction (Pre-Culturing and Main Culturing) and SDS-PAGE Analysis)

In a test tube, 3 mL of LB medium and 6 µL of ampicillin (final concentration 100 µg/mL) was introduced. From glycerol stock thereof, the transformed microorganism was inoculated in the test tube by using a bamboo skewer, and incubated therein at 37° C. overnight. After the pre-culturing, 5 mL of LB medium and 5 µL of ampicillin (final concentration 5 ng/mL) were introduced in a test tube. Into the test tube, the pre-cultured culture liquid was transferred in an amount of 50 µL, which was 1/100 of the LB medium. The test tube was incubated 25° C. for the main culturing, which was continued until O.D.$_{660}$ reached a value in a range of 0.6 to 0.8, approximately. After the O.D.$_{660}$ approximately reached a value in a range of 0.6 to 0.8, 0.1 M of IPTG 50 µL was introduced in the test tube, which was then further incubated at 37° C. for 6 hours. After that, the culture liquid in the test tube was transferred in a 5-mL tube and centrifuged for 10 min at 4° C. 18000×g. The medium (supernatant) was transferred into falcon tube by decantation. Moreover, the microorganisms (pellet) were added with 1×PBS and suspended by using a pipette. Then, the microorganisms were transferred in another falcon tube. The medium and the microorganisms were separately stored by freezing.

Figure 7:
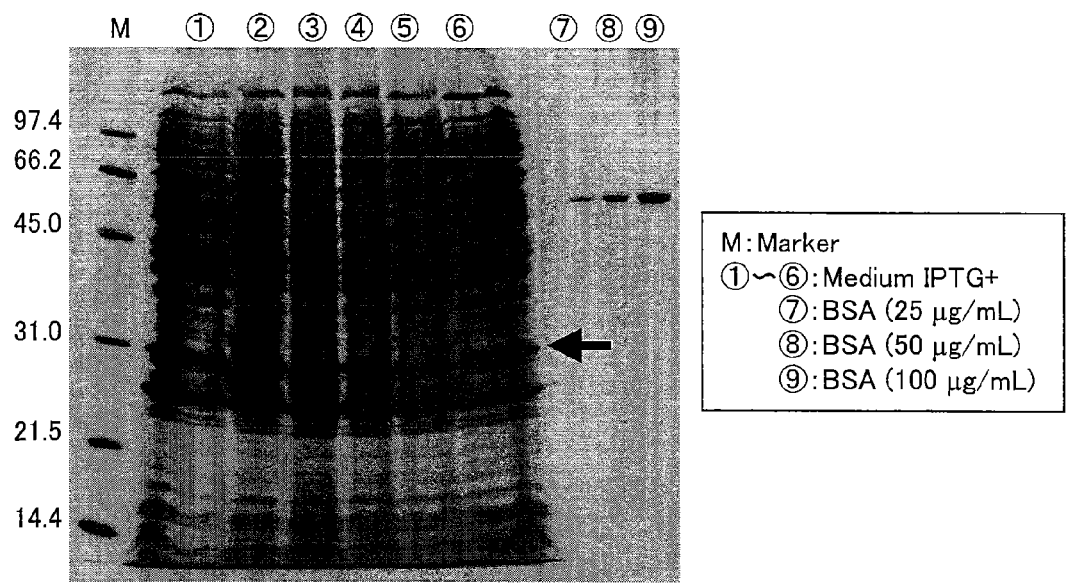
FIG. 7 shows expressed protein in the transformed E. coli under induction of expression.
Figure 8:
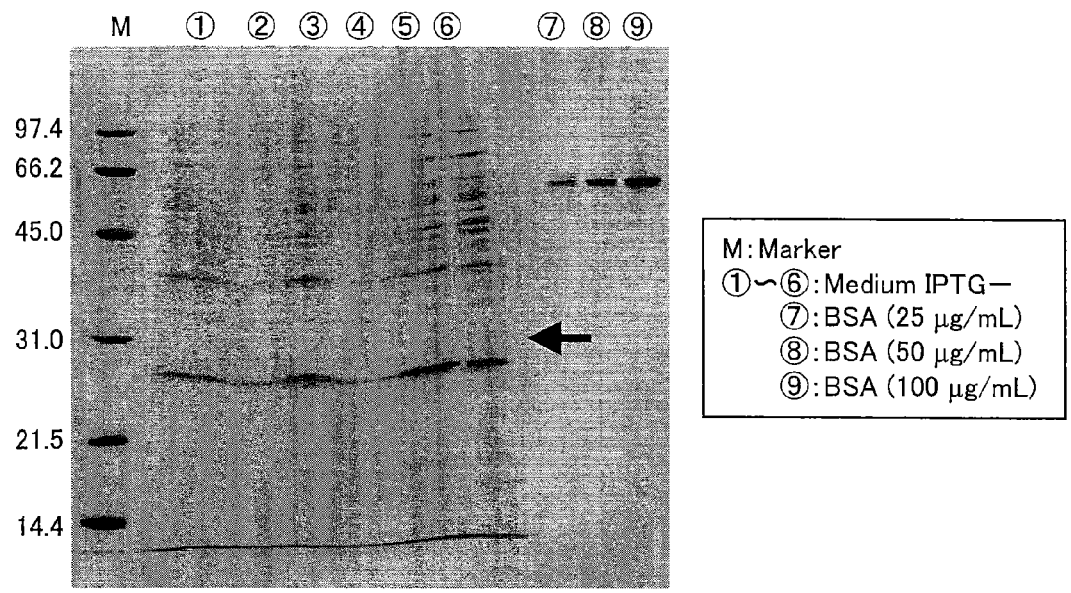
FIG. 8 shows expressed protein in the transformed E. coli not under induction of expression.

With (+) or without (−) the IPTG induction, expression of the desired protein in the medium was confirmed by SDS-PAGE and coomassie staining. Results of the confirmation are shown in FIGS. 7 and 8. FIG. 7 is a view illustrating the result of the SDS-PAGE analysis of the microorganism suspension in which IPTG was added (+). FIG. 8 is a view illustrating the result of the SDS-PAGE analysis of the microorganism suspension in which IPTG was not added (−). The κ type light chain of the antibody had a theoretical molecular weight of about 24 kDa. However, because the S—S bonding was cleaved by the reduction condition, a band appeared at about 31 kDa. In FIGS. 7 and 8, the position at which the band of the κ type light chain is indicated by an arrow.

As illustrated in FIG. 7, expression of the desired protein was confirmed in the case of the IPTG induction (+). Concentration of the band of the desired protein in each sample is equivalent to that of the band BSA (concentration 100 μg/ml, 10 μl) of lane 9. Thus, it is deduced that the concentrations in the samples were 1 μg/1 ml. As illustrated in FIG. 8, no expression of the desired protein was confirmed in the case of no IPTG induction (−).

(1-12. Collection of Soluble Fraction and Insoluble Fraction of the Microorganisms, and SDS-PAGE Analysis)

The suspension of the microorganism obtained in 1-11 was repeatedly frozen and thawed with liquid nitrogen until the suspension became non-viscous. Then, the suspension was centrifuged for 25 min at 4° C. at 14000 rpm. Pellet and supernatant thus obtained were collected as the insoluble fraction and soluble fraction, respectively. To the insoluble fraction, a sump buffer was added so as to dissolve the pellet.

Figure 9:
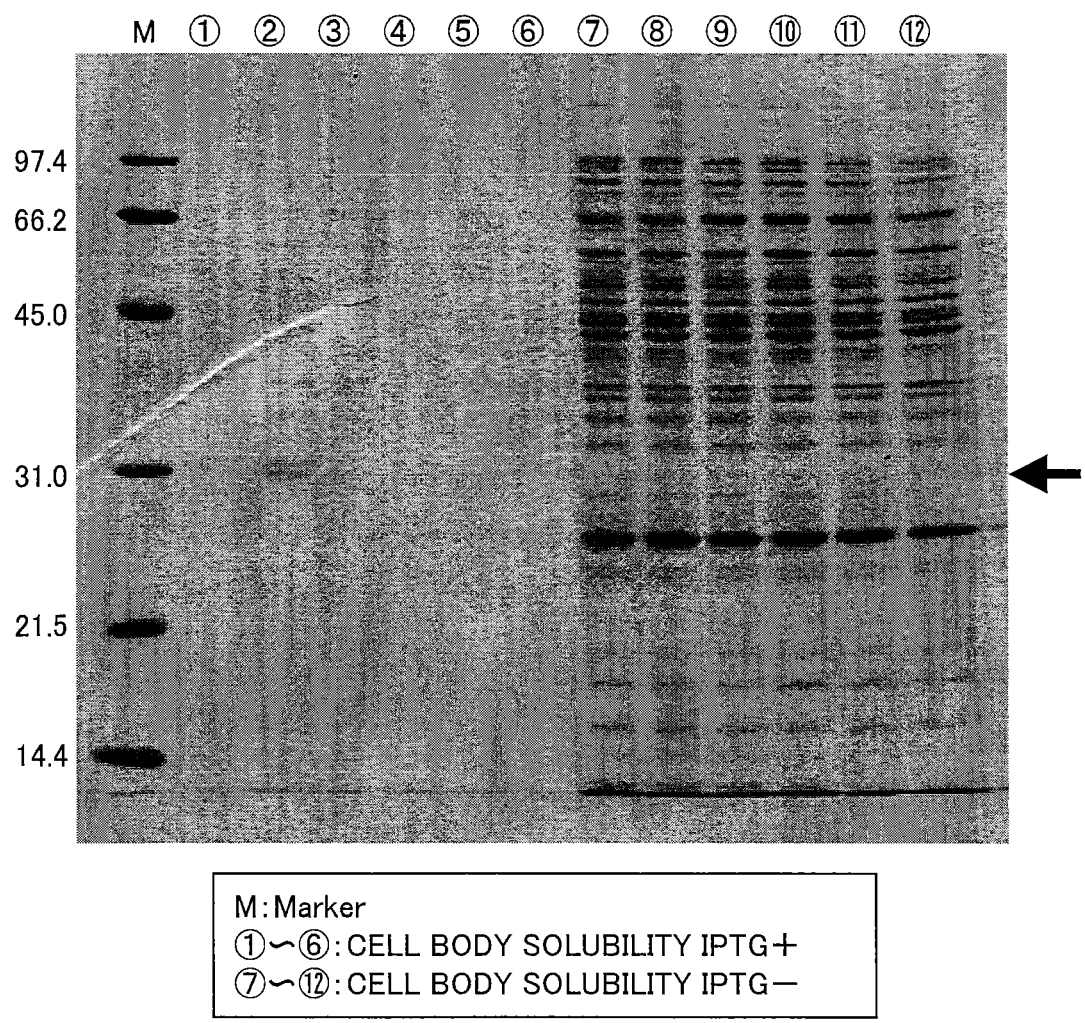
FIG. 9 shows expressed protein in a soluble fraction of a bacterial cell in the transformed E. coli.
Figure 10:
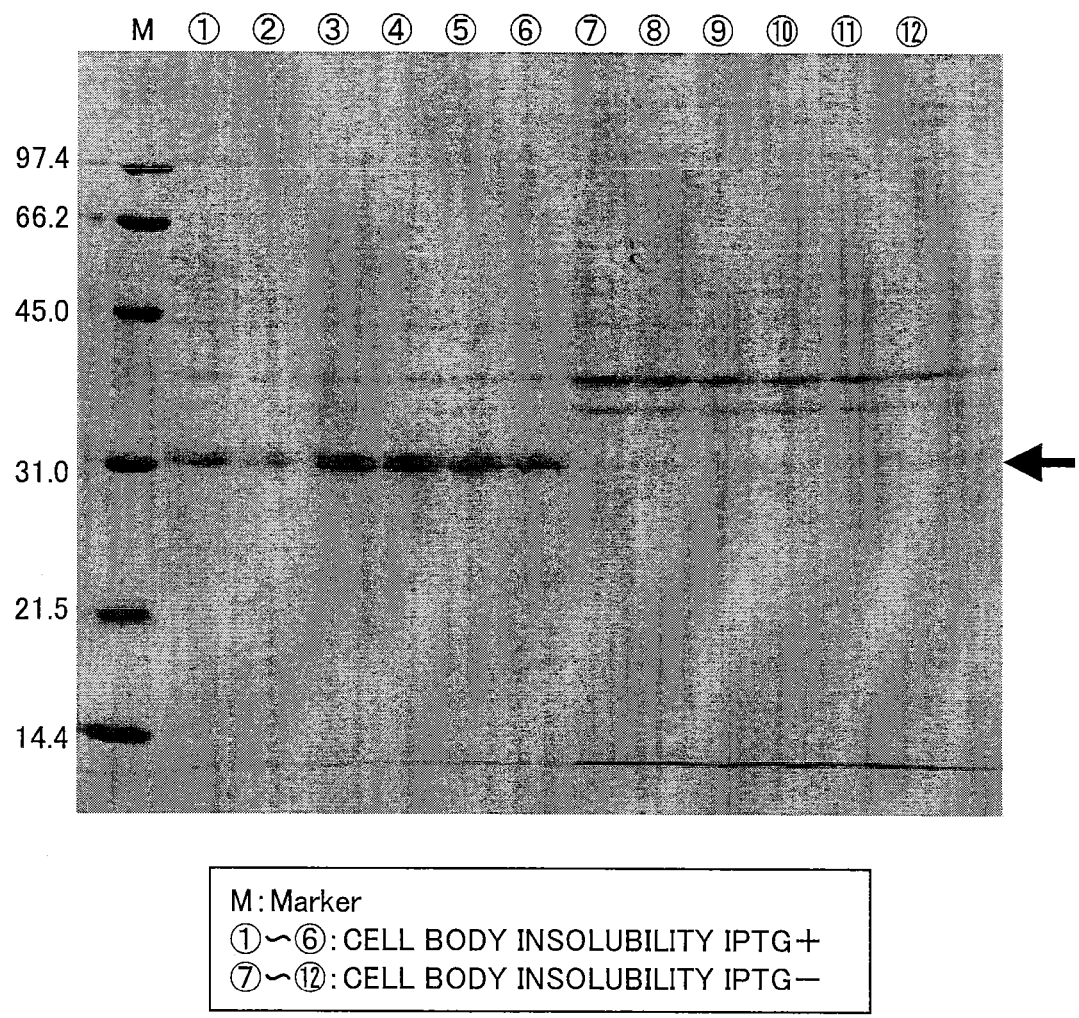
FIG. 10 shows expressed protein in an insoluble fraction of a bacterial cell in the transformed E. coli.

The soluble fraction and insoluble fractions of the suspension with (+) or without (−) of the IPTG induction were subjected to SDS-PAGE and coomassie staining, in order to confirm expression of the designed protein. Results thereof are shown in FIGS. 9 and 10. FIG. 9 is a view illustrating the result of the SDS-PAGE analysis of the protein in the microorganism soluble fraction. As illustrated in FIG. 9, the designed protein (the band of about 31 kDa indicated by the arrow) was detected slightly in the lane 2 with the IPTG induction (+). FIG. 10 is a view illustrating the result of the SDS-PAGE analysis of the protein in the microorganism insoluble fraction. As illustrated in FIG. 10, the designed protein was detected slightly in the lanes 1 to 6 with the IPTG induction (+).

(1-13. Identification of Expression Protein by Western Blotting)

Figure 11:
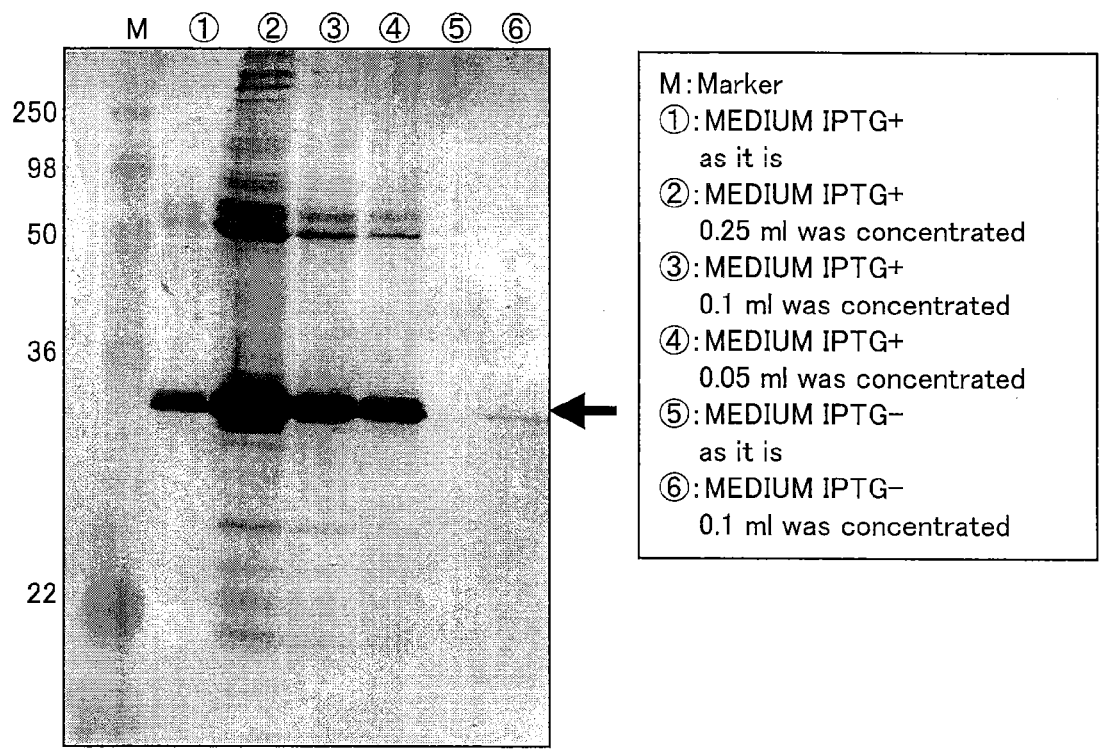
FIG. 11 shows expressed protein in the transformed E. coli, the expressed protein being identified by western blotting.

Because the expression of the protein was confirmed, western blotting with anti human (Fab')$_2$ antibody was then carried out in order to identify whether the expressed protein was the antibody light chain or not. Firstly, the media obtained in 2-4. with (+) or without (−) the IPTG induction were concentrated by trichloro acetic acid (TCA) precipitation and introduced in respective lanes of an electrophoresis gel. SDS-PAGE was performed with the gel. Then, by using an electrode, the electrophoresed was transferred to a membrane. The membrane was then subjected to blocking, and subjected to immunization reaction with the anti human (Fab')$_2$ antibody. After that, a coloring material liquid was added thereto. Then, the membrane observed. Result of the observation is shown in FIG. 11, which is a photograph showing the membrane in which the band of the desired protein was visualized. As shown in FIG. 11, a strong band was detected around 31 kDa at which a band was confirmed in FIGS. 7, 9, and 10. This identified that the protein expressed in *E. coli* was a human antibody light chain.

(1-14. Purification of Expressed Protein)

The expressed protein (human antibody light chain) was subjected to primary purification and secondary purification.

Figure 12:
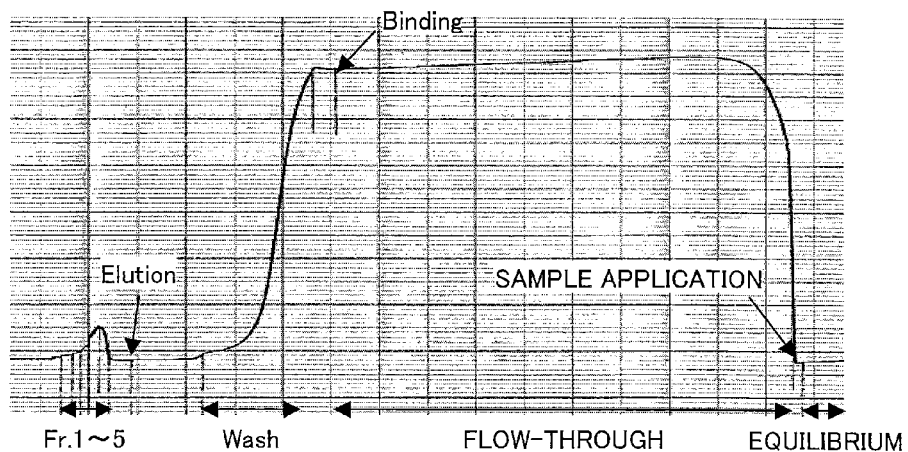
FIG. 12 shows a chromatogram at a time of a primary purification of target protein expressed in E. coli.
Figure 13:
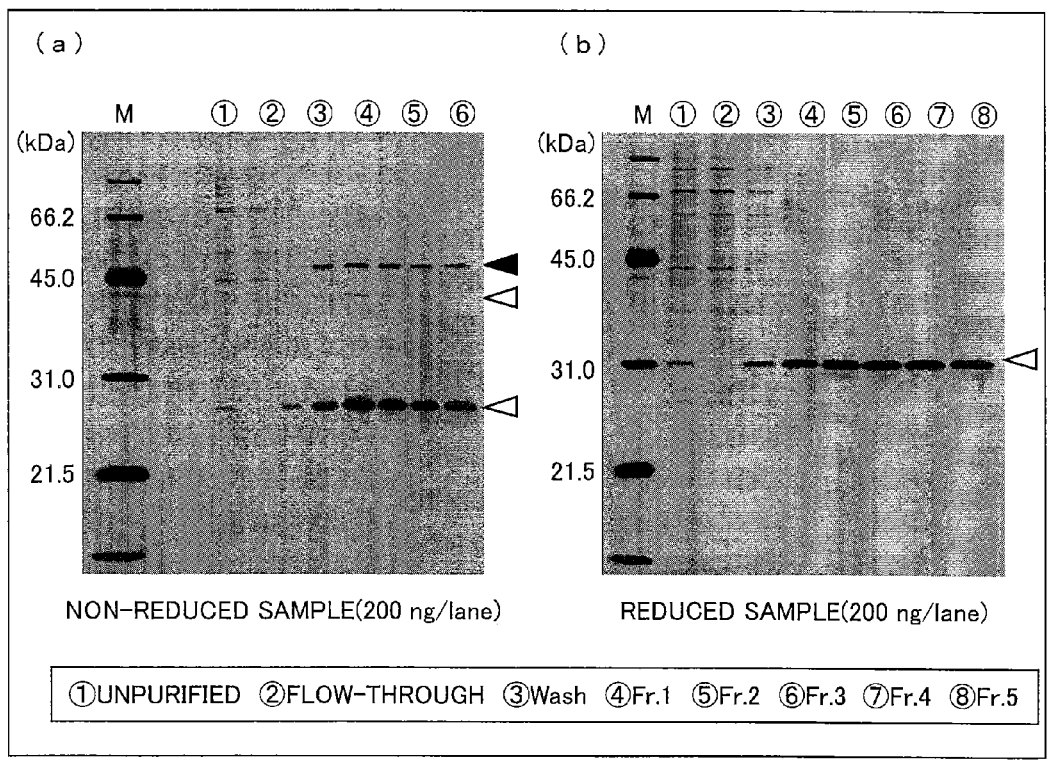
FIG. 13 shows a purification state after the primary purification of the target protein.

For the primary purification, affinity purification using an antibody column was performed. Chromatogram in the affinity purification is shown in FIG. 12. Each fraction thus obtained was analyzed by SDS-PAGE (stained with silver). Results thereof are shown in FIG. 13. (a) of FIG. 13 shows a result of the analysis of non-reduced sample of the expressed protein. (b) of FIG. 13 shows a result of non-reduced sample of the analysis of expressed protein. As illustrated in FIG. 13, the proteins were very successfully purified after fraction 2 (Fr. 2). The monomeric desired human antibody light chain was detected around about 26 kDa in the case of the non-reduced sample ((a) of FIG. 13), and around about 31 kDa in the case of the reduced sample ((b) of FIG. 13). Further, a dimer was detected around 50 kDa in the case of the non-reduced sample ((a) of FIG. 13). Note that the faint band around about 40 kDa is impurity. Fractions 1 to 3 (Fr. 1, Fr. 2, and Fr. 3) were collected together and subjected to secondary purification.

Figure 14:
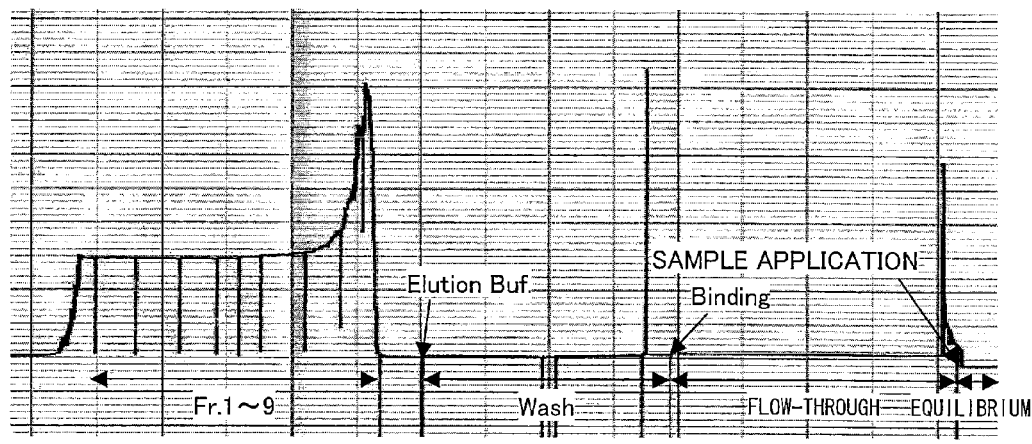
FIG. 14 shows a chromatogram at a time of a secondary purification of the target protein expressed in E. coli.
Figure 15:
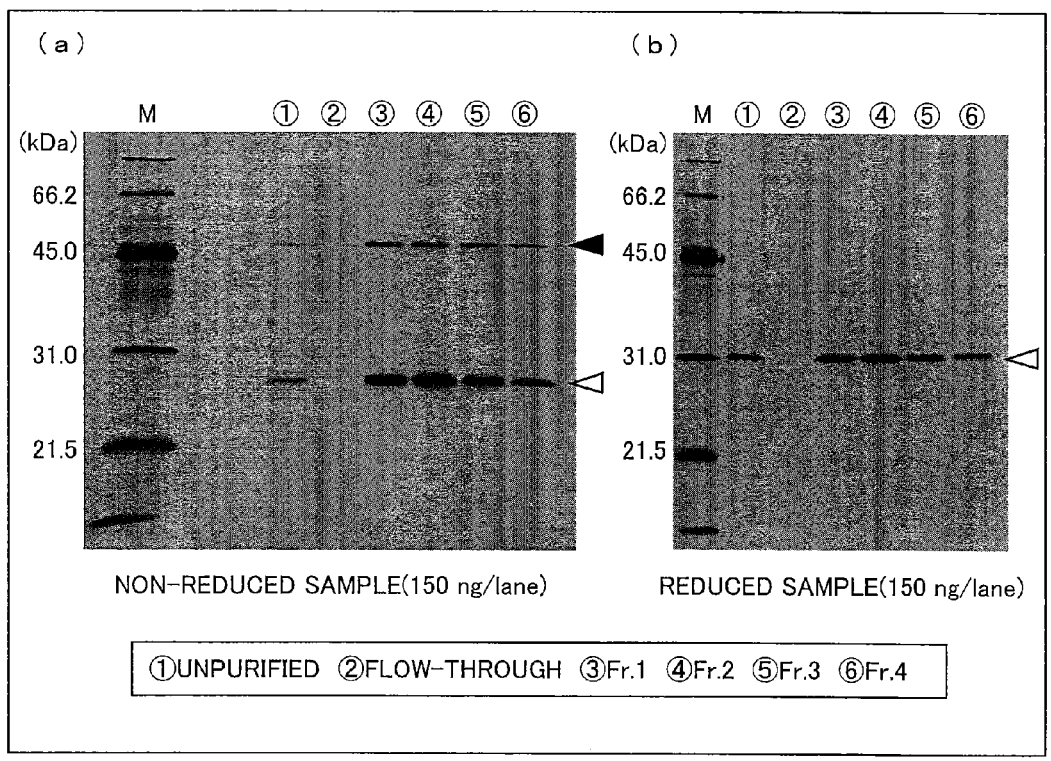
FIG. 15 shows a purification state after the secondary purification of the target protein.

For the secondary purification, His-tagged purification was performed. Chromatogram obtained in the His-tagged purification is shown in FIG. 14. Each fraction thus obtained was analyzed by SDS-PAGE (stained with silver). Results thereof are shown in FIG. 15. (a) of FIG. 15 shows a result of the analysis of non-reduced sample of the expressed protein. (b) of FIG. 15 shows a result of non-reduced sample of the analysis of expressed protein. As illustrated in FIG. 15, the proteins were successfully purified for all fractions. The monomeric desired human antibody light chain was detected around about 26 kDa in the case of the non-reduced sample ((a) of FIG. 15), and around about 31 kDa in the case of the reduced sample ((b) of FIG. 15). Further, a dimer was detected around 50 kDa in the case of the non-reduced sample ((a) of FIG. 15). As a result of the silver-staining, highly purely purified band was detected. This explains that the secondary purification further purified the expressed protein to such a high purity. Thus, the following enzymic activity test was carried out with a sample having been subjected to secondary purification.

(1-15. Enzymic Activity Test)

An enzymic activity of each of the human antibody light chains derived from the clones #1, #7, #11, and #16 thus purified in 1-14 was measured. The enzymic activity was measured by using a substrate (MCA-labeled peptide) in which MCA (methyl-Coumaryl-Amide) was bonded to commercially-available peptides having different sequences. In a protease activity test using the MCA-labeled peptide, protease activity is detected by utilizing phenomenon that a portion from which the labeled peptide is cleaved and liberated emits fluorescent light of a wavelength different from that of fluorescent light that the portion has emitted before the cleavage. In more details, the MCA-labeled peptide ε-amino group of lysine residue adjacent to the MCA, which is fluorescent material, is acetylated. When the MCA-labeled peptide is cleaved on C-terminal side of the lysine residue, the MCA-labeled peptide is divided into a peptide portion and AMC (Amino-Methyl-Coumarin). AMC is derived from MCA before the cleavage. The liberated AMC emits fluorescent light different from that of the peptidyl-MCA in wavelength. Thus, it is possible to measure the degree of the cleavage of the substrate by using a change in the intensity of the fluorescent light emitted from AMC.

(1-16. Material and Tool)

Samples tested herein were human antibody light chains produced and purified from the clones #1, #7, #11, and #16 in 1-14. As a negative control, an expression product from pET 20b (+) to which no human antibody light chain gene was inserted. For preparation of reagents etc., sterilized mili Q water was used. Microtubes and chips were autoclaved for sterilization before use. All septic operations were carried out in clean bench. Excitation wavelength for the measurement was 360 nm and fluorescent light wavelength to be measured is 465 nm.

(1-17. MCA Decomposition Test)

Reaction liquids were prepared by adding respective concentrated samples (10 μM, 5 μM, 1 μM) of each human antibody light chain thus purified to each MCA-labeled peptide, and reacted in a vapor-phase incubator at 25° C. and in a vapor-phase incubator at 37° C.

The MCA-labeled peptides used herein were: a mixture of VPR-MCA, QAR-MCA, D(OBzl)PR-MCA and Bz-R-MCA (R1 group as substrates of thrombin and trypsin); a mixture of IEGR-MCA and Pyr-GR-MCA (R2 group as Factor Xa and t-PA substrates); a mixture of EKK-MCA and VLK-MCA (K group as substrates of plasmin); a mixture of APA-MCA, AAF-MCA, and AAA-MCA (AF group as substrates of elastase and chymotrypsin); and Q(OBzl)AR-MCA, IEGR-MCA, PyrGR-MCA, VPR-MCA, QAR-MCA, EKK-MCA, EAR-MCA, R-MCA, DPR-MCA, PFR-MCA, and FSR-MCA. Note that the total concentration of each MCA peptide in the reaction liquid is 200 μM.

More specifically, a reaction liquid for the test was prepared by mixing the concentrated sample liquid (50 μl), 10 mM MCA-labeled peptide (mixture) (4 μl), and 50 mM Tris-HCl (pH 7.4) (146 μl) (to make up 200 μl in total), so that the human antibody light chain was reacted with the MCA substrate. A reaction liquid for negative control was prepared by mixing a solution of pET 20b (+) expression product (50 μl), 10 mM MCA-labeled peptide (mixture) (4 μl), and 50 mM Tris-HCl (pH 7.4) (146 μl) (to make up 200 μl in total), so that the pET 20b (+) expression product was reacted with the MCA substrate. A non-reacted reaction liquid was prepared by mixing 10 mM MCA-labeled peptide (mixture) (4 μl) and 50 mM Tris-HCl (pH 7.4) (194 μl) (to make up 200 μl in total). A reaction liquid for comparison was prepared by mixing 200 μM trypsin (100 μl), 10 mM MCA labeled peptide (mixture) (4 μl), and 50 mM Tris-HCl (pH 7.4) (96 μl) (to make up 200 μL in total), so that trypsin was reacted with the MCA substrate. In the tests for the human antibody light chain derived from the clones #1, #7, and #16, the reaction liquid was 2 μM in the human antibody light chain concentration, while trypsin concentration was 50 μM.

(1-18. Test Results)

Results of the MCA decomposition tests of the human antibody light chains derived from the clones #1, #7, #11, and #16 are shown in FIGS. 16 to 19.

Figure 16:
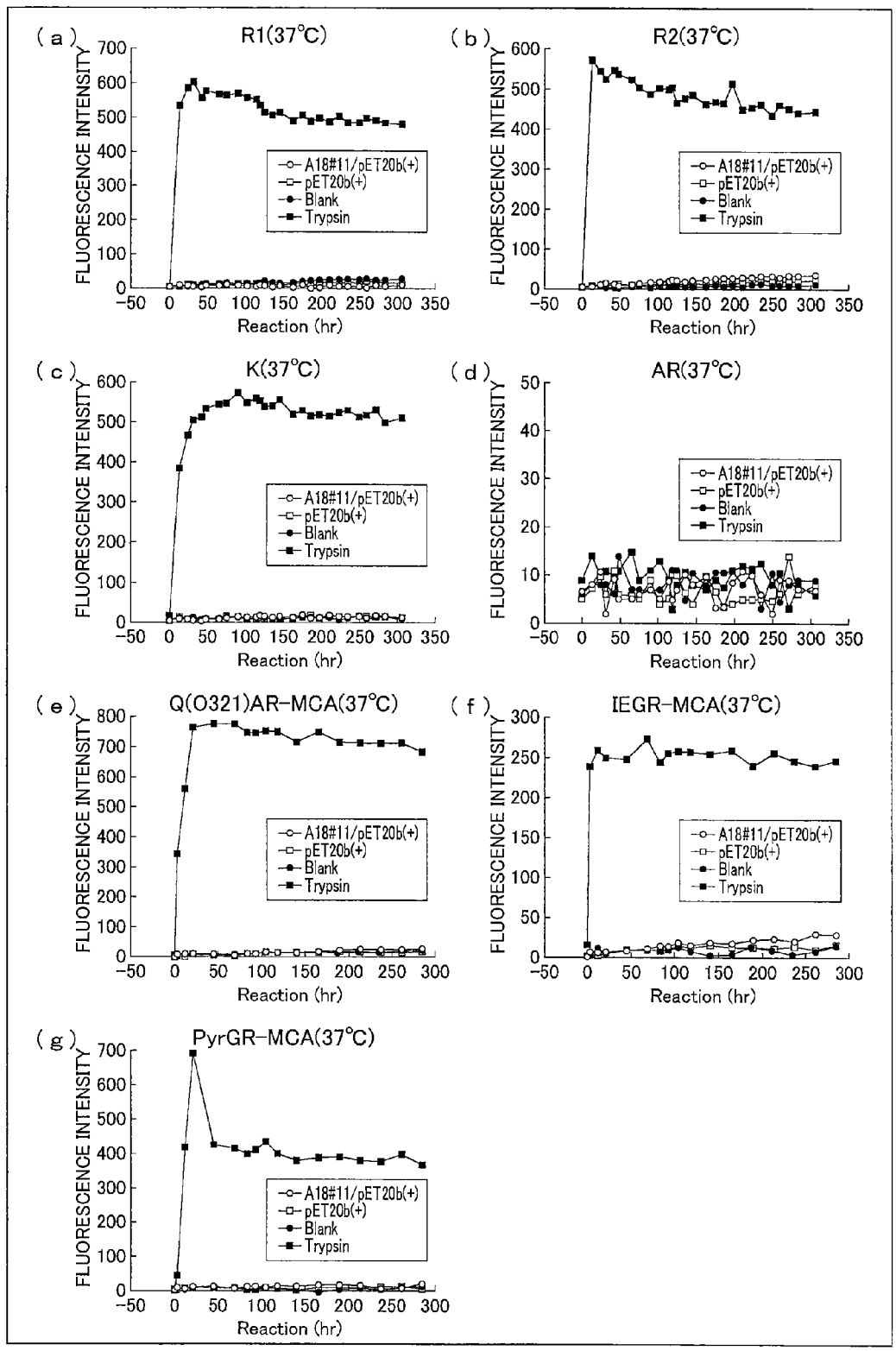
FIG. 16 shows enzyme activity of a polypeptide of clone #11 for various substrates

FIG. 16 is a view showing the result of the MCA decomposition test for human antibody light chain derived from the clone #11. pET 20b (+) indicates the negative control. A18#11/pET 20b (+) indicate the result of the human antibody light chain derived from the clone #11. Trypsin indicates the result of the test on trypsin. As shown in FIG. 16, the human antibody light chain of the clone #11 showed no or very subtle decomposition activity for each of R1, R2, K and AF groups in the 37° C. reaction (see (a) to (d) of FIG. 16). The result was same for the 27° C. reaction (no data is shown herein).

Further, the human antibody light chain of the clone #11 was tested on decomposition activities for D(OBzl)PR-MCA, IEGR-MCA, and Pyr-GR-MCA, individually. It was found that the human antibody light chain of the clone #11 had a subtle decomposition activity for IEGR-MCA (see (e) to (g) of FIG. 16).

Figure 17:
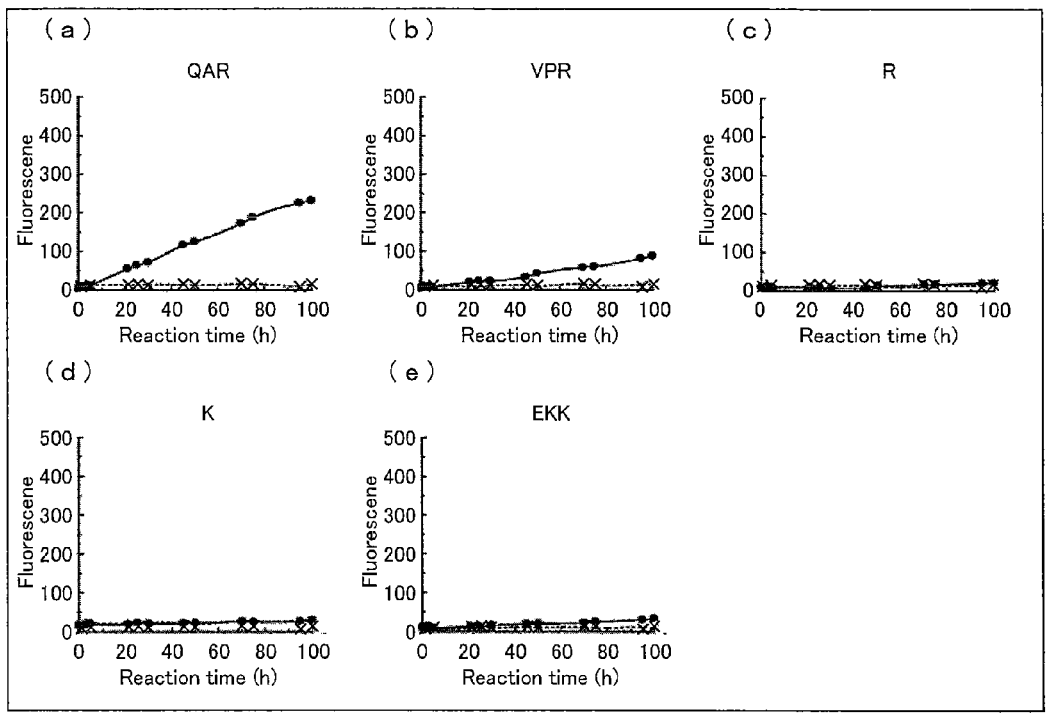
FIG. 17 shows enzyme activity of a polypeptide of clone #16 for various substrates.

FIG. 17 is a view illustrating the result of the MCA decomposition test of the human antibody light chain derived from the clone #16. "-x-" indicates the negative control, and "-•-" indicates the result of the test of the human antibody light chain derived from the clone #11. As shown in FIG. 17, the human antibody light chain of the clone #16 showed a decomposition activity for QAR-MCA and VPR-MCA (see (a) and (b) of FIG. 17). However, the human antibody light chain of the clone #16 showed almost no decomposition activity for the K group and EKK-MCA (see (c) and (d) of FIG. 17) and showed totally no decomposition activity for the AF group (see (e) of FIG. 17).

Figure 18:
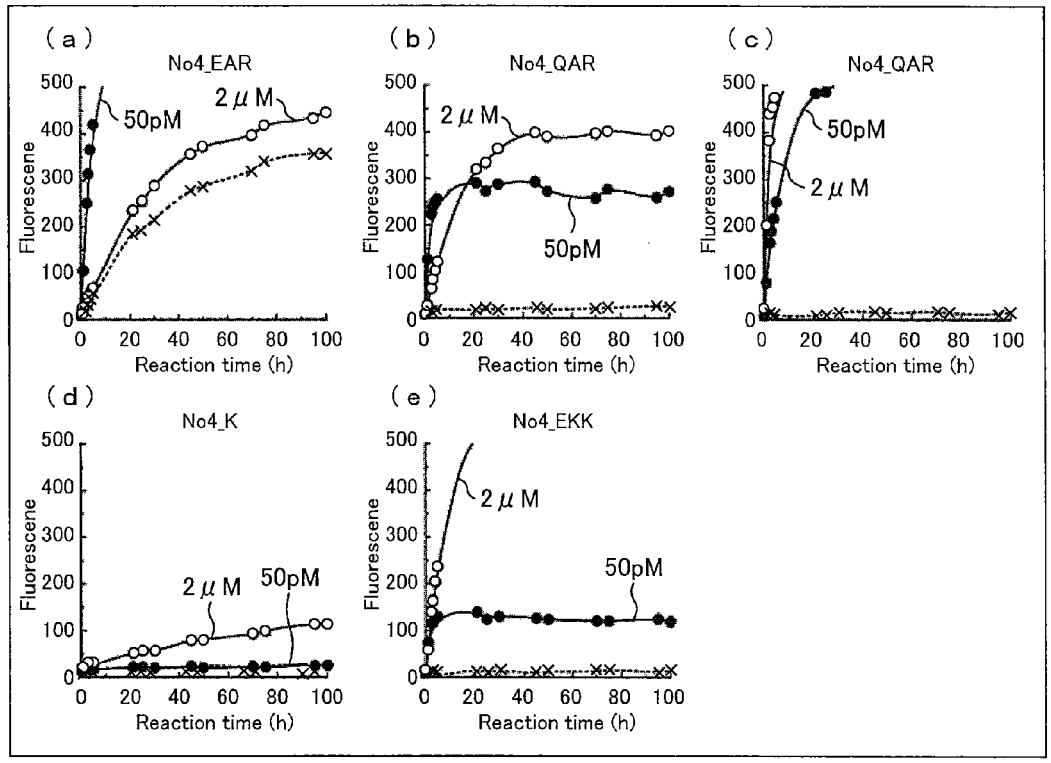
FIG. 18 shows enzyme activity of a polypeptide of clone #1 for various substrates.

FIG. 18 is a view illustrating the result of the MCA decomposition test of the human antibody light chain derived from the clone #1. "-x-" indicates the negative control, and "-•-" indicates the result of the test of the human antibody light chain derived from the clone #1. "-○-" indicates the result of the test of trypsin. As shown in FIG. 18, the human antibody light chain of the clone #1 showed a strong decomposition activity for EAR-MCA, QAR-MCA, and EKK-MCA (see (a) to (c), and (e) of FIG. 18). The human antibody light chain of the clone #1 showed a rather weak but steady decomposition activity for K (see (d) of FIG. 18). However, the human antibody light chain of the clone #1 showed totally no decomposition activity for the AF group (no data is shown here).

Figure 19:
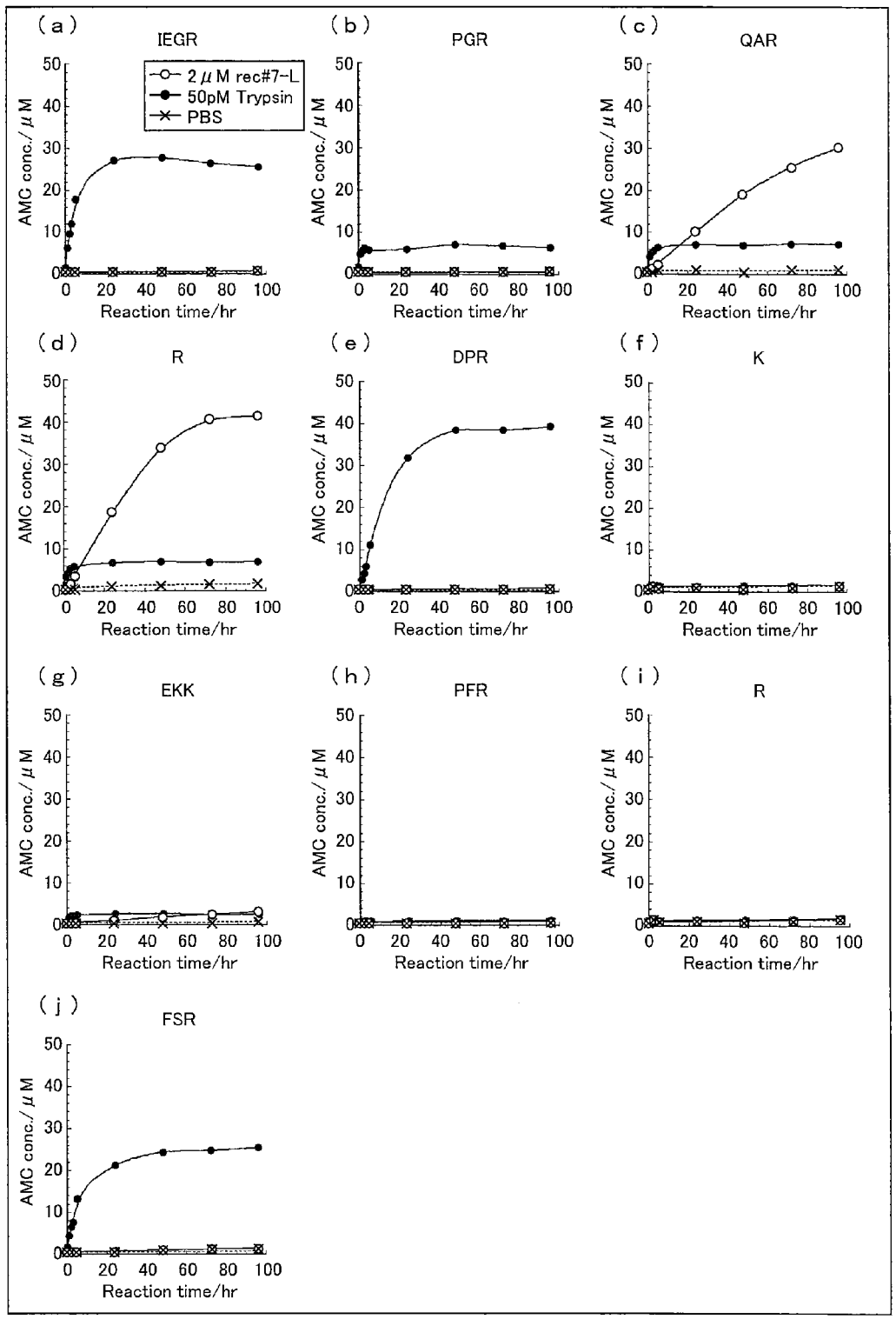
FIG. 19 shows enzyme activity of a polypeptide of clone #7 for various substrates

FIG. 19 is a view illustrating the result of the MCA decomposition test of the human antibody light chain derived from the clone #7. PBS indicates the negative control, and rec #7-L indicates the result of the test of the human antibody light chain derived from the clone #7. Trypsin indicates the result of the test of trypsin. As shown in FIG. 19, the human antibody light chain of the clone #7 showed a decomposition activity for QAR-MCA and Bz-R-MCA (see (c) and (d) of FIG. 19). The human antibody light chain of the clone #7 showed a slight decomposition activity for EKK-MCA (see (g) of FIG. 19). However, the human antibody light chain of the clone #1 showed totally no decomposition activity for the K group and the AF group ((f) of FIG. 19).

As described above, it was proved that human antibody light chains having decomposition activities for decomposing peptides were obtained. Especially, the human antibody light chain of the clone #1 has a strong activity and is therefore considered as being useful. Meanwhile, the human antibody light chain of the clone #1 was highly active but that of clone #11 was almost inactive, even though they are both from the same germline gene.

(1-19. Clones #6 and #18)

The clones #6 and #18 were also subjected to the genetic transformation, purification of expressed protein, and enzymic activity measurement, as in 1-9. to 1-18. As a result, it was found that the clone #6 had no enzymic activity but the clone #18 had an enzyme activity.

[2: Clone Preparation from LCA Library and LC2 Library]

Through the following procedure, two libraries, namely an LCA library and an LC2 libraries, were established.

(2-1. Preparation of Human Peripheral Blood cDNA)

Neutralization activities of blood serums from subjects hyperimmunized several times with vaccine of rabies virus was measured. Peripheral blood was collected from a subject whose blood serum showed the highest neutralization activity (7.2 IU). By using Ficoll-paque, lymph cells were isolated from the periphery blood. By using RNA extraction kit (Stratagene), total RNA was obtained from the isolated about 3.0× $10^7$ lymph cells. By using TheromoScript RT-PCR System (Invitrogen), reverse transcription of the total RNA was performed with oligo (dT) as a primer, so as to prepare a cDNA serving as a template in the later-described PCR reaction.

(2-2. LCA Library Establishment)

Figure 28:
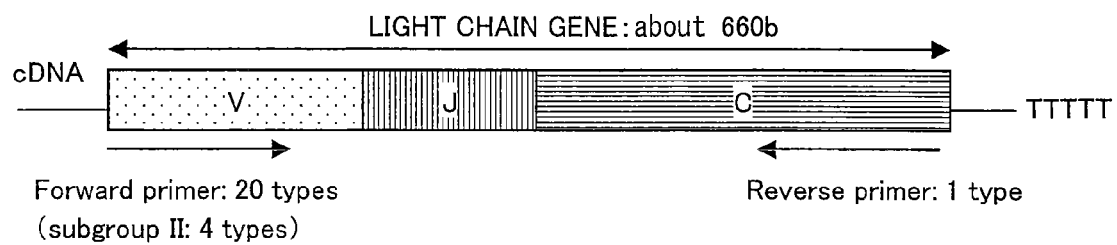
FIG. 28 is a schematic view of a schematic configuration of a primer set in accordance with an embodiment of the present invention.

A primer as illustrated in FIG. 28 was designed. More specifically, based on sequence information of human antibody light chain genes registered on IgBLAST of NCBI, a primer set for comprehensively amplifying these human antibody light chain genes was designed, which primer set includes 20 types of 5' (forward) primers and one type of 3'

(reverse) primer so as to make up 20 pairs. 5' primer used herein was an oligonucleotide having a nucleotide sequence corresponding to an N-terminal region of the V region of the human antibody light chain. 3' primer used herein was an oligonucleotide having a complementary sequence for a nucleotide sequence corresponding to the C-terminal region of the constant (C) region of the human antibody light chain. Note that the 5' primer was added with four nucleotides (CACC) for inserting into E. coli expression vector pET101/D-TOPO Vector® (Invitrogen).

Table 1 shows the nucleotide sequences of the primers. Table 1 also shows the subgroups of the V κ genes of the human antibody light chain genes to be applied by the 5' primers, respectively.

TABLE 4

| Primer No. | Sequence | Subgroup covered |
|---|---|---|
| Vk1aATOPO | CACCATGAACATCCAGATGACCCAG | I |
| Vk1aGTOPO | CACCATGGACATCCAGATGACCCAG | |
| Vk1bATOPO | CACCATGGACATCCAGTTGACCCAG | |
| Vk1bCTOPO | CACCATGGCCATCCAGTTGACCCAG | |
| Vk1cATOPO | CACCATGGCCATCCAGATGACCCAG | |
| Vk1cGTOPO | CACCATGGCCATCCGGATGACCCAG | |
| Vk1dTOPO | CACCATGGTCATCTGGATGACCCAG | |
| Vk1eTOPO | CACCATGGACATCCAGATGATCCAG | |
| Vk2aTOPO | CACCATGGATATTGTGATGACCCAG | II |
| Vk2bATOPO | CACCATGGATATTGTGATGACTCAG | |
| Vk2bGTOPO | CACCATGGATGTTGTGATGACTCAG | |
| Vk2cTOPO | CACCATGGAGATTGTGATGACCCAG | |
| Vk3aATOPO | CACCATGGAAATTGTGTTGACACAG | III |
| Vk3aGTOPO | CACCATGGAAATTGTGTTGACGCAG | |
| Vk3bTOPO | CACCATGGAAATAGTGATGACGCAG | |
| Vk3cTOPO | CACCATGGAAATTGTAATGACACAG | |
| Vk4a TOPO | CACCATGGACATCGTGATGACCCAG | IV |
| Vk5a TOPO | CACCATGGAAACGACACTCACGCAG | V |
| Vk6aTOPO | CACCATGGAAATTGTGCTGACTCAG | VI |
| Vk6bTOPO | CACCATGGATGTTGTGATGACACAG | |
| VCR2862* | ACACTCTCCCCTGTTGAAGCTCTTTGTG | — |

Next, PCR reaction with the cDNA was performed by using the 20 pairs of the primer sets, individually. In the PCR reaction, 5-min incubation at 95° C. was performed initially, and then 35 cycles of 95° C. for 15 sec, 54° C. for 50 sec, and 72° C. for 90 sec were repeated, after which the temperature was maintained at 72° C. for 10 minutes. PCR product was kept at 4° C. As a polymerase, AccuPrime Pfx DNA Polymerase (Invitrogen) was used according to manufacturer's instructions. The PCR product was subjected to agarose gel electrophoresis, after which the targeted band around 660 pb was cut out the gel and purified.

Figure 29:
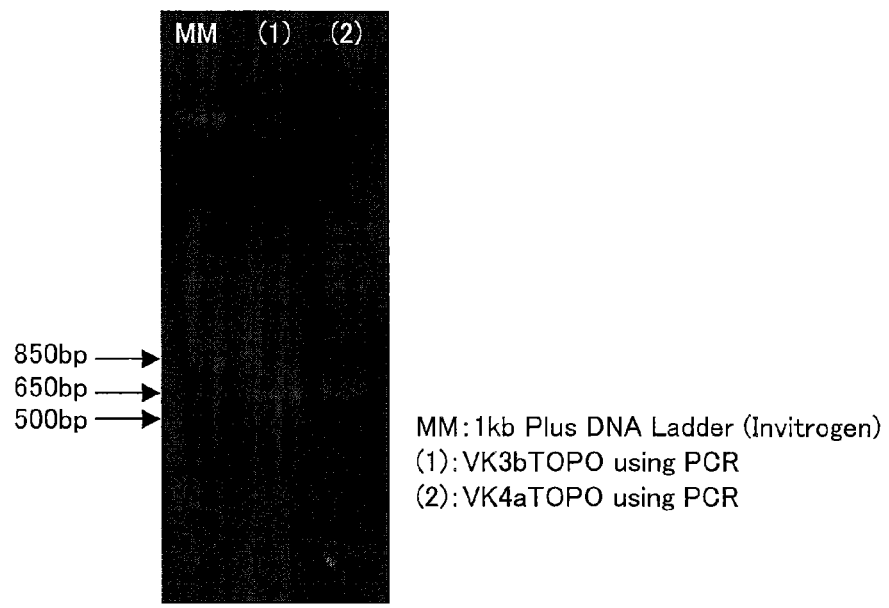
FIG. 29 shows a result of SDS-PAGE after PCR reaction in an embodiment of the present invention.

FIG. 29 shows part of the result of the electrophoresis of the PCR product. MM indicates a marker (1 kb Plus DNA LAdder, Invitrogen). (1) indicates the PCR reaction whose 5' primer was Vk3b TOPO. (2) indicates the PCR reaction whose 5' primer was Vk4a TOPO. As illustrated in FIG. 29, the main band was observed around 660 bp as intended, thereby proving that the human antibody light chain gene was efficiently amplified. Note that similar results were obtained for the PCR products from the PCR reaction using the other 5' primers.

Next, the purified PCR products were inserted into the E. coli expression vector pET101/D-TOPO® (Invitrogen) according to the manufacturer's instructions), respectively, so as to establish the LCA library, whose size was $1.35 \times 10^5$ CFU, thereby having a sufficient diversity.

(2-3. LC2 Library Establishment)

For amplifying only the human antibody light chain gene having the V κ gene belonging to the subgroup II, PCR reaction was performed in the same was as in 2-2., except that the 5' primers used herein were primers corresponding to the subgroup II (4 types of primers, namely, Vk2aTOPO, Vk2bATOPO, Vk2bGTOPO, Vk2cTOPO shown in Table 4), and the 3' primers used herein was VCR 2862.

Figure 30:
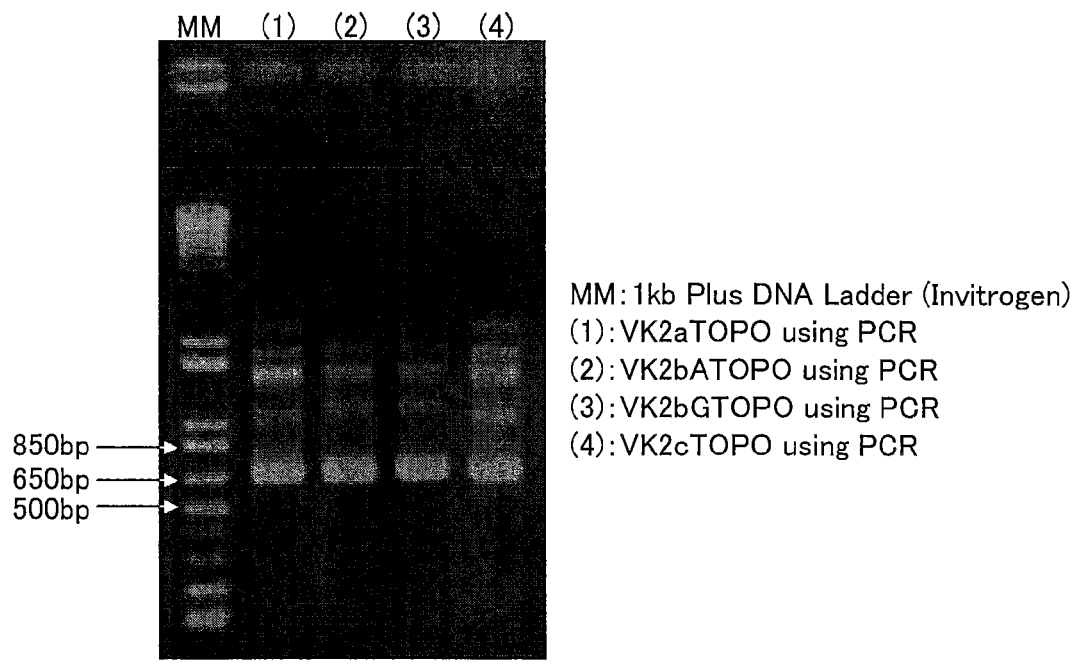
FIG. 30 shows a result of SDS-PAGE after PCR reaction in an embodiment of the present invention.

FIG. 30 shows part of the result of the electrophoresis of the PCR product. MM indicates a marker (1 kb Plus DNA Ladder, Invitrogen). (1) indicates the PCR reaction whose 5' primer was Vk2aTOPO. (2) indicates the PCR reaction whose 5' primer was Vk2bATOPO. (3) indicates the PCR reaction whose 5' primer was Vk2bGTOPO. (4) indicates the PCR reaction whose 5' primer was Vk2cTOPO. As illustrated in FIG. 30, the main band was observed around 660 bp as intended, thereby proving that the human antibody light chain gene was efficiently amplified.

Next, as in 2-2., the purified PCR products were inserted into the E. coli expression vector pET101/D-TOPO® (Invitrogen) according to the manufacturer's instructions), respectively, so as to establish the LC2 library, whose size was $2.58 \times 10^4$ CFU, thereby having a sufficient diversity.

The inventors of the present invention have demonstrated that the polypeptide encoded by the V gene of the κ light chain belonging to the subgroup II (V κ gene of the subgroup II) in human antibody has the triad residue-like structure highly frequently (see Patent Literature 1). Therefore, it may be highly possible that the human antibody light chains encoded by the clones included in the LC2 library has a catalytic triad residues-like structure amino acid residue, thereby having an enzyme activity.

(2-4. Genetic Transformation of E. coli)

The E. coli TOP10 was transformed for the two libraries (LCA library and LC2 library) thus established. After the plasmid was sufficiently amplified inside TOP10, its cell structure was crashed to collect the plasmid, which was then purified. The purified plasmid was used for transformation of E. coli BL21, which is a strain capable of expressing the antibody light chain efficiently. From transformer thus obtained, 384 clones were randomly selected for each of the libraries (i.e., 768 clones in total), and subjected to the following screening.

(2-5. First and Second Screening)

First screening was performed as below. More specifically, each E. coli clone was cultured with LB mediums of 150 µl, and its supernatant was measured by ELISA method in terms of expression of the antibody light chain, and a bonding activity for two types of rabies virus antibodies. Based on the measurement result, 20 clones from the LCA library and 23 clones from the LC library (43 clones in total) were selected as clones having the bonding activity for two types of rabies virus antibodies.

Further, the clones selected in the first screening were subjected to second screening, which was conducted in the same way as the first screening, except that culturing was carried out with the LB medium of 10 ml. In the second screening, the plasmid was collected from each E. coli clone, and clones having good collection efficiencies were selected.

Moreover, sequencing was performed for the plasmid thus obtained. Based on thus obtained sequences, a nucleotide sequence of N terminal of V κ region was determined, and subgroups of antibody light chain to which the clones of the sequences correspond, and germline genes of the clones were deduced. Further, based on the sequences, four (4) clones having a catalytic triad residues-like structure residue having serine, histidine, asparagines were selected from LC2 library (LC22F6, LC22G2, LC23D4, LC23F1).

The results thereof are shown in Table 5. Based on the results, the four (4) clones were selected from the LC2 library, and three (3) from the LCA library (LCA1B8, LCA2C2, and LCA2H9). These clones thus selected was subjected to third screening.

TABLE 5

| Clone No. | | 150 μl culture supernatant | | | 10 ml culture cell breakage liquid | | | PR | CTAAR |
|---|---|---|---|---|---|---|---|---|---|
| | | LCE | AS 1 | AS 2 | LCE | AS 1 | AS 2 | | |
| LCA Library | LCA1A5 | 1.865 | 0.276 | 0.365 | 2.021 | 0.282 | 0.686 | o | x |
| | LCA1B8* | 2.838 | 0.251 | 0.349 | 2.741 | 0.436 | 1.879 | o | x |
| | LCA1E2 | 1.221 | 0.286 | 0.203 | 1.831 | 0.216 | 0.428 | o | x |
| | LCA2C2* | 2.876 | 0.307 | 0.487 | 2.760 | 0.743 | 2.284 | o | x |
| | LCA2G1 | 2.974 | 0.360 | 0.263 | 2.190 | 0.342 | 1.001 | o | x |
| | LCA2H2 | 3.029 | 0.223 | 0.246 | 1.785 | 0.362 | 0.947 | o | x |
| | LCA2H7 | 0.579 | 3.038 | 0.227 | 2.351 | 0.500 | 1.593 | o | x |
| | LCA2H9* | 3.032 | 0.227 | 0.497 | 2.294 | 0.341 | 0.878 | o | x |
| | LCA4A2 | 2.934 | 0.369 | 0.365 | 1.408 | 0.145 | 0.183 | x | x |
| | LCA4A3 | 2.967 | 0.481 | 0.238 | 0.914 | 0.165 | 0.202 | x | x |
| LC2 Library | LC22F6 | 2.600 | 0.275 | 0.175 | 2.958 | 0.500 | 2.765 | o | o |
| | LC22G2 | 3.000 | 0.283 | 0.181 | 2.787 | 0.227 | 0.668 | o | o |
| | LC22H1 | 1.143 | 0.299 | 0.182 | 2.736 | 0.349 | 1.148 | o | x |
| | LC23B5 | 1.284 | 0.287 | 0.171 | 2.651 | 0.512 | 1.397 | o | x |
| | LC23B6 | 2.925 | 0.279 | 0.18 | 1.053 | 0.136 | 0.165 | x | x |
| | LC23D1 | 2.792 | 0.258 | 0.249 | 2.949 | 2.594 | 2.863 | o | x |
| | LC23D4 | 2.815 | 0.277 | 0.171 | 2.941 | 0.330 | 1.053 | o | o |
| | LC23F1 | 1.528 | 0.249 | 0.219 | 3.029 | 0.821 | 2.946 | o | o |
| | LC24A5 | 2.914 | 0.259 | 0.238 | 2.909 | 0.378 | 1.302 | o | x |

LCE stands for Light Chain Expression.
AS stands for Antigen Specificity.
PR stands for Plasmid Recovery.
CTAAR stands for Catalytic Triad Amino Acid Residue.
o stands for Good.
x stands for Poor.

(2-6. Crude Purification)

Figure 31:
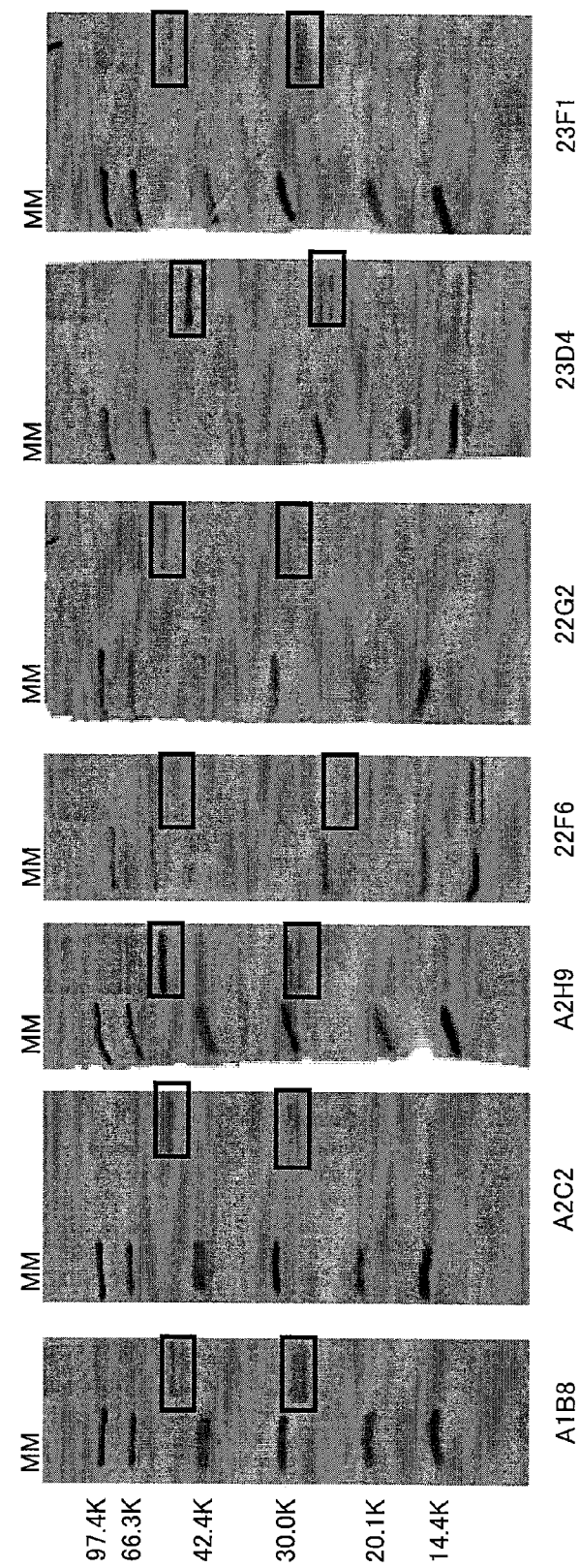
FIG. 31 shows a result of SDS-PAGE of each sample after a crude purification in an embodiment of the present invention.

The seven (7) clones were cultured in 100 ml cultures. Cell bodies in which the antibody light chains were expressed were crushed by freezing and thawing. The crushed was centrifuged to collect supernatant thereof. The supernatant thus collected was, as a sample containing the antibody light chain, subjected to crude purification using His tag derived for the expression vector, thereby roughly purifying the antibody light chain. The purification was carried out by naturally dropping a buffer solution into an open column filled with a carrier (Ni Sepharose™6 fast Flow). The buffer solutions used for column equilibrium, binding, and post-sample application washing had such a composition that 20 mM sodium phosphate, 0.5 M sodium chloride, and 20 mM imidazole (pH 7.4) were used. A buffer solution for elution was 20 mM sodium phosphate, 0.5 M sodium chloride, and 500 mM imidazole (pH 7.4) were used. After the elusion, the protein eluded fraction was dialyzed with PBS (−) overnight. The dialyzed was then concentrated by centrifugation with a ultra filter membrane (MILLIPORE) whose filtering capacity is a molecular weight of 10000, thereby obtaining a crude product. The crude product was subjected to confirmation using the SDS electrophoresis and coomassie brilliant blue staining (see FIG. 31). In FIG. 31, the bands indicated by the rectangular frames are deduced that the one lower in molecular weight indicates the monomeric antibody light chain, the one higher in molecular weight indicates a dimer of the antibody light chain. The monomeric antibody light chain had a molecular weight of about 27 kDa, because the tag and etc. were added thereto.

(2-7. Third Screening)

Among the crude products thus obtained, some that had not precipitated in the purification were measured as to affinities (kd) for rabies virus antibody (rabies virus sample (αCVS) and purified chick embryo cell rabies vaccine (αPECE)), which were immobilized on an ELISA plate.

Moreover, for 22D4 and 22F6, enzyme activity test was conducted. The antibody light chain purification was carried out wholly under a low temperature (4° C.) in the presence of 1 mM dithiothreitol (DTT). Supernatant of a culture of the antibody light chain-expressed cell was concentrated, and then diluted with a triple amount of a mobile phase (PBS+ 20% glycerol+1 mM DTT), thereby preparing a sample. The sample was subjected to affinity purification and gel filtration based on a well-known methods. Purity of the sample thus purified was confirmed by western blotting and silver staining.

As substrates (MCA-labeled peptides) used in the measurement of enzyme activities, Bz-Arg-MCA, Boc-Glu-Lys-Lys-MCA, Glu-Ala-Ala-MCA, and Suc-Ala-Ala-Ala-MCA (Peptide Institute Inc.; adjusted to 10 mM with DMSO) were used. As a buffer, a buffer 2 composed of 50 mM Tris-HCl (pH 7.7), 100 mM glycine, 0.025% Tween 20 and 0.02% NaN$_3$.

Figure 32:
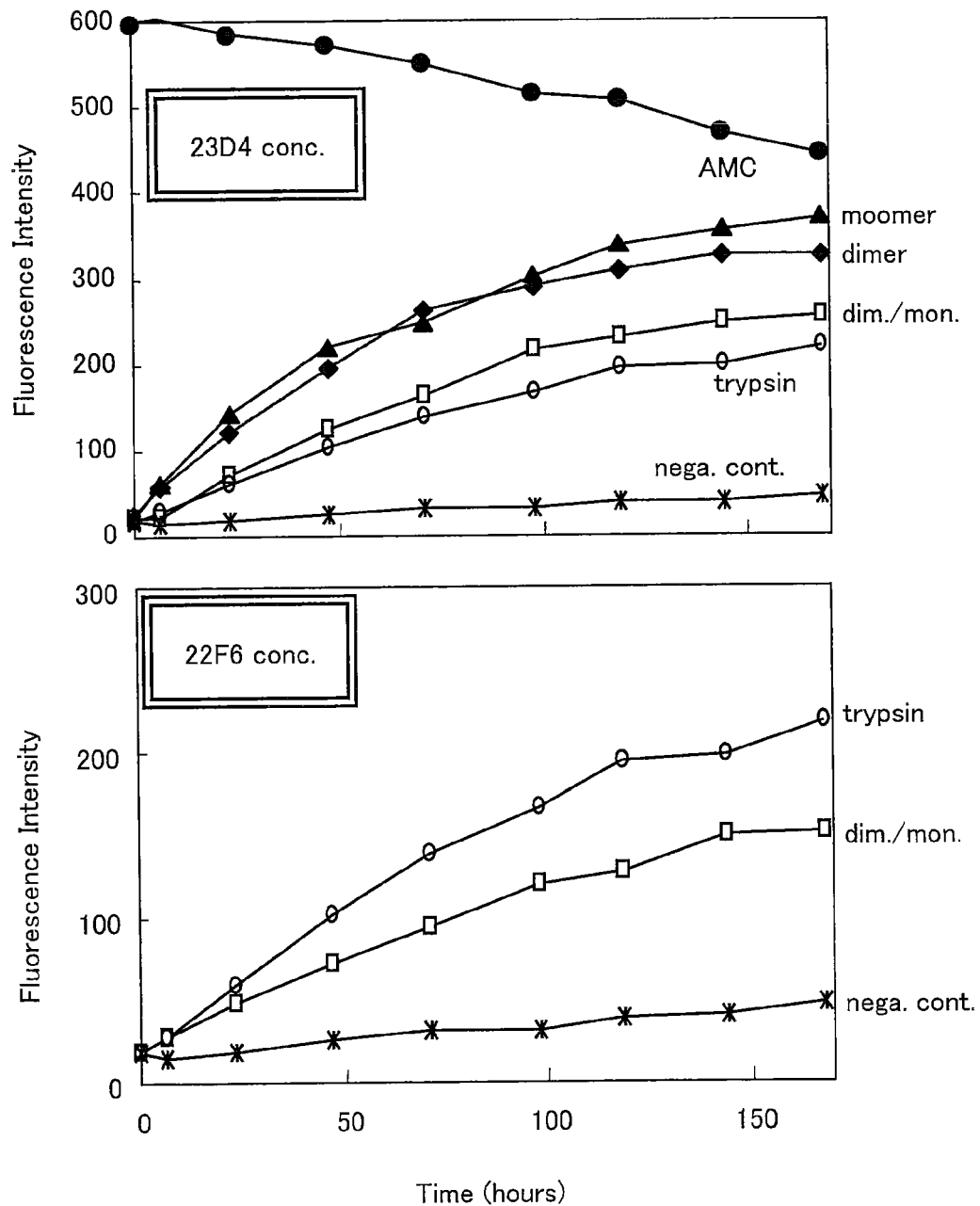
FIG. 32 shows enzyme activity of clone 23D4 and clone 22F6.

A reaction liquid of 1500 μl was prepared by mixing 60 μl of each substrate and 1260 μl of the buffer 2. Each sample of 100 μl was mixed with 100 μl of the reaction liquid and incubated at 37° C., while measuring fluorescent light periodically. Results of the measurements are shown in FIG. 32. As a negative control, a buffer 1 was used, which contained 50 mM Tris-HCl (pH 7.7), 100 mM glycine and 0.02% NaN$_3$. As a positive control, a mixture of 1 mg/ml (42 μM) trypsin (1.6 mg) and 1 mM HCl (1.6 ml), which mixture was diluted to 40 μM with the buffer 1, was used. Furthermore, a sample prepared by diluting 10 mM AMC to 400 mM with the buffer 1 was added to the reaction liquid and measured for fluorescent light. As can be seen from FIG. 32, both of 22D4 and 22F6 had enzyme activities. Moreover, 23F1 was measured for the enzyme activities in the same way.

The results are collectively shown in Table 6. Based on the results, L22F6, LC23D4, and LC23F1 were taken as candidates for abzymes having the anti virus activities. Note that the molecular weights of L22F6 and LC23D4 are shown together in Table 6.

TABLE 6

| Library | Clone No. | Vκ Subgroup | Precipitation | Yield | Kd | EA | MW |
|---------|-----------|-------------|---------------|-------|-----|-----|-----|
| LCA Library | LCA1B8 | 1 | yes | — | — | — | — |
| | LCA2C2 | 1 | yes | — | — | — | — |
| | LCA2H9 | 3 | no | low | $1.51 \times 10^{-7}$ | x | — |
| LC2 Library | LC22F6 | 2 | no | high | $1.10 \times 10^{-7}$ | ○ | 24,025 |
| | LC23D4 | 2 | no | low | $8.46 \times 10^{-8}$ | ○ | 24,098 |
| | LC23F1 | 2 | no | medium | $6.92 \times 10^{-8}$ | □ | — |
| | LC24A5 | 1 | yes | — | — | — | — |

EA stands for Enzyme Activity.
MW stands for Molecular Wight.

For the three (3) clones, namely, L22F6, LC23D4, LC23F1, theirs whole nucleotide sequences were determined. Base on the nucleotide sequences thus determined, amino acid sequences, and variable domain s and constant domains of light chains were deduced by using analysis software (GENETIX Ver. 8). LC23D4 had a V κ site (V κ gene in the germline gene) having 100% homology with the germline gene A19/A3. LC22F6 had a V κ site (V κ gene in the germline gene) having 97.7% homology with the germline gene A19/A3.

The whole nucleotide sequence of the clone LC23D4 is shown in SEQ ID NO: 29, and is deduced to encode the amino acid sequence shown in SEQ ID NO: 28. In the amino acid sequence shown in SEQ ID NO: 28, the 1st to 112th amino acids are the variable domain, and the 24th to 39th amino acids are CDR1, the 55th to 60th CDR2 are CDR2, and the 94th to 102th are CDR 3. The amino acid sequence of only the variable range is shown in SEQ ID NO: 30.

The whole nucleotide sequence of the clone L22F6 is shown in SEQ ID NO: 34, and is deduced to encode the amino acid sequence shown in SEQ ID NO: 33. In the amino acid sequence shown in SEQ ID NO: 33, the 1st to 112th amino acids are the variable domain, and the 24th to 39th amino acids are CDR1, the 55th to 60th CDR2 are CDR2, and the 94th to 102th are CDR 3. The amino acid sequence of only the variable range is shown in SEQ ID NO: 35.

The whole nucleotide sequence of the clone LC23F1 is shown in SEQ ID NO: 39, and is deduced to encode the amino acid sequence shown in SEQ ID NO: 38. In the amino acid sequence shown in SEQ ID NO: 38, the 1st to 112th amino acids are the variable domain, and the 24th to 39th amino acids are CDR1, the 55th to 60th CDR2 are CDR2, and the 94th to 102th are CDR 3. The amino acid sequence of only the variable range is shown in SEQ ID NO: 40.

[3: Evaluation of Anti Virus Activity]

(3-1. Purification of Human Antibody Light Chain Derived from Clone #1)

Figure 20:
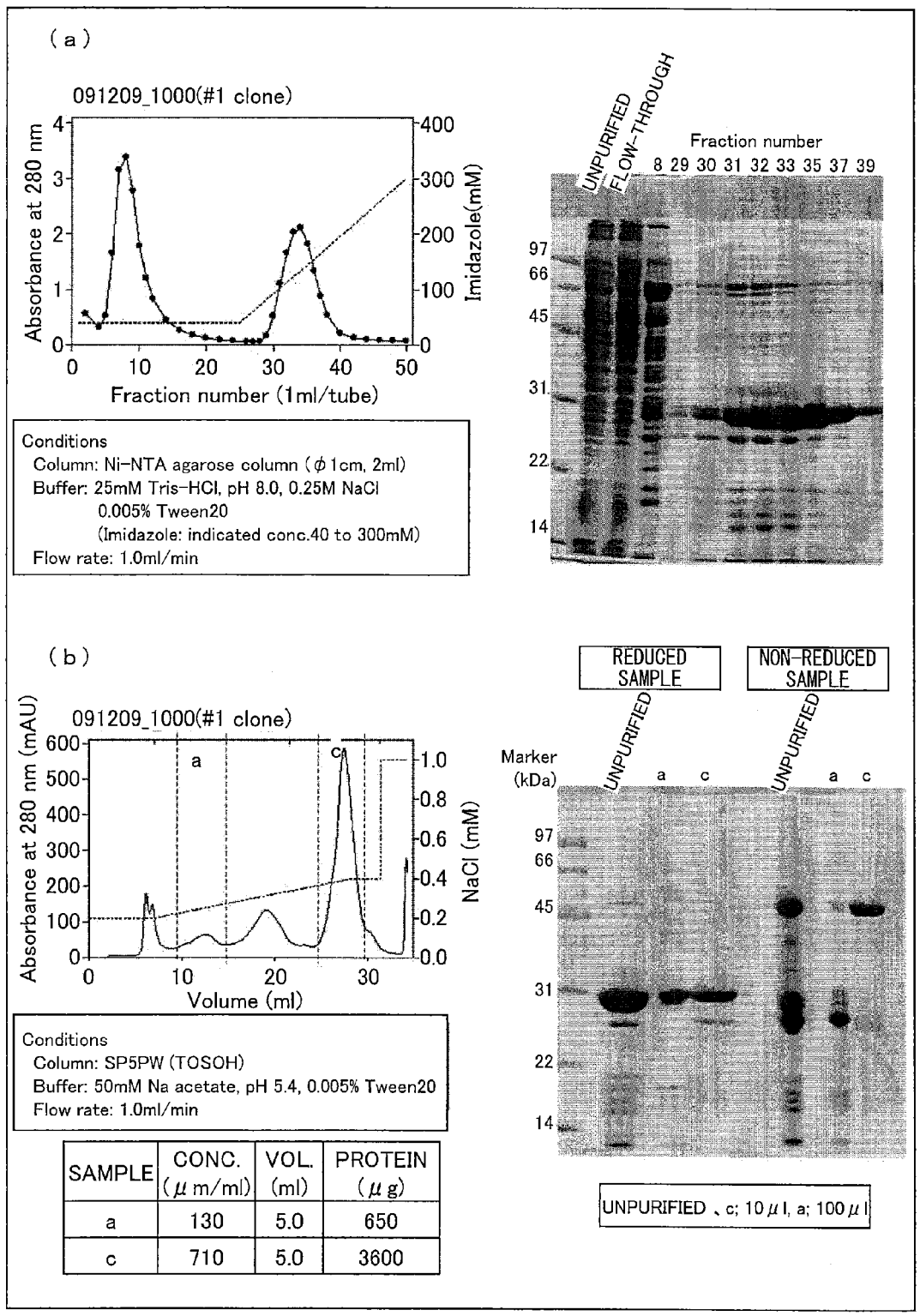
FIG. 20 shows results of purifications of a polypeptide of clone #1.

The human antibody light chain derived from the clone #1 for evaluation was subjected to the primary purification and the secondary purification as described below. (a) of FIG. 20 is a view illustrating results of Ni-NTA column chromatogram of the primary purification and SDS-PAGE analysis thereof. (b) of FIG. 20 is a view illustrating results of positive ion exchange column chromatogram of the primary purification and SDS-PAGE analysis thereof.

As shown in left-hand side in (a) of FIG. 20, a buffer A (25 mM Tris-HCl (pH 8.0), 0.25M NaCl, and 40 mM imidazole, 0.005% Tween 20) was flown until flow-through was completely flowed past after sample application. Components bonded with the gel was eluted while the concentration of imidazole was increased gradually from 40 mM to 300 mM as indicated by the broken line in the left graph. The column used herein was Ni-NTA agarose column (diameter 1 cm, 2 ml). Throughout the purification, a flow rate was maintained at 0.1 mL/min. As shown in the right hand side of (a) of FIG. 20, the desired band at about 31 kDa was detected in the fractions 30 to 37. The fractions were collected together and subjected to the secondary purification.

As shown in left-hand side in (b) of FIG. 20, a buffer A (50 mM of sodium acetate (pH 5.4), 0.2 M NaCl, 0.005% Tween 20) was flown until flow-through was completely flowed past after sample application. Components bonded with the gel was eluted while the concentration of NaCl was increased gradually from 0.2 M to 0.4 M as indicated by the broken line in the left graph. The column used herein was SP5PW (HOSHO). Throughout the purification, a flow rate was maintained at 0.1 mL/min. The sample before the purification, components belonging to the region "a" enclosed with the broken lines in the graph (fractions 10 to 15) and to the region "c" enclosed with the broken lines in the graph (fractions 25 to 30) were analyzed with SDS-PAGE. As shown in the right hand side of (b) of FIG. 20, the desired band at about 31 kDa was detected in a and c in the reduced sample. For the non-reduced sample, the band at about 31 kDa was detected only in a and the band at about 51 kDa was detected only in c. As described above, the monomeric antibody light chain is about 31 kDa, and the dimer thereof is about 51 kDa. Thus, it can be concluded that the sample a is the fraction of the monomeric antibody light chain and the sample c is the fraction of the dimer of the antibody light chain.

(3-2. Evaluation to Find Suitable Reaction Temperature, Reaction Time, and Concentration for Anti Virus Activity)

Next, virus neutralization test was conducted by using the human abzyme and virus, so as to analyze the anti virus activity of the human antibody light chain. The viruses used in the test were CVS-11 strain (hereinafter, referred to as CVS), ERA strain (hereinafter, referred to a ERA), and HEP-Flury strain (hereinafter, referred to as HEP) of rabies virus (hereinafter, referred to as RABV), and vesicular stomatitis virus (hereinafter, VSV), and reovirus (hereinafter, referred to as ReoV). As cells to be infected with the viruses, NA cells were used for RABV, and L929 cells for the other viruses.

In each well of 6-well plate, an appropriate number of NA cells were inoculated and incubated at 37° C. overnight, thereby adhering a monolayer of the cells to the well. RABV (CVS) having an infectivity titer of 100 to 200 PFU (plaque formation unit), and the human abzyme (final concentration 0.5 mg/mL) or PBS were mixed together, and incubated for 24 hours or 48 hours for three different temperatures 15° C., 25° C., and 30° C. for each sample, thereby obtaining virus liquids including virus liquids in which the virus was reacted with the human abzyme and a virus liquid in which PBS was added with the virus. The virus liquids were introduced into the respective wells after the medium inside the wells were discarded. The virus liquids in the well were incubated at 37° C., thereby causing the virus to adhere to the cells. After the adhesion, the virus liquid was discarded and a medium was appropriately added therein. Then, the plate was incubated at 37° C. until plaque was formed sufficiently (for 1 to 2 days). After the incubation, the medium was discarded and then the cells were immobilized.

(3-3. Plaque Assay for Measuring the Infected Focus)

The immobilized cells were washed and stained with crystal violet introduced in the wells. The crystal violet was discarded after the cell staining. Then, the wells were washed with water. Each well was then observed visually or stereomicroscopically. Non-stained portions due to cells infected with the virus and thereby eliminated from the wells were counted as plaque. Percentage of the number of plaques formed in the well treated with the mixture liquid of the human abzyme and the virus was calculated out, where the number of plaques formed in the well treated with the mixture liquid of the PBS and the virus was put as 100%. Results thereof are shown in FIG. 21. (a) of FIG. 21 is a view illustrating evaluation on temperatures at which the human abzyme expressed a high activity. (b) of FIG. 21 is a view illustrating evaluation on concentrations at which the human abzyme expressed a high activity.

As shown in (a) of FIG. 21, the human abzymes according to the present invention down-regulated most of the viruses in the incubations with the viruses at 25° C. for 48 hours. The human abzymes according to the present invention down-regulated most of the viruses in the incubations with CVS at 30° C. for 24 hours. As shown in (b) of FIG. 21, the human abzymes according to the present invention, which were incubated with various concentrations at 25° C., expressed equivalent or rather more excellent activities, compared with their virus regulation capacity at 30° C. Thus, it was decided that the incubation of the human abzyme and the virus in later experiments were to be conducted at 25° C. for 48 hours with human abzyme concentration of 1.5 mg/ml.

(Experiments of Anti Virus Activity Against Various Viruses)

The incubation of the human abzyme and the virus was carried out as described in 3-2. The virus inspection was carried out as described in 3-3. The human abzyme including only the monomer and the human abzyme including only dimer were individually examined in terms of their anti virus activity for the three trains of rabies virus, VSR, and ReoV. As in 3-3., plaque assay was used to find out the percentage of the plaque number formed in the wells treated with the mixture liquid of the human abzyme and the respective viruses, where the number of plaque formed in the well treated with the mixture liquid of PBS and the respective viruses was put as 100%. Results thereof are collectively plotted on the graph in FIG. 22.

Figures 22, 23, 24:
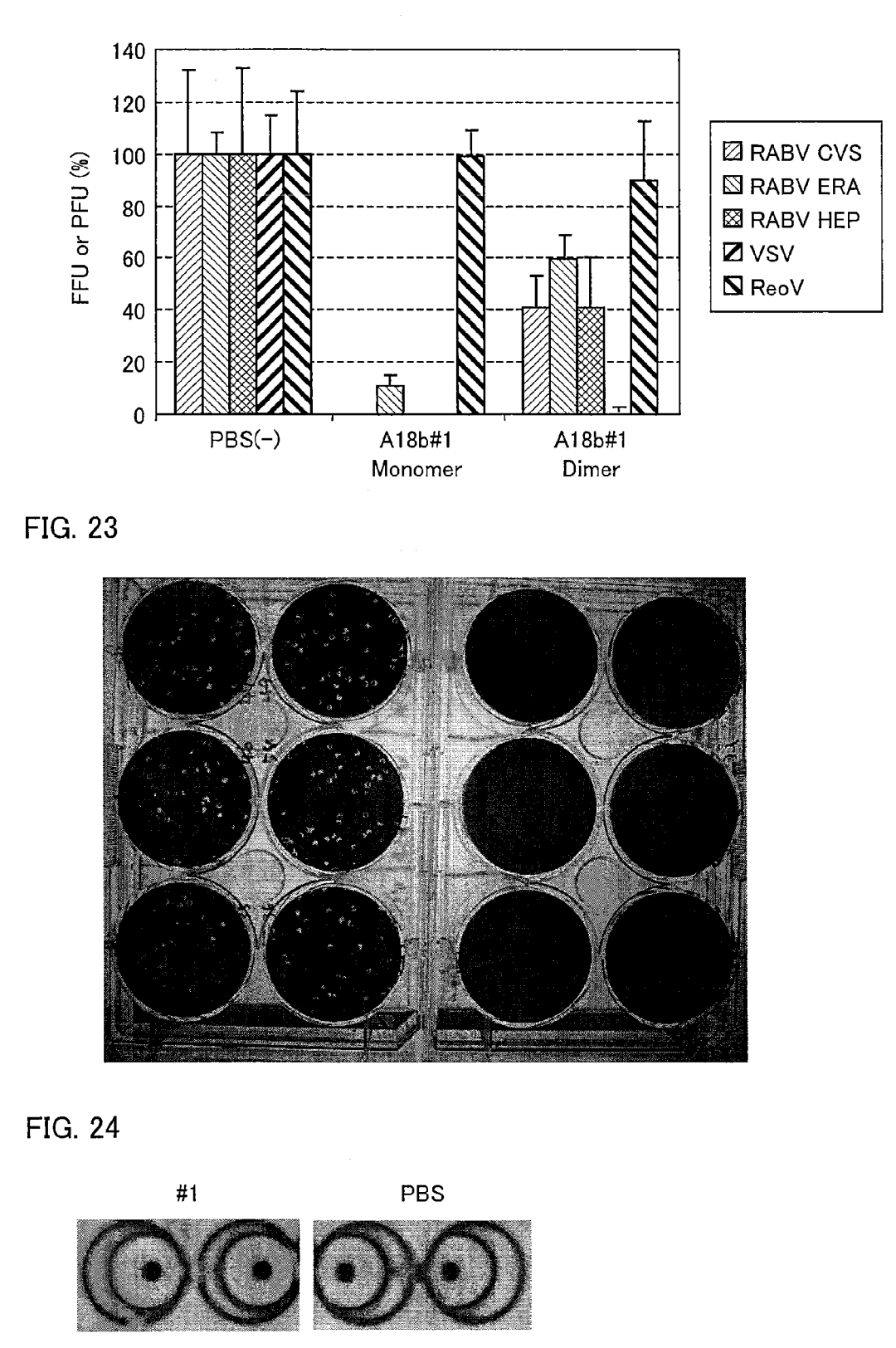

As illustrated in FIG. 22, the monomer (Monomer) configuration of the human abzyme derived from the clone #1 of germline A18b showed a very high anti virus activity against the viruses other than ReoV. For ERA of RABV, a small number of infection plaques was observed (about 10%). Moreover, the dimer (Dimer) configuration showed no anti virus activity against ReoV, but down-regulated the infection of the three strains of RABV and down-regulated the VSV infection by about 100%. This explained that the human abzyme according to the present invention can significantly down-regulate the infection of the RABV, even though there is a difference in degree of the down-regulation between the strains of RABV. Moreover, because the human abzyme according to the present invention showed very good down-regulation on the infection of VSV, it is considered that the human abzyme according to the present invention is effective to viruses belonging to Rhabdoviridae. Especially, the monomeric human abzyme is very high in anti virus activity, and is expected to show a high anti virus activity under various conditions.

As one example of this test, the result of the plaque assay on reaction between the monomeric human abzyme and CVS is shown in FIG. 23. As illustrated in FIG. 23, the 6 wells in the two columns from the left were infected with a mixture of PBS and the virus and many plaques were formed therein. On the other hand, the 6 wells in the 2 columns from right were infected with a mixture of the monomeric human abzyme and the virus, and showed utterly no plaque formed by the virus infection and amplification.

(3-5. Evaluation on Membrane-Fusing Activity)

As confirmed in FIG. 22, the human abzyme according to the present invention showed a high anti virus activity against viruses belonging to Rhabdoviridae, but showed almost no activity against ReoV. Viruses belonging to Rhabdoviridae have envelops derived from host cell membrane. Envelop viruses lose their infectiveness when the envelop is damaged. Moreover, if the human abzyme according to the present invention had an activity to damage the envelope, the human abzyme according to the present invention could be hazardous to the host cell as well. Thus, in order to check safety of the human abzyme of the present invention, whether the human abzyme of the present invention coagulate avian red blood cells or not was examined. The human abzyme according to the present invention or PBS was mixed and reacted at 25° C. for 48 hours with 1% avian red blood cell suspension. A result thereof is shown in FIG. 24. As shown in FIG. 24, the human abzyme according to the present invention caused no coagulation of the red blood cells. This means that the human abzyme according to the present invention has no membrane-fusing activity, whereby it is considered that the human abzyme according to the present invention has no activity to damage the host cell. That is, it can be considered that the human abzyme according to the present invention can be used as an antiviral agent having an anti virus activity effecting a protein specific to a virus, thereby being highly safe.

(3-6. Preparation of Monomer of Modified Human Antibody Light Chain)

Figure 25:
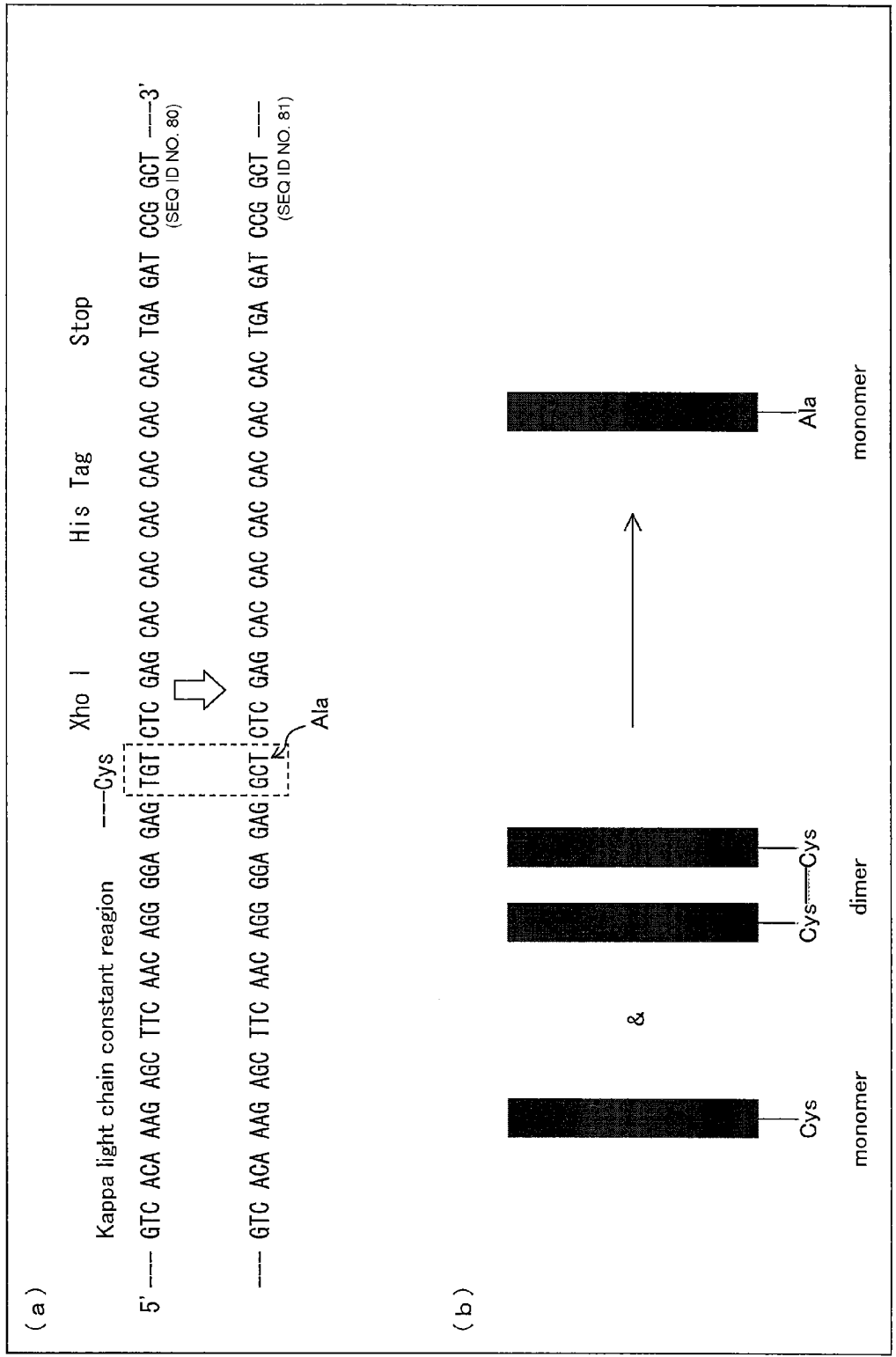
FIG. 25 describes designs of cDNA in an embodiment of the present invention. (a) of FIG. 25 schematically shows a design of cDNA for obtaining a monomeric human antibody light chain. (b) of FIG. 25 schematically shows composition of a human antibody light chain before and after mutation.

As described above, the human abzyme of the clone #1 (germline: A18b) showed a high antibody activity in the monomer configuration. In consideration of this, a cDNA for producing only the monomeric human abzyme was designed by introducing a mutation on the cysteine at the 220th site, which is considered to be essential for the formation of the dimer via the S—S bonding. Details of the design are shown in FIG. 25. As shown in (a) of FIG. 25, TGT for encoding the cysteine at the 220th site in the whole gene of the human abzyme was substituted with GCT. By this, only the monomer was obtained because the S—S bond was not formed due to the alanine at the 220th site in the substituted amino acid as shown in (b) of FIG. 25, even though the monomer and the dimer coexisted when the 220 amino acid was cysteine in the original amino acid sequence. As to a risk that the change in the conformation due to the amino acid substitution would possibly change the anti virus activity, it was confirmed that the human abzyme with the alanine substitution at 220th site showed an anti virus activity against the virus belonging to Rhabdoviridae, similarly to the anti virus activity confirmed in 3-4. In the following the procedure and result of the test are explained.

Incubation with the human abzyme and virus was carried out as described in 3-2. Virus infection was carried out as described in 3-3. As the human abzyme, the monomer with alanine substitution at 220th site was examined in terms of its anti virus activity against VSV virus. As in 3-3., plaque assay was used to find out the percentage of the number of plaques formed in the wells treated with a mixture of the human abzyme and the respective viruses, where the number of the plaques formed in the well treated with a mixture of PBS and the respective viruses was put as 100%. Results thereof are collectively plotted in the graph in FIG. 26.

Figure 26:
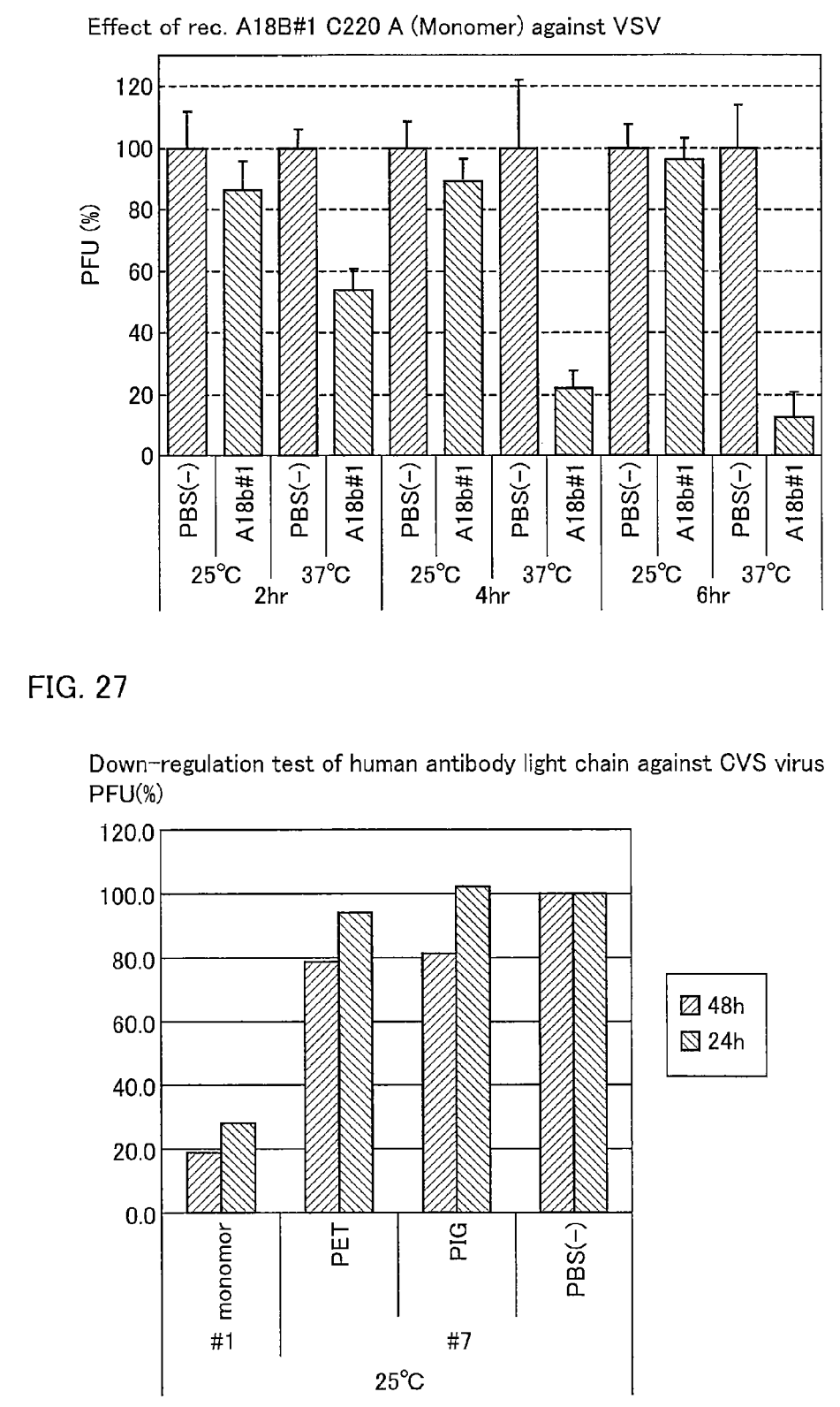

As illustrated in FIG. 26, the monomer with alanine substitution at 220th site showed virus down-regulation effect against the VSV virus. Especially, at 37° C., the virus down-regulation effect of the monomer with alanine substitution at 220th site was significant.

(3-8. Tests on Anti Virus Activity of Human Abzyme Derived from the Clone #7)

The human abzyme derived from the clone #7 was also tested on its virus down-regulation effect, as in the human abzyme derived from the clone #1. Incubation with the human abzyme and virus was carried out as described in 3-2. Virus infection was carried out as described in 3-3. As the human abzyme, the monomer with alanine substitution at 220th site was examined in terms of its anti virus activity against VSV virus. As in 3-3., plaque assay was used to find out the percentage of the number of plaques formed in the wells treated with a mixture of the human abzyme and the respective viruses, where the number of the plaques formed in the well treated with a mixture of PBS and the respective viruses was put as 100%. Results thereof are collectively plotted in the graph in FIG. 27.

As shown in FIG. 27, the human abzyme derived from the clone #7 showed an anti virus activity, even though it is inferior to that of the human abzyme derived from the clone #1.

(3-9. Tests on Anti Virus Activity of Clone 23D4)

The human abzyme derived from the clone 23D4 was also tested on its virus down-regulation effect, as in the human abzyme derived from the clone #1. Incubation with the human abzyme and virus was carried out as described in 3-2. Virus infection was carried out as described in 3-3. The human abzyme including only the monomer and the human abzyme including only dimer were individually examined in terms of their anti virus activity for the three trains of rabies virus, VSR, and ReoV. As in 3-3., plaque assay was used to find out the percentage of the plaque number formed in the wells treated with the mixture liquid of the human abzyme and the respective viruses, where the number of plaque formed in the well treated with the mixture liquid of PBS and the respective viruses was put as 100%. Results thereof are collectively plotted on the graph in FIG. 33.

Figure 33:
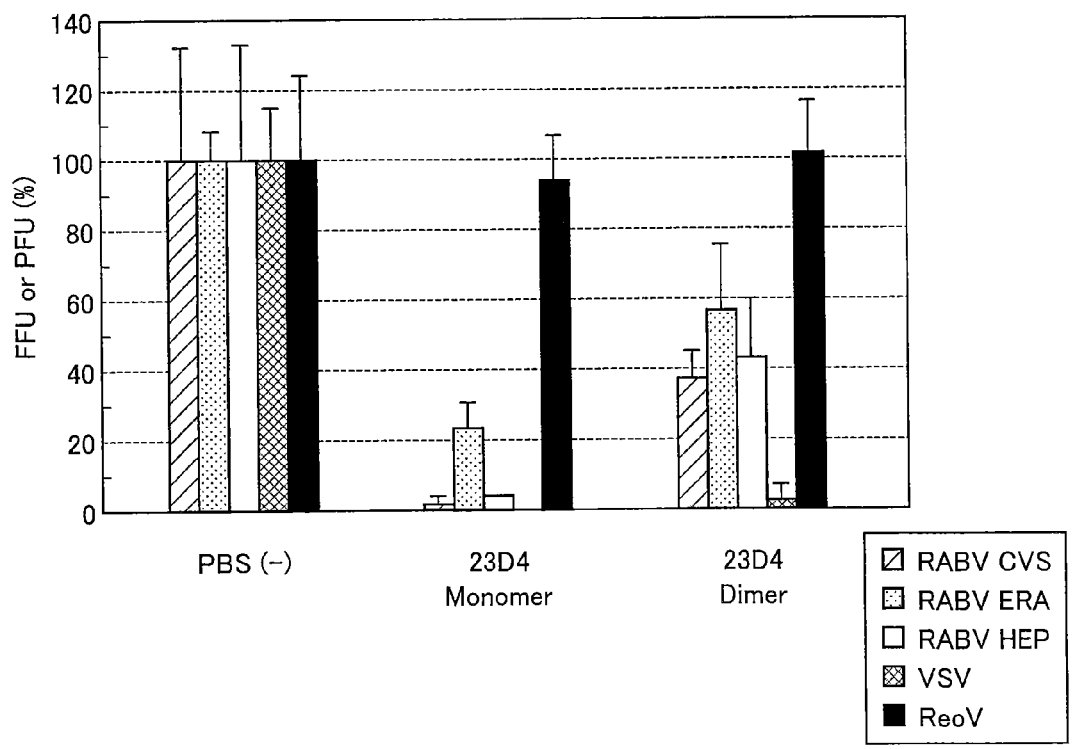
FIG. 33 shows a result of examination on antiviral activity of clone 23D4 for various viruses.

As shown in FIG. 33, the monomer (Monomer) configuration of the human abzyme of the clone 23D4 showed a very high anti virus activity against the viruses other than ReoV For ERA of RABV, a small number of infection plaques was observed (about 20%). The dimer (Dimer) configuration of the human abzyme of the clone 23D4 showed no anti virus activity against ReoV, but almost halved the infection with the three strains of RABV, and down-regulated the infection with VSV by almost 100%. Thus, it was found that this human abzyme according to the present invention remarkably down-regulate the RABV infection, even though there is a difference in degree of the down-regulation between the strains of RABV. Moreover, because this human abzyme according to the present invention showed very good down-regulation on the infection of VSV, it is considered that the human abzyme according to the present invention is effective to viruses belonging to Rhabdoviridae. Especially, the monomeric human abzyme is very high in anti virus activity, and is expected to show a high anti virus activity under various conditions.

(3-10. Evaluation on Membrane-Fusing Activity of Clone 23D4)

Figure 34:
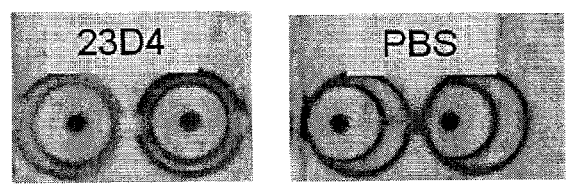
FIG. 34 shows a result of erythrocyte agglutination by which membrane fusion activity of clone 23D4 was examined.

As in 3-5., membrane-fusing activity of the clone 23D4 was evaluated. The evaluation showed that, as shown in FIG. 34, no coagulation of red blood cells was caused by this human abzyme. This means that the human abzyme according to the present invention has no membrane-fusing activity, whereby it is considered that the human abzyme according to the present invention has no activity to damage the host cell. That is, it can be considered that the human abzyme according to the present invention can be used as an antiviral agent having an anti virus activity effecting a protein specific to a virus, thereby being highly safe.

(3-11. Preparation of Monomer of Modified Human Antibody Light Chain)

As described above, the human abzyme according to the present invention showed a high antibody activity especially in the monomer configuration. In consideration of this, a cDNA for producing only the monomeric human abzyme was designed by introducing a mutation on the cysteine at the 220th site, which is considered to be essential for the formation of the dimer via the S—S bonding, as in 3-6. That is, TGT for encoding the cysteine at the 220th site in the whole gene of the human abzyme was substituted with GCTCTCGAG-CACCACCACCACCACCACTGA (SEQ ID NO: 13) for encoding ALEHHHHHH (SEQ ID NO: 12) (+stop codon). For example, the clone 23D4, the clone 22F6, and the clone 23F1 were mutated to the nucleotide sequences of SEQ ID NOS: 32, 37, and 42, respectively.

As a result, as shown in FIGS. 39 and 40, human antibody light chains in which the cysteine was substituted. The amino acid sequence of the human antibody light chain of the modified clone #1 is shown in SEQ ID NO: 15. The amino acid sequence of the human antibody light chain of the modified clone #16 is shown in SEQ ID NO: 17. The amino acid sequence of the human antibody light chain of the modified clone #7 is shown in SEQ ID NO: 19. The amino acid sequence of the human antibody light chain of the modified clone #6 is shown in SEQ ID NO: 23. The amino acid sequence of the human antibody light chain of the modified clone #18 is shown in SEQ ID NO: 27. The amino acid sequence of the human antibody light chain of the modified clone 23D4 is shown in SEQ ID NO: 31. The amino acid sequence of the human antibody light chain of the modified clone 22F6 is shown in SEQ ID NO: 36. The amino acid sequence of the human antibody light chain of the modified clone 23D4 is shown in SEQ ID NO: 41.

Figure 36:
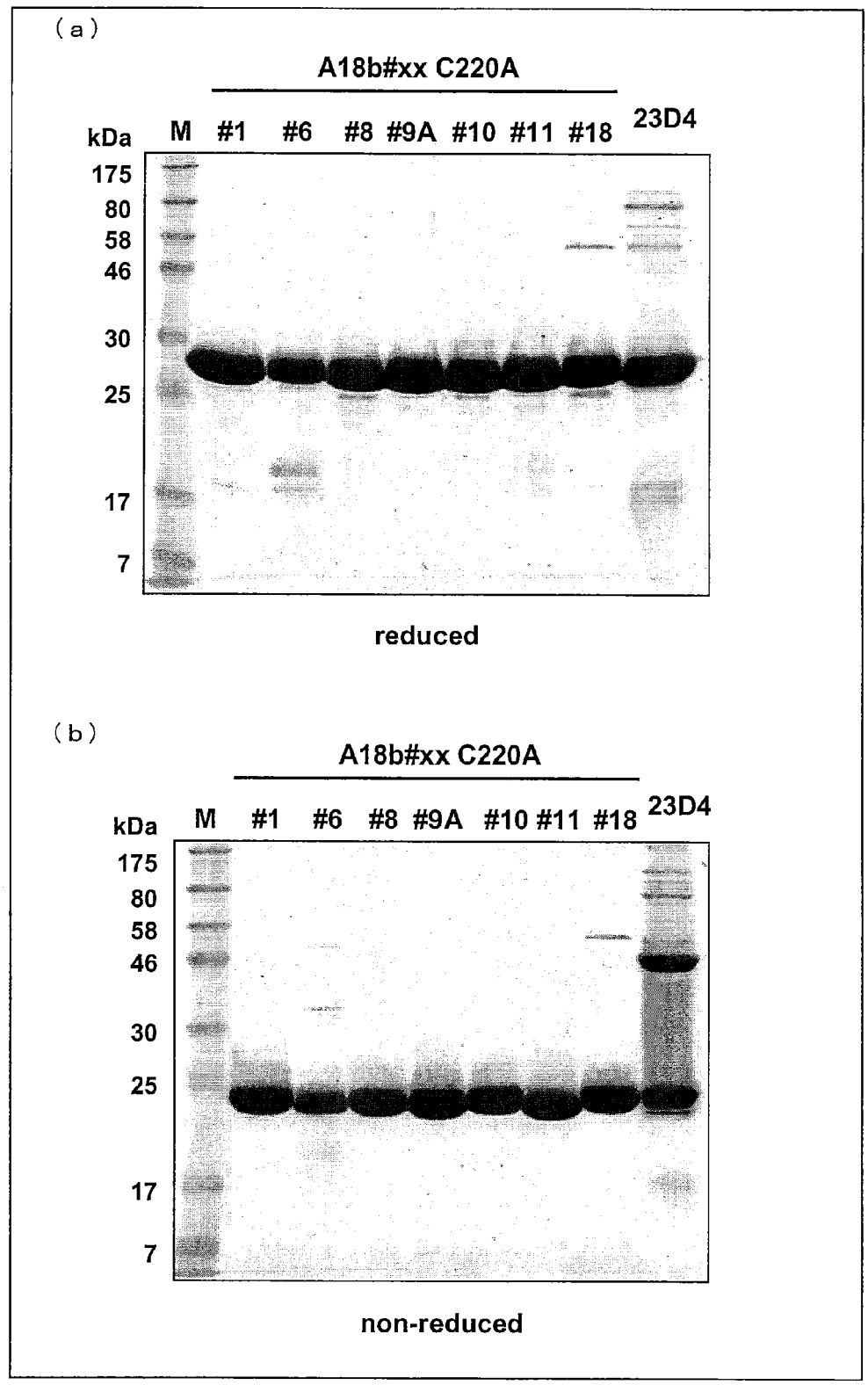
FIG. 36 shows a result of SDS-PAGE of a human antibody κ light chain in which a cysteine forming a disulfide bonding is substituted.

FIG. 36 shows results of electrophoresis of the modified human antibody light chain. As shown in FIG. 36, only monomer was obtained, because the S—S bond was not formed due to the alanine at the 220th site in the substituted amino acid, while a mixture of the monomer and dimer existed in the original amino acid sequence due to the 220th site was cysteine.

The anti virus activities of the modified human abzymes were also tested on its virus down-regulation effect. Incubation with the human abzyme and virus was carried out as described in 3-2. Virus infection was carried out as described in 3-3. As the human abzyme, the monomer having alanine substitution at 220th site was tested for its anti virus activity against VSV virus. As in 3-3., plaque assay was used to find out the percentage of the plaque number formed in the wells treated with the mixture liquid of the human abzyme and the respective viruses, where the number of plaque formed in the well treated with the mixture liquid of PBS and the respective viruses was put as 100%. Results thereof are collectively plotted on the graph in FIGS. 35, 37, and 38.

Figure 35:
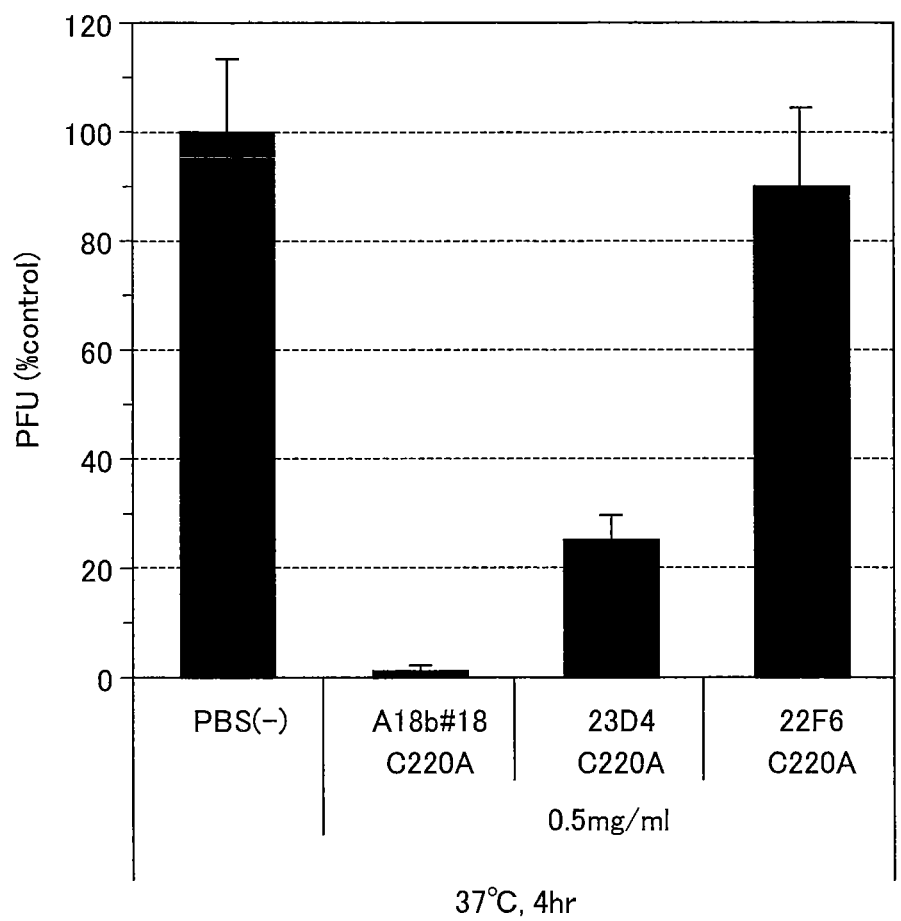
FIG. 35 is a result of examination on antiviral activity of clone 23D4.
Figure 37:
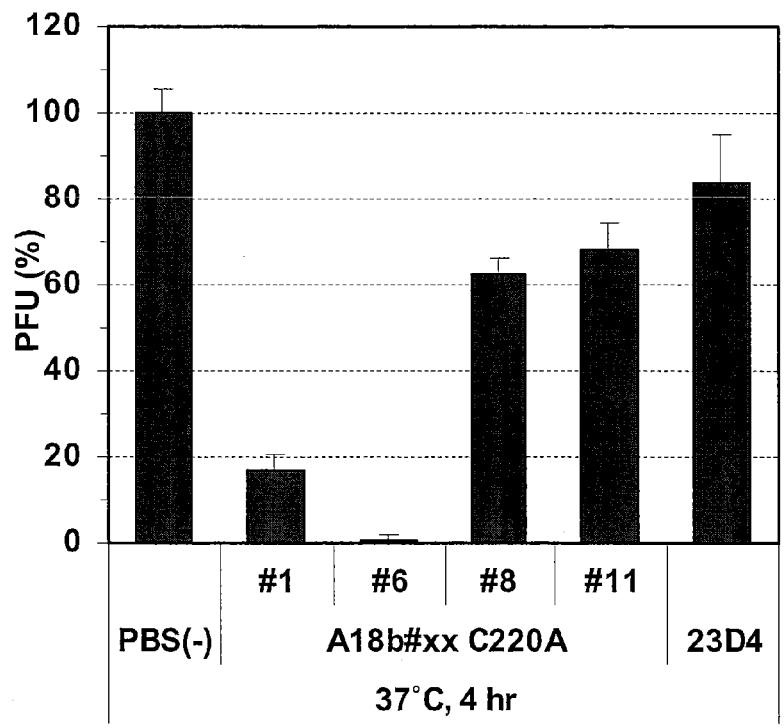
FIG. 37 shows a result of examination on antiviral activity of a human antibody κ light chain in which a cysteine forming a disulfide bonding is substituted.
Figure 38:
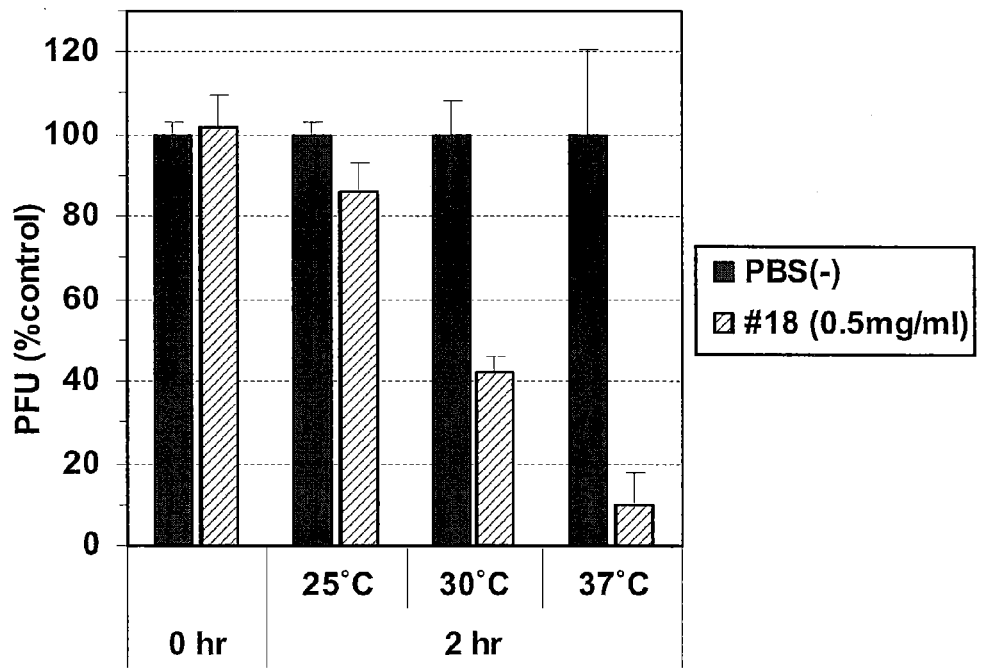
FIG. 38 shows a result of examination on antiviral activity of a human antibody κ light chain in which a cysteine forming a disulfide bonding is substituted.

As shown in FIG. 35, the human antibody light chains of the modified clone #18 and the modified clone 23D4 showed high anti virus activities. Moreover, as shown in FIG. 37, the human antibody light chains of the modified clone #1 and the modified clone #6 showed high anti virus activities as well. Furthermore, as shown in FIG. 38, the human antibody light chain of the modified clone #18 showed a remarkable anti virus activity especially at 37° C.

(3-12. Influenza Virus Infection Test)

Next, it was tested whether the human antibody light chain clones according to the present invention had a capability of down-regulating infection with influenza virus. As the influenza virus, A/Hiroshima/71/2001 (H3N2) strain was used. The virus was incubated in an allantoic cavity of a chicken egg after 11 days from hatching, thereby obtaining infected allantoic fluid, which was then kept at −80° C. until use. Cells to be infected were MDCK cells cultured in an Eagle's minimum essential medium (MEM) added with 10% bovine serum.

The sample of each clone was diluted to 20 μg/ml with PBS and then used. The influenza virus was diluted to about $5 \times 10^2$ or $5 \times 10^3$ PFU/0.2 ml with the Eagle's MEM. The sample and the virus were mixed in an equal amount (0.25 ml each), and incubated at 20° C. for 48 hours. After the incubation, an infection titer of the virus was determined by the plaque method. More specifically, the mixture of the sample and virus was pre-inoculated to a monolayer of the MDCK cells on a tissue culturing tray, and caused to adhered thereto at 37° C. for 60 min. After that, the inoculum was removed from the tissue culture tray, which was then washed with PBS. Then, the MDCK cells were covered with an MEM medium containing 1.0% agarose ME and 20 mg/ml trypsin (first covering medium), and incubated for 4 days in an 5% $CO_2$ incubator under humidified and 37° C. conditions. After that, the cells were covered with a second covering medium, which was identical with the first covering medium except that 0.005% neutral red was added. Plaque counting was conducted on the following day.

Figure 41:
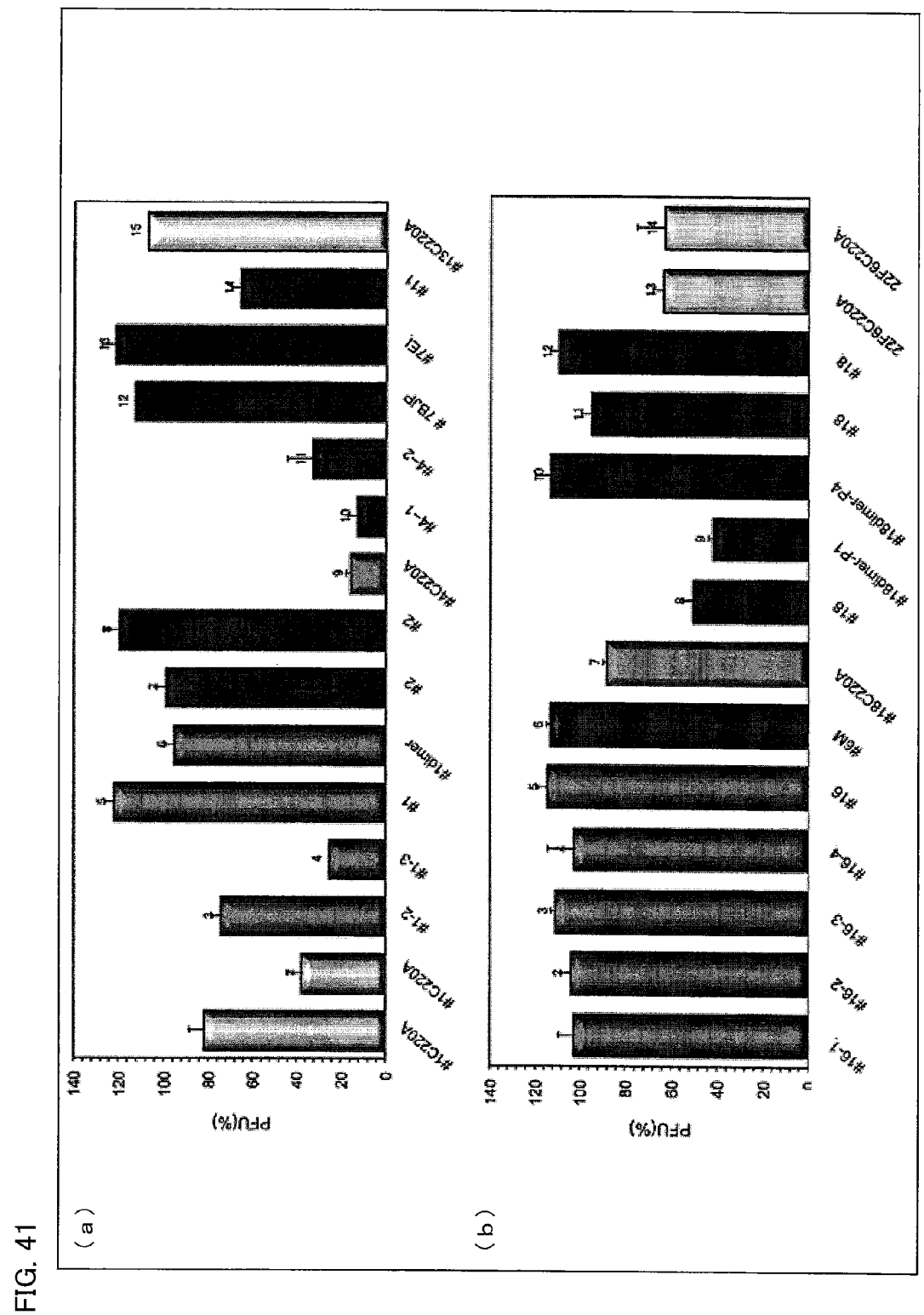
FIG. 41 is a graph showing a result of examination on antiviral activity of each clone for an influenza virus.

Results thereof are shown in (a) and (b) of FIG. 41. In FIG. 41, the infection titer are indicated as percentage with respect to control. Moreover, "dimer" indicates that the sample is a dimer, and "C220A" indicates that the sample is a monomeric amino acid sequence modified to avoid the disulfide bonding.

FIG. 36 shows results of electrophoresis of the modified human antibody light chains. As shown in FIG. 36, only the monomer was obtained from the amino acids with the substitution because the S—S bonding was not formed due to the 220th amino acid was alanine, whereas the monomer and the dimer existed together in case of the original amino acid sequence in which the 220th amino acid was cysteine.

(3-13. In Vivo Neutralization Test)

According to an internationally standard method, in vivo neutralization test was conducted for the anti virus activity of the human antibody light chain according to the present invention. That is, the rabies virus CVS (Challenge Virus Strain) and the antibody was reacted with each other in vivo for a certain time period, thereby obtain a reaction liquid, which was then inoculated to brains of mice. Based on survival rate of the mice, virus neutralization capacity of the antibody was evaluated.

Firstly, the CVS virus was diluted to a predetermined concentration with 10% FCS-EMEM medium. Then, the virus dilution liquid was mixed with the sample in an equal amount. Their mixture was incubated at 25° C. for 24 hours. After the incubation, a reaction liquid obtained as a result of the incubation was inoculated to ddy mice (7 weeks old, female) in an amount of 0.03 ml per head. After the inoculation, the mice were observed for 14 days and their survival rate was evaluated.

Table 7 shows the results of the test, where the concentration of the CVS virus was in a range of 1320 to 26400 FFU (Focus Forming Unit: number of virus)/ml, the sample (antibody light chain: LC) was 0.5 mg/ml of the clone #18, a positive control was 1 IU/ml of ERIG (Equine Rabies ImmunoGlobulin, polyclonal antibody), a negative control was PBS. In each column in Table 7, the number of mice survived at the times from the inoculation (0 day) to 14 days from the inoculation. Note that the virus infection titer of CVS is equivalent to 1 $LD_{50}$ in case of 1.5 FFU inoculation to mice per head.

TABLE 7

| d.p.i | 0 | 1 | 3 | 5 | 7 | 9 | 10 | 11 | 12 | 13 | 14 |
|---|---|---|---|---|---|---|---|---|---|---|---|
| 26400 FFU + PBS | 5 | 5 | 5 | 5 | 5 | 4 | 2 | 1 | 0 | 0 | 0 |
| 26400 FFU + LC | 6 | 6 | 6 | 6 | 6 | 6 | 4 | 3 | 1 | 1 | 1 |
| 26400 FFU + ERIG | 6 | 6 | 6 | 6 | 6 | 6 | 6 | 6 | 6 | 6 | 6 |
| LC + PBS | 4 | 4 | 4 | 4 | 4 | 4 | 4 | 4 | 4 | 4 | 4 |
| PBS | 3 | 3 | 3 | 3 | 3 | 3 | 3 | 3 | 3 | 3 | 3 |
| 13200 FFU + PBS | 6 | 6 | 6 | 6 | 4 | 4 | 2 | 1 | 1 | 1 | 1 |
| 13200 FFU + LC | 6 | 6 | 6 | 6 | 6 | 6 | 4 | 3 | 1 | 1 | 1 |
| 6600 FFU + PBS | 6 | 6 | 6 | 6 | 6 | 6 | 4 | 3 | 3 | 3 | 3 |
| 6600 FFU + LC | 6 | 6 | 6 | 6 | 6 | 6 | 4 | 3 | 3 | 3 | 3 |
| 3300 FFU + PBS | 6 | 6 | 6 | 6 | 6 | 6 | 5 | 4 | 4 | 4 | 4 |
| 3300 FFU + LC | 6 | 6 | 6 | 6 | 6 | 6 | 5 | 4 | 4 | 4 | 4 |
| 1320 FFU + PBS | 6 | 6 | 6 | 6 | 6 | 6 | 5 | 5 | 5 | 5 | 5 |
| 1320 FFU + LC | 6 | 6 | 6 | 6 | 5 | 5 | 5 | 5 | 5 | 5 | 5 |

As shown in Table 7, low virus concentrations (1320 to 6600 FFU/ml) did not kill the mice, thereby not allowing the evaluation. On the other hand, virus concentrations equal to or greater than 13200 FFU/ml allowed the evaluation. In Table 7, as indicated by the thick frame, the survival rate was clearly lower in the case where the clone #18 was reacted with the virus than in the case where PBS was reacted with the virus.

Next, in order to more certainly confirm the effect of the abzyme (clone #18), the test was repeated with greater concentrations. The virus dilution liquid of 26400 FFU/ml was used. As the samples to test, 5 mg/ml of the clone #18, 4.9 mg/ml of the clone #2, 5.9 mg/ml of the clone #4, and 0.94 mg/ml of the clone #18. Results thereof are shown in Table 8.

TABLE 8

| | d.p.i | | | | | | | | | | | | | | |
|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 |
| Virus + #18 (5 mg/ml) | 9 | 9 | 9 | 9 | 9 | 9 | 9 | 9 | 9 | 8 | 6 | 6 | 5 | 5 | 5 |
| Virus + #2 (4.9 mg/ml) | 9 | 9 | 9 | 9 | 9 | 9 | 9 | 9 | 9 | 4 | 2 | 1 | 0 | 0 | 0 |
| Virus + #4 (5.9 mg/ml) | 7 | 7 | 7 | 7 | 7 | 7 | 7 | 7 | 7 | 1 | 1 | 0 | 0 | 0 | 0 |
| Virus + #18 (0.94 mg/ml) | 6 | 6 | 6 | 6 | 6 | 6 | 6 | 6 | 6 | 6 | 4 | 3 | 1 | 1 | 1 |
| Virus + PBS | 10 | 10 | 10 | 10 | 10 | 10 | 10 | 10 | 10 | 7 | 3 | 1 | 0 | 0 | 0 |
| Virus + ERIG (2 IU/ml) | 11 | 11 | 11 | 11 | 11 | 11 | 11 | 11 | 11 | 11 | 11 | 11 | 11 | 11 | 11 |
| PBS | 3 | 3 | 3 | 3 | 3 | 3 | 3 | 3 | 3 | 3 | 3 | 3 | 3 | 3 | 3 |

As shown in Table 8, it was clearly confirmed that the clone #18 has a concentration-dependent capacity of down-regulating the virus (p value(Log–rank test)=0.0073 CVS+PBS vs. CVS+LC5 mg/ml).

(3-14. Nucleolytic Activity Test)

Nucleolytic activity test was conducted on the human antibody light chains according to the present invention. Samples purified by His-Tag purification and then positive ion column chromatography. For concentration of each sample, see Table 9. Nucleotide serving as a substrate was plasmid DNA (pBR322). As a negative control, unreacted substrate (Master Mix) was used. As a positive control, DNase 1 reacted was used. Each sample was reacted for 24 hours or 48 hours in a thermal cycler at 37° C. For the positive control, DNase 1 was reacted for 30 min. The negative control was incubated in the thermal cycler for 0 hour, 24 hours, or 48 hours. Then, the samples after the reaction were added with 10× loading buffer and mili Q water, and then frozen at −30° C. After that, the samples were subjected to agarose gel electrophoresis, part of whose results is shown in (a) of FIG. 42.

Figure 42:
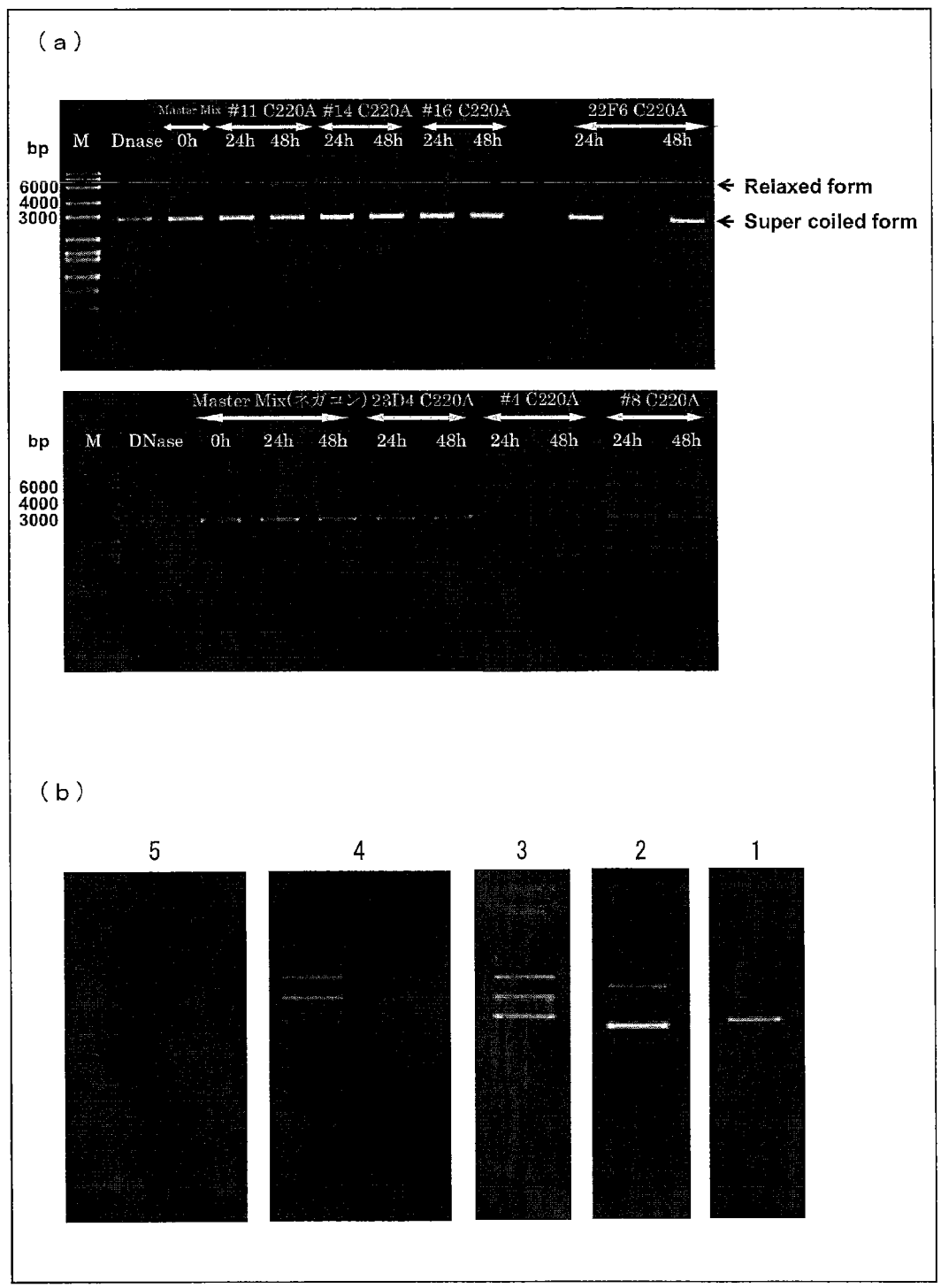
FIG. 42 shows a result of nucleic acid degradation studies of each clone.

In (a) of FIG. 42, the thick band near 300 bp indicates super-coiled DNA, while the band at 4000 to 6000 bp indicates relaxed DNA. (b) of FIG. 42 shows correspondence between levels of intensities of nucleolytic activity and states of the bands. The rightmost (1) indicates a state in which no activity was observed. The activity is increased toward the left (2 to 4). The leftmost indicates the highest activity. For example, as shown in (a) of FIG. 42, no DNA band was observed for the clone #4, thereby indicating the clone #4 has a high DNA decomposing activity ("5" in (b) of FIG. 42). Table 9 shows the result of each clone in the same way.

TABLE 9

| Clone | Conc. [mg/mL] | Results |
|---|---|---|
| #1 dimer | 1.9 | 3 |
| #1 dimer | 0.132 | 3 |
| #1 dimer | 0.171 | 2 |
| #2 dimer | 2.18 | 2 |
| #4 dimer | 3.5 | 5 |
| #4 dimer | 0.397 | 5 |
| #4 dimer | 0.326 | 5 |
| #11 dimer | 1.9 | 4 |
| #11 dimer | 0.62 | 4 |
| #16 dimer | 0.343 | 2 |
| 23D4 dimer | 1.6 | 2 |
| #1 C220A | 2.4 | 1 |
| #1 C220A (dimer-like) | 1.9 | 2 |
| #1 C220A | 2.1 | 1 |
| #4 C220A | 2.4 | 5 |
| #8 C220A | 1.9 | 1 |
| #9 C220A | 2.6 | 1 |
| #9 C220A | 2.2 | 1 |
| #11 C220A | 2.2 | 2 |
| #14 C220A | 2.6 | 1 |

TABLE 9-continued

| Clone | Conc. [mg/mL] | Results |
|---|---|---|
| #16 C220A | 2.5 | 1 |
| #18 C220A | 2.4 | 3 |
| #18 C220A | 2.3 | 2 |
| 22F6 C220A | 2.5 | 1 |
| 23D4 C220A | 2.1 | 3 |
| 23D4 C220A | 2.5 | 1 |

As shown in Table 9, it was found that apart from the clone 34, the clones #18, #1, 23D4, and #11 certainly had a nucleolytic activity.

Because abzymes having a nucleolytic activity are often found in serum of autoimmune symptom patients, it is deduced that the clones like the clones #4 have a function relating to autoimmune symptom. Moreover, there is a possibility that the clones like the clones #4 have an ability to destroy virus DNA.

(3-15. Test on Cytotoxicity to Cancer Cells)

The human antibody light chain clones according to the present invention were tested on cytotoxicity to cancer cells. Firstly, the following human antibody chains were prepared in the way described above: #1_C220A (the monomeric clone #1), #1_dimer (the dimer of the clone #1), 23D4_C220A (the monomeric 23D4 clone), 23D4_dimer (the dimer of the 23D4 clone), #4_C220A (the monomeric clone #4), #9a_C220A (the monomeric clone #9), and #13_C220A (the monomeric clone #13). Note that in this Specification, the "C220A" indicates a monomer obtained by modifying the 220th amino acid from cysteine to alanine in order to prevent the disulfide bonding, and the "dimer" was a dimer prepared from a wild type.

Moreover, a cell culture liquid of SNU-1 (human stomach cancer strain) purchased from ATCC was inoculated to a 96-well plate in an amount of $3 \times 10^4$ cells/well. A cell culture liquid of A549 (human lung cancer strain) also purchased from ATCC was inoculated to a 96-well plate in an amount of $5 \times 10^4$ cells/well. For SNU-1. RPMI-164 medium added with 10% bovine embryo serum was used as its medium and the later described human antibody light chain was added concurrently with the cell inoculation. For A549 cells, the cells were incubated for 24 hours in F-12 medium added with 10% bovine embryo serum, so as to settle the cells therein. Then, the culture liquid was discarded. After that, F-12K medium (no serum added) added with the later-described antibody light chains was added therein.

The human antibody light chains added to SNU-1 and A549 were as follows: #1_C220A (1.0 mg/ml), #1_dimer (1.05 mg/ml), 23D4_C220A (1.05 mg/ml), 23D4_dimer (0.7 mg/ml), #4_C220A (1.2 mg/ml), #9a_C220A (1.3 mg/ml), and #13_C220A (1.4 mg/ml). After that, the samples were incubated for 24 hours, and then subjected to WST assay (WST-1 Roche), $\lambda_1$=450 nm, $\lambda_2$=620 nm). Results thereof are shown in FIG. 51.

Figure 51:
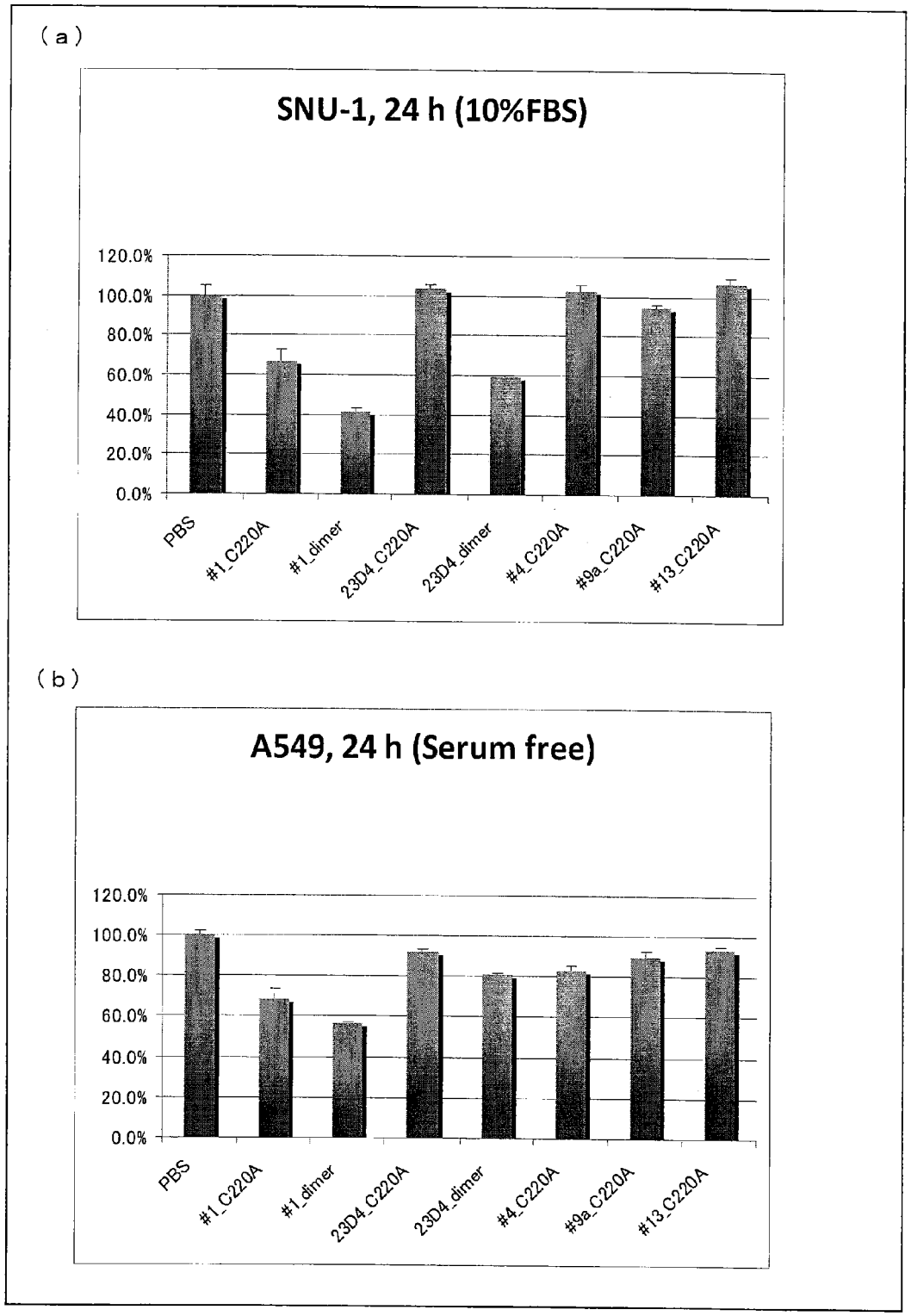
FIG. 51 is a graph showing a result of examination on cytotoxicity of each clone for a cancer cell.

(a) of FIG. 51 is a graph showing cytotoxicities of the human antibody light chains against SNU-1, whereas (b) of FIG. 51 is a graph showing cytotoxicities of the human antibody light chains against A549. As shown in FIG. 51, #1_C220A and #1_dimer showed strong anti cancer activities. Moreover, 23D4_dimer and #4_C220A showed weak anti cancer activity against A549. Moreover, 23D4_dimer showed strong cytotoxicity against SNU-1. Meanwhile, #9a_C220A and #13_C220A showed almost no cytotoxicity to the cancer cells.

Moreover, cell culture liquids of SNU-1 (human stomach cancer strain) and A549 (human lung cancer strain) purchased from ATCC was inoculated to 96-well plates in an amount of $1.6\times10^4$ cells/well (1 to $5\times10^5$ cells/ml), respectively. For medium, Dulbecco's modified Eagle's medium (high glucose) added with 1.5 g/l of sodium bicarbonate was used. For SNU-1, 10% bovine embryo serum was added in the cell culture liquid. For A549, no serum was added in the cell culture liquid.

Next, the human antibody light chains were added to the cell culture liquids of the cancer cell strains on the plates to make up the following final concentration: #1_C220A (1.0 mg/ml), #1_dimer (1.05 mg/ml), 23D4_C220A (1.05 mg/ml), 23D4_dimer (0.7 mg/ml), #4_C220A (1.2 mg/ml), #9a_C220A (1.3 mg/ml), and #13_C220A (1.0 mg/ml). After that, the samples were subjected to 24-hours incubation and WST assay (WST-1 (Roche), $\lambda_1$=450 nm, $\lambda_2$=620 nm). Results thereof are shown in FIG. 51.

(a) of FIG. 51 is a graph showing cytotoxicities of the human antibody light chains against SNU-1, whereas (b) of FIG. 51 is a graph showing cytotoxicities of the human antibody light chains against A549. As shown in FIG. 51, #1_C220A and #1_dimer showed strong anti cancer activities. Moreover, 23D4_dimer and #4_C220A showed weak anti cancer activity against A549. Moreover, 23D4_dimer showed strong cytotoxicity against SNU-1. Meanwhile, #9a_C220A and #13_C220A showed almost no cytotoxicity to the cancer cells.

INDUSTRIAL APPLICABILITY

The present invention is applicable to development of medical treatment, pharmaceutical production, test reagent development, medical instrument development, and food product development.

The invention claimed is:

1. A human abzyme comprising one of the following (a) through (f):
- (a) a human antibody kappa (κ) light chain with a variable domain consisting of SEQ ID NO: 26, and a constant domain with an Ala in the position corresponding to Cys219 in the amino acid sequence shown in SEQ ID NO: 24;
- (b) a human antibody kappa (κ) light chain with a variable domain consisting of SEQ ID NO: 14, and a constant domain with an Ala in the position corresponding to Cys220 in the amino acid sequence shown in SEQ ID NO: 1;
- (c) a human antibody kappa (κ) light chain with a variable domain consisting of SEQ ID NO: 50, and a constant domain with an Ala in the position corresponding to Cys220 in the amino acid sequence shown in SEQ ID NO: 48;
- (d) a human antibody kappa (κ) light chain with a variable domain consisting of SEQ ID NO: 35, and a constant domain with an Ala in the position corresponding to Cys219 in the amino acid sequence shown in SEQ ID NO: 33;
- (e) a human antibody kappa (κ) light chain with a variable domain consisting of SEQ ID NO: 54, and a constant domain with an Ala in the position corresponding to Cys219 in the amino acid sequence shown in SEQ ID NO: 52; or
- (f) a human antibody kappa (κ) light chain with a variable domain consisting of SEQ ID NO: 22, and a constant domain with an Ala in the position corresponding to Cys219 in the amino acid sequence shown in SEQ ID NO: 20.

2. The human abzyme as set forth in claim 1, wherein:
the human abzyme has an anti rhabdovirus activity, and anti influenza virus activity; and
the variable domain consists of SEQ ID NO: 26,
the constant domain has an Ala in the position corresponding to Cys219 in the amino acid sequence shown in SEQ ID NO: 20.

3. The human abzyme as set forth in claim 1, wherein:
the human abzyme has an anti rhabdovirus activity, anti influenza virus activity, and cytotoxicity against cancer cells; and
the variable domain consists SEQ ID NO: 14,
the constant domain has an Ala in the position corresponding to Cys220 in the amino acid sequence shown in SEQ ID NO: 1.

4. The human abzyme as set forth in claim 1, wherein:
the human abzyme has an anti influenza virus activity and nucleolytic activity; and
the variable domain consists of SEQ ID NO: 50,
the constant domain has an Ala in the position corresponding to Cys220 in the amino acid sequence shown in SEQ ID NO: 48.

5. The human abzyme as set forth in claim 1, wherein:
the human abzyme has an anti influenza virus activity; and
the variable domain consists of SEQ ID NO: 35,
the constant domain has an Ala in the position corresponding to Cys219 in the amino acid sequence shown in SEQ ID NO: 33.

6. The human abzyme as set forth in claim 1, wherein:
the human abzyme has an anti influenza virus activity; and
the variable domain consists of SEQ ID NO: 54,
the constant domain has an Ala in the position corresponding to Cys219 in the amino acid sequence shown in SEQ ID NO: 52.

7. The human abzyme as set forth in claim 1, wherein:
the human abzyme has an anti rhabdovirus activity; and
the variable domain consists of SEQ ID NO: 22,
the constant domain has an Ala in the position corresponding to Cys219 in the amino acid sequence shown in SEQ ID NO: 20.

8. A method for treating a patient of a rhabdovirus infectious disease by administering a human abzyme comprising a human antibody kappa (κ) light chain with a variable domain consisting of SEQ ID NO: 26, 14, 30, or 22 to the patient, wherein the administering does not comprise administering a human antibody heavy chain.

9. A method for treating a patient of an influenza virus infectious disease by administering a human abzyme comprising a human antibody kappa (κ) light chain with a variable domain consisting of SEQ ID NO: 26, 14, 50, 35 or 54 to the patient.

* * * * *